(12) United States Patent
Weiner et al.

(10) Patent No.: US 10,201,598 B2
(45) Date of Patent: Feb. 12, 2019

(54) SYNTHETIC IMMUNOGENS FOR PROPHYLAXIS OR TREATMENT OF TUBERCULOSIS

(71) Applicant: The Trustees of the University of Pennsylvania, Philadelphia, PA (US)

(72) Inventors: David B. Weiner, Merion, PA (US); Daniel Villarreal, San Diego, CA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 15/715,300

(22) Filed: Sep. 26, 2017

(65) Prior Publication Data
US 2018/0078631 A1 Mar. 22, 2018

Related U.S. Application Data

(62) Division of application No. 14/774,399, filed as application No. PCT/US2014/030776 on Mar. 17, 2014, now Pat. No. 9,789,175.

(60) Provisional application No. 61/800,375, filed on Mar. 15, 2013.

(51) Int. Cl.
| | |
|---|---|
| *C07K 14/00* | (2006.01) |
| *A61K 39/04* | (2006.01) |
| *A61K 39/07* | (2006.01) |
| *A61K 45/06* | (2006.01) |
| *A61K 39/00* | (2006.01) |

(52) U.S. Cl.
CPC .............. *A61K 39/04* (2013.01); *A61K 39/07* (2013.01); *A61K 45/06* (2013.01); *A61K 2039/53* (2013.01)

(58) Field of Classification Search
CPC ..................................................... A61K 39/04
See application file for complete search history.

(56) References Cited

U.S. PATENT DOCUMENTS

| | | | |
|---|---|---|---|
| 2003/0054338 A1 | 3/2003 | Dahlberg et al. | |
| 2003/0147897 A1 | 8/2003 | Andersen et al. | |
| 2005/0118201 A1 | 6/2005 | Wright et al. | |
| 2010/0081151 A1* | 4/2010 | Farias-Eisner | ............................. G01N 33/57449 435/7.23 |
| 2010/0129391 A1 | 5/2010 | Reed et al. | |
| 2012/0039925 A1 | 2/2012 | Dietrich et al. | |

FOREIGN PATENT DOCUMENTS

| | | |
|---|---|---|
| CN | 101805397 A | 8/2010 |
| CN | 101912605 A | 12/2010 |
| WO | 9951748 | 10/1999 |
| WO | 2010121618 A1 | 10/2010 |

OTHER PUBLICATIONS

Brodin et al., "ESAT-6 proteins: protective antigens and virulence factors?". TRENDS in Microbiology, 12(11):500-508, (Nov. 2004).
Zvi et al., "Whole genome identification of *Mycobacterium tuberculosis* vaccine candidates by comprehensive data mining and bioinformatic analyses". BMC MediCal Genomics, 1(18):1-25, (May 28, 2008).
Kamath et al., "Differential protective efiicacy of DNA vaccines expressing secreted proteins of *Mycobacterium tuberculosis*". Infection and Immunity, 67(4):1702-1707, (Apr. 1, 1999).
Andersen et al., "TB subunit vaccines-putting the pieces together". Microbes and Infection, 7(5-6):911-921, (2005).
Villarreal et al., "Multivalent TB vaccines targeting the esx gene family generate potent and broad cell-mediated immune responses superior to BCG". Human Vaccines & Immunotherapeutics, 10(8):2188-2198, (Jun. 23, 2014).
Deng et al., "Comparative Genomic and Proteomic Anatomy of *Mycobacterium ubiquitous* Esx Family Proteins: Implications in Pathogenicity and Virulence," CUff Microbiol, 68:558-567, 2014.
Uplekar et al., "Comparative Genomics of esx Genes from Clinical Isolates of *Mycobacterium tuberculosis* Provides Evidence for Gene Conversion and Epitope Variation," Infection and Immunity, vol. 79, No. 10, pp. 4042-4049, 2011.

* cited by examiner

*Primary Examiner* — Albert M Navarro
(74) *Attorney, Agent, or Firm* — Riverside Law LLP

(57) ABSTRACT

Compositions comprising a nucleic acid molecule that encodes TB esat-6 proteins are disclosed. Methods of inducing an immune response against TB an individual are disclosed. Method of treating an individual who has been diagnosed with TB are disclosed. Method of preventing TB infection in an individual are disclosed.

10 Claims, 29 Drawing Sheets
Specification includes a Sequence Listing.

pVSW (327aa) SEQ ID NO:2

*MDWTWILFLVAAATRVHS*TINYQFGDVDAHGAMIRAQAGSLEAEHQAIISDVLTASDFWGGAG
SAACQGFITQLGRNFQVIYEQANAHGQKVQAAGNNMAQTDSAVGSSWArgrkrrsSLLDAHIPQ
LIASHTAFAAKAGLMRHTIGQAEQQAMSAQAFHQGESAAAFQGAHARFVAAAAKVNTLLDIAQ
ANLGEAAGTYVAADAAAASSYTGFrgrkrrsTSRFMTDPHAMRDMAGRFEVHAQTVEDEARRM
WASAQNI<u>A</u>GAGWSGMAEATSLDTMTQMNQAFRNIVNMLHGVRDGLVRDANNYEQQEQASQ
QILSSYPYDVPDYA pDQE (355aa) SEQ ID NO:4

*MDWTWILFLVAAATRVHS*ADTIQVTPQMLRSTANDIQANMEQAMGIAKGYLANQENVMNPAT
WSGTGVVASHMTATEITNELNKVLTGGTRLAEGLVQAAALMEGHEADSQTAFQALFGASHGSr
grkrrsSQSMYSYPAMTANVGDMAGYTGTTQSLGADIASERTAPSRACQGDLGMSHQDWQAQ
WNQAMEALARAYRRCRRALRQIGVLERPVGDSSDCGTIRVGSFRGRWLDPRHAGPATAADA
GDrgrkrrsDPTVLADAVARMAEFGRHVEELVAEIESLVTRLHVTWTGEGAAAHAEAQRHWAA
GEAMMRQALAQLTAAGQSAHANY<u>A</u>GAMATNLGMWSYPYDVPDYA pHAT (329aa) SEQ ID NO:6

*MDWTWILFLVAAATRVHS*SQIMYNYPAMLGHAGDMAGYAGTLQSLGAEIAVEQAALQSAWQG
DTGITYQAWQAQWNQAMEDLVRAYHAMSSTHEANTMAMMARDTAEAAKWGGrgrkrrsTEQ
QWNFAGIEAAASAIQGNV<u>A</u>SIHSLLDEGKQSLTKLAAAWGGSGSEAYQGVQQKWDATATELN
NALQNLARTISEAGQAMASTEGNV<u>A</u>GMFArgrkrrsNADPVLSYNFDAIEYSVRQEIHTTAARFN
AALQELRSQIAPLQQLWTREAAAAYHAEQLKWHQAASALNEILIDLGNAVRHGADDVAHADRR
AAGAWARYPYDVPDYA

FIG. 2A pBCU (358aa) SEQ ID NO:8
*MDWTWILFLVAAATRVHS*AEMKTDAATLAQEAGNFERISGDLKTQIDQVESTAGSLQGQWRG
AAGTAAQAAVVRFQEAANKQKQELDEISTNIRQAGVQYSRADEEQQQALSSQMGFrgrkrrsSD
QITYNPGAVSDFASDVGSRAGQLHMIYEDTASKTNALQEFFAGHGAQGFFDAQAQMLSGLQG
LIETVGQHGTTTGHVLDNAIGTDQAIAGLFrgrkrrsVEPGRIGGNQARLAAVLLDVSTPNTLNAD
FDLMRSVAGITDARNEEIRAMLQAFIGRMSGVPPSVWGGLAAARFQDVVDRWNAESTRLYHV
LHAIADTIRHNEAALREAGQIHARHIAAAGGDLYPYDVPDYA pORF (331aa) SEQ ID NO:10
*MDWTWILFLVAAATRVHS*TINYQFGDVDAHGAMIRAQAGLLEAEHQAIVRDVLAAGDFWGGAG
SVACQEFITQLGRNFQVIYEQANAHGQKVQAAGNNMAQTDSAVGSSWArgrkrrsSQIMYNYP
AMMAHAGDMAGYAGTLQSLGADIASEQAVLSSAWQGDTGITYQGWQTQWNQALEDLVRAYQ
SMSGTHESNTMAMLARDGAEAAKWGGrgrkrrsGADDTLRVEPAVMQGFAASLDGAAEHLAV
QLAELDAQVGQMLGGWRGASGSAYGSAWELAHRGAGEVQLGLSMLAAAIAHAGAGYQHNE
AASAQVLREVGGGYPYDVPDYA BE6 (443aa) SEQ ID NO:12
*MDWTWILFLVAAATRVHS*TDVSRKIRAWGRRLMIGTAAAVVLPGLVGLAGGAATAGAFSRPGL
PVEYLQVPSPSMGRDIKVQFQSGGNNAPAVYLLDGLRAQDDYNGWDINTPAFEWYYQSGLSI
VMPVGGQSSFYSDWYSPACGKAGCQTYKWETFLTSELPQWLSANRAVKPTGSAAIGLSMAG
SSAMILAAYHPQQFIYAGSLSALLDPSQGMGPSLIGLAMGDAGGYKAADMWGPSSDPAWERN
DPTQQIPKLVANNARLWVYCGNGAPNELGGANIPAEFLENFVRSSNLKFQDAYNAAGGHNAV
FNFPPNGAHSAEYWGAQLNAMKGDLQSSLGAGrgrkrrsTEQQWNFAGIEAAASAIQGNVASI
HSLLDEGKQSLTKLAAAWGGSGSEAYQGVQQKWDATATELNNALQNLARTISEAGQAMASTE
GNVAGMFA AE6 (456aa) SEQ ID NO:14
*MDWTWILFLVAAATRVHS*QLVDRVRGAVTGMSRRLVVGAVGAALVSGLVGAVGGTATAGAFS
RPGLPVEYLQVPSPSMGRDIKVQFQSGGANSPALYLLDGLRAQDDFSGWDINTPAFEWYDQS
GLSVVMPVGGQSSFYSDWYQPACGKAGCQTYKWETFLTSELPGWLQANRHVKPTGSAVVGL
SMAASSALTLAIYHPQQFVYAGAMSGLLDPSQAMGPTLIGLAMGDAGGYKASDMWGPKEDPA
WQRNDPLLNVGKLIANNARVWVYCGNGKPSDLGGNNLPAKFLEGFVRTSNIKFQDAYNAGGG
HNGVFDFPDSGTHSAEYWGAQLNAMKPDLQRALGATPNTGPAPQGArgrkrrsTEQQWNFAG
IEAAASAIQGNVASIHSLLDEGKQSLTKLAAAWGGSGSEAYQGVQQKWDATATELNNALQNLA
RTISEAGQAMASTEGNVAGMFA

FIG. 2B

TE6 (314aa) SEQ ID NO:16
*MDWTWILFLVAAATRVHS*TEQQWNFAGIEAAASAIQGNVASIHSLLDEGKQSLTKLAAAWGGS
GSEAYQGVQQKWDATATELNNALQNLARTISEAGQAMASTEGNVAGMFArgrkrrsTEQQWN
FAGIEAAASAIQGNVASIHSLLDEGKQSLTKLAAAWGGSGSEAYQGVQQKWDATATELNNALQ
NLARTISEAGQAMASTEGNVAGMFArgrkrrsTEQQWNFAGIEAAASAIQGNVASIHSLLDEGKQ
SLTKLAAAWGGSGSEAYQGVQQKWDATATELNNALQNLARTISEAGQAMASTEGNVAGMFA phDV (671aa) SEQ ID NO:18
*MDWTWILFLVAAATRVHS*SQIMYNYPAMLGHAGDMAGYAGTLQSLGAEIAVEQAALQSAWQG
DTGITYQAWQAQWNQAMEDLVRAYHAMSSTHEANTMAMMARDTAEAAKWGGrgrkrrsTEQ
QWNFAGIEAAASAIQGNVASIHSLLDEGKQSLTKLAAAWGGSGSEAYQGVQQKWDATATELN
NALQNLARTISEAGQAMASTEGNVAGMFArgrkrrsVEPGRIGGNQARLAAVLLDVSTPNTLNA
DFDLMRSVAGITDARNEEIRAMLQAFIGRMSGVPPSVWGGLAAARFQDVVDRWNAESTRLYH
VLHAIADTIRHNEAALREAGQIHARHIAAAGGDLrgrkrrsTSRFMTDPHAMRDMAGRFEVHAQT
VEDEARRMWASAQNIAGAGWSGMAEATSLDTMTQMNQAFRNIVNMLHGVRDGLVRDANNY
EQQEQASQQILSSrgrkrrsADTIQVTPQMLRSTANDIQANMEQAMGIAKGYLANQENVMNPAT
WSGTGVVASHMTATEITNELNKVLTGGTRLAEGLVQAAALMEGHEADSQTAFQALFGASHGSr
grkrrsTINYQFGDVDAHGAMIRAQAGSLEAEHQAIISDVLTASDFWGGAGSAACQGFITQLGRN
FQVIYEQANAHGQKVQAAGNNMAQTDSAVGSSWAYPYDVPDYA

FIG. 2B CONTINUED

SEQUENCE LISTING

```
<160> NUMBER OF SEQ ID NOS: 31

<210> SEQ ID NO 1
<211> LENGTH: 987
<212> TYPE: DNA
<213> ORGANISM: Artificial Sequence
<220> FEATURE:
<223> OTHER INFORMATION: pVSW nucleic acid sequence

<400> SEQUENCE: 1
atggactgga catggattct gttcctggtc gccgccgcaa caagagtgca ttcaactatc      60
aattatcagt ttggagacgt ggacgcacac ggtgccatga tcagagccca ggctgggtca     120
ctggaggctg aacatcaggc aatcattagt gacgtgctca ctgcttcaga tttctggggc     180
ggagccggga gtgccgcttg ccagggtttc atcacccagc tgggccggaa ctttcaggtc     240
```

```
atctacgagc aggcaaatgc acacggtcag aaggtccagg cagcaggaaa caatatggct    300
cagaccgact ccgcagtcgg aagctcctgg gctagagggc ggaagaggag atctagtctg    360
ctcgatgccc acatccccca gctgattgcc tctcatacag ctttcgctgc aaaagccgga    420
ctcatgcgac atactatcgg gcaggcagag cagcaggcca tgtctgctca ggcatttcac    480
cagggagaaa gtgccgctgc attccaggga gcacatgctc gatttgtggc agctgcagcc    540
aaggtcaaca cactgctcga cattgcacag gccaatctgg gagaggctgc aggtacctac    600
gtggcagctg atgcagccgc tgcatcaagc tatacaggct ccgcggacg aaaacggcgc    660 tccacttcta ggtttatgac cgaccctcac gctatgaggg atatggccgg aagattcgag    720
gtgcatgctc agacagtcga ggacgaagcc cgaaggatgt gggctagcgc acagaacatc    780
gcaggagctg gttggagcgg aatggcagaa gccacttccc tggataccat gacacagatg    840
aatcaggcct ttagaaacat tgtgaatatg ctgcacggcg tgcgggacgg actcgtccgc    900
gatgccaaca attatgagca gcaggaacag gcttcccagc agattctctc cagttaccca    960
tacgatgtcc ccgattacgc ataataa                                        987
```

<210> SEQ ID NO 2
<211> LENGTH: 327
<212> TYPE: PRT
<213> ORGANISM: Artificial Sequence
<220> FEATURE:
<223> OTHER INFORMATION: VSW amino acid

<400> SEQUENCE: 2

```
Met Asp Trp Thr Trp Ile Leu Phe Leu Val Ala Ala Thr Arg Val
 1               5                  10                  15

His Ser Thr Ile Asn Tyr Gln Phe Gly Asp Val Asp Ala His Gly Ala
                20                  25                  30

Met Ile Arg Ala Gln Ala Gly Ser Leu Glu Ala Glu His Gln Ala Ile
            35                  40                  45

Ile Ser Asp Val Leu Thr Ala Ser Asp Phe Trp Gly Gly Ala Gly Ser
        50                  55                  60

Ala Ala Cys Gln Gly Phe Ile Thr Gln Leu Gly Arg Asn Phe Gln Val
65                  70                  75                  80

Ile Tyr Glu Gln Ala Asn Ala His Gly Gln Lys Val Gln Ala Ala Gly
                85                  90                  95

Asn Asn Met Ala Gln Thr Asp Ser Ala Val Gly Ser Ser Trp Ala Arg
            100                 105                 110

Gly Arg Lys Arg Arg Ser Ser Leu Leu Asp Ala His Ile Pro Gln Leu
        115                 120                 125

Ile Ala Ser His Thr Ala Phe Ala Ala Lys Ala Gly Leu Met Arg His
    130                 135                 140

Thr Ile Gly Gln Ala Glu Gln Gln Ala Met Ser Ala Gln Ala Phe His
145                 150                 155                 160

Gln Gly Glu Ser Ala Ala Ala Phe Gln Gly Ala His Ala Arg Phe Val
                165                 170                 175

Ala Ala Ala Ala Lys Val Asn Thr Leu Leu Asp Ile Ala Gln Ala Asn
            180                 185                 190

Leu Gly Glu Ala Ala Gly Thr Tyr Val Ala Ala Asp Ala Ala Ala Ala
        195                 200                 205

Ser Ser Tyr Thr Gly Phe Arg Gly Arg Lys Arg Arg Thr Ser Arg
    210                 215                 220
```

```
Phe Met Thr Asp Pro His Ala Met Arg Asp Met Ala Gly Arg Phe Glu
225                 230                 235                 240

Val His Ala Gln Thr Val Glu Asp Glu Ala Arg Arg Met Trp Ala Ser
                245                 250                 255

Ala Gln Asn Ile Ala Gly Ala Gly Trp Ser Gly Met Ala Glu Ala Thr
            260                 265                 270

Ser Leu Asp Thr Met Thr Gln Met Asn Gln Ala Phe Arg Asn Ile Val
        275                 280                 285

Asn Met Leu His Gly Val Arg Asp Gly Leu Val Arg Asp Ala Asn Asn
    290                 295                 300

Tyr Glu Gln Gln Glu Gln Ala Ser Gln Gln Ile Leu Ser Ser Tyr Pro
305                 310                 315                 320

Tyr Asp Val Pro Asp Tyr Ala
                325

<210> SEQ ID NO 3
<211> LENGTH: 1071
<212> TYPE: DNA
<213> ORGANISM: Artificial Sequence
<220> FEATURE:
<223> OTHER INFORMATION: pDQE nucleic acid

<400> SEQUENCE: 3
atggactgga catggattct gttcctcgtc gccgccgcaa ctagagtgca ttccgccgat        60
acaattcagg tcacccctca gatgctgagg tctaccgcaa atgacatcca ggccaacatg       120
gagcaggcta tggggattgc aaagggttac ctggccaacc aggaaaatgt gatgaacccc       180
gctacttgga gcgggaccgg tgtggtcgct tcccacatga ctgcaaccga gatcactaat       240
gaactgaaca agtgctcac cggcggaaca agactggcag agggactcgt ccaggcagct       300
gcactgatgg agggtcacga agccgatagc cagaccgcat ccaggcccct ctttggcgct       360
tcacatggga gccgcggtcg aaagaggaga agctcccagt ccatgtactc ttatccagct       420
atgacagcaa atgtgggcga catggccggc tacactggaa ccacacagtc tctgggagcc       480
gatattgcta gtgagcgaac cgcacccctca agggcttgcc aggggaccct gggtatgagt       540
caccaggatt ggcaggccca gtggaaccag gctatggagg ccctggctcg gcatatcgg       600 cgctgccgaa gggccctgcg acagatcggg gtgctcgaac gacctgtcgg ggactctagt       660
gattgtggta caattcgggt gggctcattc aggggaagat ggctggaccc ccgacatgca       720
ggacctgcaa ccgcagctga cgccggcgat cggggacgca aaagacggag tgacccaaca       780
gtgctggccg atgctgtcgc aagaatggcc gagtttggac ggcacgtgga ggaactcgtc       840
gctgagatcg aatccctggt gacaaggctc catgtcacat ggactggaga gggagcagca       900
gctcacgcag aagctcagag gcattgggca gccggcgaag ccatgatgag acaggcactg       960
gcacagctca ctgctgcagg acagtccgct catgcaaatt atgccggagc tatggctact      1020
aatctcggaa tgtggtccta tccttacgac gtgcctgact acgcataatg a              1071

<210> SEQ ID NO 4
<211> LENGTH: 355
<212> TYPE: PRT
<213> ORGANISM: Artificial Sequence
<220> FEATURE:
<223> OTHER INFORMATION: pDQE amino acid sequence
```

<400> SEQUENCE: 4

Met Asp Trp Thr Trp Ile Leu Phe Leu Val Ala Ala Ala Thr Arg Val
1               5                   10                  15

His Ser Ala Asp Thr Ile Gln Val Thr Pro Gln Met Leu Arg Ser Thr
            20                  25                  30

Ala Asn Asp Ile Gln Ala Asn Met Glu Gln Ala Met Gly Ile Ala Lys
        35                  40                  45

Gly Tyr Leu Ala Asn Gln Glu Asn Val Met Asn Pro Ala Thr Trp Ser
50                  55                  60

Gly Thr Gly Val Val Ala Ser His Met Thr Ala Thr Glu Ile Thr Asn
65                  70                  75                  80

Glu Leu Asn Lys Val Leu Thr Gly Gly Thr Arg Leu Ala Glu Gly Leu
                85                  90                  95

Val Gln Ala Ala Ala Leu Met Glu Gly His Glu Ala Asp Ser Gln Thr
            100                 105                 110

Ala Phe Gln Ala Leu Phe Gly Ala Ser His Gly Ser Arg Gly Arg Lys
        115                 120                 125

Arg Arg Ser Ser Gln Ser Met Tyr Ser Tyr Pro Ala Met Thr Ala Asn
130                 135                 140

Val Gly Asp Met Ala Gly Tyr Thr Gly Thr Thr Gln Ser Leu Gly Ala
145                 150                 155                 160

Asp Ile Ala Ser Glu Arg Thr Ala Pro Ser Arg Ala Cys Gln Gly Asp
                165                 170                 175

Leu Gly Met Ser His Gln Asp Trp Gln Ala Gln Trp Asn Gln Ala Met
            180                 185                 190

Glu Ala Leu Ala Arg Ala Tyr Arg Arg Cys Arg Arg Ala Leu Arg Gln
        195                 200                 205

Ile Gly Val Leu Glu Arg Pro Val Gly Asp Ser Ser Asp Cys Gly Thr
210                 215                 220

Ile Arg Val Gly Ser Phe Arg Gly Arg Trp Leu Asp Pro Arg His Ala
225                 230                 235                 240

Gly Pro Ala Thr Ala Ala Asp Ala Gly Asp Arg Gly Arg Lys Arg Arg
                245                 250                 255

Ser Asp Pro Thr Val Leu Ala Asp Ala Val Ala Arg Met Ala Glu Phe
            260                 265                 270

Gly Arg His Val Glu Glu Leu Val Ala Glu Ile Glu Ser Leu Val Thr
        275                 280                 285

Arg Leu His Val Thr Trp Thr Gly Glu Gly Ala Ala Ala His Ala Glu
290                 295                 300

Ala Gln Arg His Trp Ala Ala Gly Glu Ala Met Met Arg Gln Ala Leu
305                 310                 315                 320

Ala Gln Leu Thr Ala Ala Gly Gln Ser Ala His Ala Asn Tyr Ala Gly
                325                 330                 335

Ala Met Ala Thr Asn Leu Gly Met Trp Ser Tyr Pro Tyr Asp Val Pro
            340                 345                 350

Asp Tyr Ala
        355

<210> SEQ ID NO 5
<211> LENGTH: 993
<212> TYPE: DNA
<213> ORGANISM: Artificial Sequence
<220> FEATURE:
<223> OTHER INFORMATION: pHAT nucleic acid

<400> SEQUENCE: 5

```
atggactgga cctggattct cttcctggtc gccgccgcaa cccgcgtgca ctcatctcag    60
attatgtaca actaccccgc aatgctcgga cacgcaggag acatggcagg atacgcaggt   120
accctgcaga gcctcggagc tgagattgca gtggaacagg ccgctctgca gtccgcctgg   180
cagggcgaca caggaatcac ttaccaggcc tggcaggctc agtggaacca ggctatggag   240
gatctggtca gagcatatca cgccatgagc tccacccatg aggccaatac aatggctatg   300
atggcacggg atacagctga agcagccaag tggggcggac gagggaggaa aaggagatct   360
actgagcagc agtggaactt tgccggcatc gaagctgcag ccagtgccat tcagggaaat   420
gtggcttcaa tccacagcct gctcgacgag ggaaagcagt ccctgaccaa actcgctgca   480
gcatggggcg gcagcggcag tgaggcatac agggagtcc agcagaagtg ggatgcaact   540
gccaccgaac tgaacaatgc actgcagaac ctcgcccgca ctattagtga ggccgggcag   600
gctatggcat caaccgaagg gaatgtggcc ggcatgttcg ctagaggtcg aaacggcgc    660
tccaacgcag accccgtgct gtcttacaac ttcgatgcta tcgagtactc tgtccgccag   720
gaaatccata ccacagctgc acgattcaac gccgctctgc aggagctcag gagccagatc   780
gcccctctgc agcagctctg gacacgcgag gcagcagctg catatcacgc cgaacagctg   840
aagtggcatc aggccgctag cgccctgaac gaaatcctga ttgacctcgg aatgctgtg    900
cgacacggtg cagacgatgt cgcccatgct gatcgccgcg ccgccggtgc ctgggctagg   960
tatccctacg atgtccccga ttacgcataa tga                                993
```

<210> SEQ ID NO 6
<211> LENGTH: 329
<212> TYPE: PRT
<213> ORGANISM: Artificial Sequence
<220> FEATURE:
<223> OTHER INFORMATION: pHAT amino acid sequence

<400> SEQUENCE: 6

```
Met Asp Trp Thr Trp Ile Leu Phe Leu Val Ala Ala Ala Thr Arg Val
1               5                   10                  15

His Ser Ser Gln Ile Met Tyr Asn Tyr Pro Ala Met Leu Gly His Ala
            20                  25                  30

Gly Asp Met Ala Gly Tyr Ala Gly Thr Leu Gln Ser Leu Gly Ala Glu
        35                  40                  45

Ile Ala Val Glu Gln Ala Ala Leu Gln Ser Ala Trp Gln Gly Asp Thr
    50                  55                  60

Gly Ile Thr Tyr Gln Ala Trp Gln Ala Gln Trp Asn Gln Ala Met Glu
65                  70                  75                  80

Asp Leu Val Arg Ala Tyr His Ala Met Ser Ser Thr His Glu Ala Asn
                85                  90                  95

Thr Met Ala Met Met Ala Arg Asp Thr Ala Glu Ala Ala Lys Trp Gly
            100                 105                 110

Gly Arg Gly Arg Lys Arg Arg Ser Thr Glu Gln Gln Trp Asn Phe Ala
        115                 120                 125

Gly Ile Glu Ala Ala Ala Ser Ala Ile Gln Gly Asn Val Ala Ser Ile
    130                 135                 140

His Ser Leu Leu Asp Glu Gly Lys Gln Ser Leu Thr Lys Leu Ala Ala
145                 150                 155                 160

Ala Trp Gly Gly Ser Gly Ser Glu Ala Tyr Gln Gly Val Gln Gln Lys
                165                 170                 175
```

Trp Asp Ala Thr Ala Thr Glu Leu Asn Asn Ala Leu Gln Leu Ala
            180                 185                 190

Arg Thr Ile Ser Glu Ala Gly Gln Ala Met Ala Ser Thr Glu Gly Asn
        195                 200                 205

Val Ala Gly Met Phe Ala Arg Gly Arg Lys Arg Arg Ser Asn Ala Asp
    210                 215                 220

Pro Val Leu Ser Tyr Asn Phe Asp Ala Ile Glu Tyr Ser Val Arg Gln
225                 230                 235                 240

Glu Ile His Thr Thr Ala Ala Arg Phe Asn Ala Ala Leu Gln Glu Leu
                245                 250                 255

Arg Ser Gln Ile Ala Pro Leu Gln Gln Leu Trp Thr Arg Glu Ala Ala
            260                 265                 270

Ala Ala Tyr His Ala Glu Gln Leu Lys Trp His Gln Ala Ala Ser Ala
        275                 280                 285

Leu Asn Glu Ile Leu Ile Asp Leu Gly Asn Ala Val Arg His Gly Ala
    290                 295                 300

Asp Asp Val Ala His Ala Asp Arg Arg Ala Ala Gly Ala Trp Ala Arg
305                 310                 315                 320

Tyr Pro Tyr Asp Val Pro Asp Tyr Ala
                325

<210> SEQ ID NO 7
<211> LENGTH: 1080
<212> TYPE: DNA
<213> ORGANISM: Artificial Sequence
<220> FEATURE:
<223> OTHER INFORMATION: pBCU nucleic acid sequence

<400> SEQUENCE: 7
atggactgga cctggattct cttcctggtg gctgccgcaa cacgggtgca ctctgccgaa    60
atgaaaactg atgccgcaac tctggctcag gaggccggga acttcgaacg catctccggt   120
gacctcaaga cacagattga tcaggtggag tcaactgcag ggagcctgca gggccagtgg   180
cgaggggccg ctggtacagc agcacaggct gcagtggtca ggtttcagga agccgctaac   240
aagcagaaac aggagctgga cgaaatctcc actaatattc ggcaggctgg agtgcagtac   300
tctcgcgccg atgaggaaca gcagcaggct ctgagctccc agatgggctt ccgaggaagg   360
aagaggagat ctagtgacca gattacatac aaccccgggg ccgtgagcga ctttgcatct   420
gatgtcggca gtagggccgg acagctccac atgatctatg aggacactgc cagtaaaacc   480
aatgctctgc aggaattctt tgccggccat ggagctcagg gcttctttga tgcccaggct   540
cagatgctgt ccgggctcca gggtctgatt gagactgtgg ccagcacgg aaccacaact   600 ggccatgtcc tcgacaacgc catcggaacc gatcaggcaa ttgccgggct gttcagaggt   660
cggaaacggc gctctgtgga gccaggaagg atcggcggaa atcaggccag actggcagcc   720
gtgctgctcg acgtgagcac ccccaacaca ctcaatgctg actttgatct gatgagatca   780
gtggcaggca tcaccgatgc ccgcaatgag gaaattcgag caatgctcca ggccttcatc   840
ggccggatgt caggagtgcc ccctagcgtg tggggcggcc tggctgcagc ccggtttcag   900
gacgtggtcg atcgctggaa cgccgagagc acccgactct atcacgtgct gcatgctatc   960
gcagacacaa ttaggcacaa tgaggctgca ctgagagaag ctggacagat ccatgcaaga  1020
catattgccg ccgccggtgg tgacctgtac ccatacgatg tccccgatta cgcttgataa  1080

```
<210> SEQ ID NO 8
<211> LENGTH: 358
<212> TYPE: PRT
<213> ORGANISM: Artificial Sequence
<220> FEATURE:
<223> OTHER INFORMATION: pBCU amino acid sequence

<400> SEQUENCE: 8

Met Asp Trp Thr Trp Ile Leu Phe Leu Val Ala Ala Thr Arg Val
1               5                   10                  15

His Ser Ala Glu Met Lys Thr Asp Ala Thr Leu Ala Gln Glu Ala
                20                  25                  30

Gly Asn Phe Glu Arg Ile Ser Gly Asp Leu Lys Thr Gln Ile Asp Gln
            35                  40                      45

Val Glu Ser Thr Ala Gly Ser Leu Gln Gly Gln Trp Arg Gly Ala Ala
50                      55                      60

Gly Thr Ala Ala Gln Ala Ala Val Val Arg Phe Gln Glu Ala Ala Asn
65                      70                      75                      80

Lys Gln Lys Gln Glu Leu Asp Glu Ile Ser Thr Asn Ile Arg Gln Ala
                    85                      90                      95

Gly Val Gln Tyr Ser Arg Ala Asp Glu Glu Gln Gln Gln Ala Leu Ser
                100                     105                     110

Ser Gln Met Gly Phe Arg Gly Arg Lys Arg Arg Ser Ser Asp Gln Ile
            115                     120                     125

Thr Tyr Asn Pro Gly Ala Val Ser Asp Phe Ala Ser Asp Val Gly Ser
130                     135                     140

Arg Ala Gly Gln Leu His Met Ile Tyr Glu Asp Thr Ala Ser Lys Thr
145                     150                     155                     160

Asn Ala Leu Gln Glu Phe Phe Ala Gly His Gly Ala Gln Gly Phe Phe
                    165                     170                     175

Asp Ala Gln Ala Gln Met Leu Ser Gly Leu Gln Gly Leu Ile Glu Thr
                180                     185                     190

Val Gly Gln His Gly Thr Thr Thr Gly His Val Leu Asp Asn Ala Ile
            195                     200                     205

Gly Thr Asp Gln Ala Ile Ala Gly Leu Phe Arg Gly Arg Lys Arg Arg
210                     215                     220

Ser Val Glu Pro Gly Arg Ile Gly Gly Asn Gln Ala Arg Leu Ala Ala
225                     230                     235                     240

Val Leu Leu Asp Val Ser Thr Pro Asn Thr Leu Asn Ala Asp Phe Asp
                    245                     250                     255

Leu Met Arg Ser Val Ala Gly Ile Thr Asp Ala Arg Asn Glu Glu Ile
                260                     265                     270

Arg Ala Met Leu Gln Ala Phe Ile Gly Arg Met Ser Gly Val Pro Pro
            275                     280                     285

Ser Val Trp Gly Gly Leu Ala Ala Ala Arg Phe Gln Asp Val Val Asp
290                     295                     300

Arg Trp Asn Ala Glu Ser Thr Arg Leu Tyr His Val Leu His Ala Ile
305                     310                     315                     320

Ala Asp Thr Ile Arg His Asn Glu Ala Ala Leu Arg Glu Ala Gly Gln
                    325                     330                     335

Ile His Ala Arg His Ile Ala Ala Gly Gly Asp Leu Tyr Pro Tyr
                340                     345                     350

Asp Val Pro Asp Tyr Ala
            355
```

<210> SEQ ID NO 9
<211> LENGTH: 999
<212> TYPE: DNA
<213> ORGANISM: Artificial Sequence
<220> FEATURE:
<223> OTHER INFORMATION: pORF nucleic acid sequence

<400> SEQUENCE: 9

```
atggactgga cctggattct cttcctggtc gccgccgcaa cacgggtgca ttcaacaatc    60
aattatcagt ttggggacgt ggacgcccac ggagcaatga tccgagcaca ggctggtctg   120
ctggaggcag aacatcaggc tattgtgcga gacgtgctgg cagctggcga tttctggggc   180
ggagcaggca gcgtggcatg ccaggagttc atcacacagc tgggccgaaa ctttcaggtc   240
atctacgaac aggcaaatgc acacggacag aaggtccagg cagccggtaa caatatggcc   300
cagactgact ctgctgtggg cagctcctgg gcccgaggaa ggaaaaggag atctagtcag   360
atcatgtaca actatcccgc catgatggct catgcaggag acatggccgg gtatgctggt   420
accctgcaga gcctcggggc agatatcgca tccgagcagg ccgtgctgag cagcgcctgg   480
cagggcgaca ccggaattac ataccagggc tggcagacac agtggaacca ggccctggaa   540
gatctcgtcc gggcttatca gtccatgtct ggcactcacg agagcaatac catggctatg   600
ctggcacgcg atggagccga agctgcaaag tggggcggca gaggacgaaa acggcgctca   660
ggtgcagaca taccctgcg agtggagcct gctgtcatgc agggctttgc cgctagtctg   720
gacggagcag ccgagcacct cgctgtgcag ctggcagaac tcgatgcaca ggtcggacag   780
atgctgggcg atggaggggg cgccagtggt tcagcatacg gatctgcctg ggagctggct   840
catagagggg caggtgaagt gcagctgggc ctcagtatgc tcgctgcagc aattgcacac   900
gctggagcag gatatcagca taatgaggct gcatccgccc aggtgctcag agaggtcggt   960
ggtggatacc catacgatgt ccccgattac gcttgataa                          999
```

<210> SEQ ID NO 10
<211> LENGTH: 331
<212> TYPE: PRT
<213> ORGANISM: Artificial Sequence
<220> FEATURE:
<223> OTHER INFORMATION: pORF amino acid sequence

<400> SEQUENCE: 10

Met Asp Trp Thr Trp Ile Leu Phe Leu Val Ala Ala Ala Thr Arg Val
1               5                   10                  15

His Ser Thr Ile Asn Tyr Gln Phe Gly Asp Val Asp Ala His Gly Ala
            20                  25                  30

Met Ile Arg Ala Gln Ala Gly Leu Leu Glu Ala Glu His Gln Ala Ile
        35                  40                  45

Val Arg Asp Val Leu Ala Ala Gly Asp Phe Trp Gly Gly Ala Gly Ser
    50                  55                  60

Val Ala Cys Gln Glu Phe Ile Thr Gln Leu Gly Arg Asn Phe Gln Val
65                  70                  75                  80

Ile Tyr Glu Gln Ala Asn Ala His Gly Gln Lys Val Gln Ala Ala Gly
                85                  90                  95

Asn Asn Met Ala Gln Thr Asp Ser Ala Val Gly Ser Ser Trp Ala Arg
            100                 105                 110

Gly Arg Lys Arg Arg Ser Ser Gln Ile Met Tyr Asn Tyr Pro Ala Met
        115                 120                 125

Met Ala His Ala Gly Asp Met Ala Gly Tyr Ala Gly Thr Leu Gln Ser
    130                 135                 140

```
Leu Gly Ala Asp Ile Ala Ser Glu Gln Ala Val Leu Ser Ser Ala Trp
145                 150                 155                 160

Gln Gly Asp Thr Gly Ile Thr Tyr Gln Gly Trp Gln Thr Gln Trp Asn
            165                 170                 175

Gln Ala Leu Glu Asp Leu Val Arg Ala Tyr Gln Ser Met Ser Gly Thr
        180                 185                 190

His Glu Ser Asn Thr Met Ala Met Leu Ala Arg Asp Gly Ala Glu Ala
    195                 200                 205

Ala Lys Trp Gly Gly Arg Gly Arg Lys Arg Arg Ser Gly Ala Asp Asp
210                 215                 220

Thr Leu Arg Val Glu Pro Ala Val Met Gln Gly Phe Ala Ala Ser Leu
225                 230                 235                 240

Asp Gly Ala Ala Glu His Leu Ala Val Gln Leu Ala Glu Leu Asp Ala
            245                 250                 255

Gln Val Gly Gln Met Leu Gly Gly Trp Arg Gly Ala Ser Gly Ser Ala
        260                 265                 270

Tyr Gly Ser Ala Trp Glu Leu Ala His Arg Gly Ala Gly Glu Val Gln
    275                 280                 285

Leu Gly Leu Ser Met Leu Ala Ala Ala Ile Ala His Ala Gly Ala Gly
290                 295                 300

Tyr Gln His Asn Glu Ala Ala Ser Ala Gln Val Leu Arg Glu Val Gly
305                 310                 315                 320

Gly Gly Tyr Pro Tyr Asp Val Pro Asp Tyr Ala
            325                 330

<210> SEQ ID NO 11
<211> LENGTH: 1329
<212> TYPE: DNA
<213> ORGANISM: Artificial Sequence
<220> FEATURE:
<223> OTHER INFORMATION: BE6 nucleic acid sequence

<400> SEQUENCE: 11
atggactgga cttggattct cttcctggtc gcagcagcaa cacgagtgca ttctaccgat      60
gtctcacgaa aaattagggc ttggggtagg agactgatga ttggaaccgc agctgcagtg     120
gtcctgccag gactcgtggg actggcagga ggagccgcta cagctggcgc attcagccgc     180
cctggactgc cagtggagta cctccaggtc caagcccatc catgggacga agatatcaag     240
gtgcagtttc agtccggggg taacaatgcc ccgctgtgtc tacctgctcga tggcctgcgg     300 gctcaggacg attataatgg atgggacatt aacacccctg ccttcgaatg gtactatcag     360
tccggcctgt ctatcgtgat gcctgtcggc ggacagagct cctttttacag cgactggtat     420 tccccagcct gcggcaaggc tggctgtcag acttataaat gggagacttt cctcacctcc     480
gaactgccac agtggctctc tgccaatagg gctgtgaaac ccaccggatc tgcagccatt     540
gggctgagta tggcaggttc tagtgccatg attctggctg cataccaccc tcagcagttt     600
atctatgccg atctctgag tgctctgctc gatccttcac aggggatggg tccaagcctc     660
atcggactgg ctatggggga cgcagggggt acaaggccg ctgacatgtg ggggccctca     720
agcgatcctg cttgggagag aaacgaccca acacagcaga ttcccaaact ggtgcaaac     780 aatgcccggc tctgggtcta ttgcggcaac ggagccccca tgaactggg cggagccaat     840 atccctgctg agttcctgga aaattttgtg aggtcctcta acctgaagtt ccaggatgct     900
tacaacgcag ccggggtca acgccgtc ttcaatttc ccctaacgg cgctcattct     960 gcagagtatt ggggagcaca gctgaacgcc atgaaggggg acctgcagag ttcactcgga    1020
```

```
gctggtcgag gaaggaaacg acgatctaca gagcagcagt ggaattttgc cgggatcgaa    1080
gctgcagcca gcgctattca gggcaacgtg gccagtatcc attcactgct cgatgagggc    1140
aagcagagcc tcactaaact ggctgcagca tggggaggat cagggagcga ggcataccag    1200
ggtgtgcagc agaagtggga cgcaaccgcc acagaactga acaatgcact ccagaatctg    1260
gccagaacaa tcagtgaggc cggccaggct atggcatcca ctgagggtaa cgtggctggc    1320
atgttcgca                                                            1329
```

<210> SEQ ID NO 12
<211> LENGTH: 443
<212> TYPE: PRT
<213> ORGANISM: Artificial Sequence
<220> FEATURE:
<223> OTHER INFORMATION: BE6 amino acid sequence

<400> SEQUENCE: 12

```
Met Asp Trp Thr Trp Ile Leu Phe Leu Val Ala Ala Thr Arg Val
1               5                   10                  15

His Ser Thr Asp Val Ser Arg Lys Ile Arg Ala Trp Gly Arg Leu
                20                  25                  30

Met Ile Gly Thr Ala Ala Ala Val Val Leu Pro Gly Leu Val Gly Leu
                35                  40                  45

Ala Gly Gly Ala Ala Thr Ala Gly Ala Phe Ser Arg Pro Gly Leu Pro
        50                  55                  60

Val Glu Tyr Leu Gln Val Pro Ser Pro Ser Met Gly Arg Asp Ile Lys
65                  70                  75                  80

Val Gln Phe Gln Ser Gly Gly Asn Asn Ala Pro Ala Val Tyr Leu Leu
                85                  90                  95

Asp Gly Leu Arg Ala Gln Asp Asp Tyr Asn Gly Trp Asp Ile Asn Thr
                100                 105                 110

Pro Ala Phe Glu Trp Tyr Tyr Gln Ser Gly Leu Ser Ile Val Met Pro
            115                 120                 125

Val Gly Gly Gln Ser Ser Phe Tyr Ser Asp Trp Tyr Ser Pro Ala Cys
    130                 135                 140

Gly Lys Ala Gly Cys Gln Thr Tyr Lys Trp Glu Thr Phe Leu Thr Ser
145                 150                 155                 160

Glu Leu Pro Gln Trp Leu Ser Ala Asn Arg Ala Val Lys Pro Thr Gly
                165                 170                 175

Ser Ala Ala Ile Gly Leu Ser Met Ala Gly Ser Ala Met Ile Leu
            180                 185                 190

Ala Ala Tyr His Pro Gln Gln Phe Ile Tyr Ala Gly Ser Leu Ser Ala
        195                 200                 205

Leu Leu Asp Pro Ser Gln Gly Met Gly Pro Ser Leu Ile Gly Leu Ala
    210                 215                 220

Met Gly Asp Ala Gly Gly Tyr Lys Ala Ala Asp Met Trp Gly Pro Ser
225                 230                 235                 240

Ser Asp Pro Ala Trp Glu Arg Asn Asp Pro Thr Gln Gln Ile Pro Lys
                245                 250                 255

Leu Val Ala Asn Asn Ala Arg Leu Trp Val Tyr Cys Gly Asn Gly Ala
            260                 265                 270

Pro Asn Glu Leu Gly Gly Ala Asn Ile Pro Ala Glu Phe Leu Glu Asn
        275                 280                 285

Phe Val Arg Ser Ser Asn Leu Lys Phe Gln Asp Ala Tyr Asn Ala Ala
    290                 295                 300
```

| | | | | | | | | | | | | |
|---|---|---|---|---|---|---|---|---|---|---|---|---|
|Gly|Gly|His|Asn|Ala|Val|Phe|Asn|Phe|Pro|Pro|Asn|Gly|Ala|His|Ser|
|305| | | |310| | | |315| | | |320|
|Ala|Glu|Tyr|Trp|Gly|Ala|Gln|Leu|Asn|Ala|Met|Lys|Gly|Asp|Leu|Gln|
| | | | |325| | | |330| | | |335|
|Ser|Ser|Leu|Gly|Ala|Gly|Arg|Gly|Arg|Lys|Arg|Ser|Thr|Glu|Gln|
| | | |340| | | |345| | | |350|
|Gln|Trp|Asn|Phe|Ala|Gly|Ile|Glu|Ala|Ala|Ser|Ala|Ile|Gln|Gly|
| | | |355| | | |360| | | |365|
|Asn|Val|Ala|Ser|Ile|His|Ser|Leu|Leu|Asp|Glu|Gly|Lys|Gln|Ser|Leu|
| | | |370| | | |375| | | |380|
|Thr|Lys|Leu|Ala|Ala|Ala|Trp|Gly|Gly|Ser|Gly|Ser|Glu|Ala|Tyr|Gln|
|385| | | |390| | | |395| | | |400|
|Gly|Val|Gln|Gln|Lys|Trp|Asp|Ala|Thr|Ala|Thr|Glu|Leu|Asn|Asn|Ala|
| | | |405| | | |410| | | |415|
|Leu|Gln|Asn|Leu|Ala|Arg|Thr|Ile|Ser|Glu|Ala|Gly|Gln|Ala|Met|Ala|
| | | |420| | | |425| | | |430|
|Ser|Thr|Glu|Gly|Asn|Val|Ala|Gly|Met|Phe|Ala|
| | | |435| | | |440|

<210> SEQ ID NO 13
<211> LENGTH: 1368
<212> TYPE: DNA
<213> ORGANISM: Artificial Sequence
<220> FEATURE:
<223> OTHER INFORMATION: AE6 nucleic acid sequence

<400> SEQUENCE: 13

```
atggattgga catggattct gtttctcgtc gcagcagcca caagagtgca tagccagctc      60
gtcgatagag tgaggggggc agtgactggc atgtctagga gactggtggt cggagctgtg     120
ggagcagctc tggtcagtgg tctcgtggga gcagtcggag gaaccgctac agcaggagcc     180
ttctctcgcc ctgggctccc agtggagtac ctgcaggtcc cctcacctag catgggccga     240
gatattaagg tgcagtttca gtcaggggt gctaacagcc cagcactgta cctgctcgac     300
ggactgcgag ctcaggacga tttctccgga tgggatatca atacacctgc ctttgaatgg     360
tatgaccaga gtggcctgtc agtggtcatg cctgtgggcg acagagctc cttctacagt     420
gattggtatc agccagcctg cggaaaggct gggtgtcaga cttataaatg ggagacattt     480
ctgacttccg aactcccagg atggctgcag gctaaccgcc acgtgaaacc cacaggttcc     540
gcagtggtcg gcctgtctat ggcagcctct agtgcactga ctctcgccat ctaccatcca     600
cagcagttcg tctatgctgg agcaatgagt gggctgctcg atccatcaca ggcaatggga     660
ccaaccctga tcgtctcgc tatgggcgac gcaggggggtt acaaggctag cgacatgtgg     720
ggacccaaag aggaccccgc ctggcagaga aacgaccccc tgctcaatgt ggggaagctg     780
attgctaaca atgcacgggt gtgggtctat tgcggtaacg gcaagccttc cgatctcggc     840
ggaaacaatc tgccagccaa attcctggag ggctttgtga ggacctctaa catcaagttc     900
caggacgcct acaacgctgg gggtggccac aatggtgtct tcgactttcc cgattctgga     960
acacatagtg ccgaatattg gggggccag ctgaacgcta tgaaaccga cctccagaga    1020
gcactgggtg ccaccctaa tacaggacca gcaccacagg gtgcccgagg caggaagcga    1080
cgatcaactg agcagcagtg gaactttgcc gggatcgaag ctgcagccag cgcaattcag    1140
ggcaatgtgg ccagcatcca ctccctgctc gatgaggga agcagagcct gaccaaactc    1200
gctgcagcct ggggagggtc cggatctgag gcttaccagg gggtgcagca gaagtgggac    1260
```

```
gccactgcta ccgaactgaa caatgccctg cagaacctcg ctcggactat tagcgaggca    1320
ggacaggcaa tggcatccac cgaaggaaat gtggctggga tgtttgca                  1368
```

<210> SEQ ID NO 14
<211> LENGTH: 456
<212> TYPE: PRT
<213> ORGANISM: Artificial Sequence
<220> FEATURE:
<223> OTHER INFORMATION: AE6 amino acid sequence

<400> SEQUENCE: 14

```
Met Asp Trp Thr Trp Ile Leu Phe Leu Val Ala Ala Thr Arg Val
1               5                  10                  15

His Ser Gln Leu Val Asp Arg Val Arg Gly Ala Val Thr Gly Met Ser
            20                  25                  30

Arg Arg Leu Val Val Gly Ala Val Gly Ala Ala Leu Val Ser Gly Leu
        35                  40                  45

Val Gly Ala Val Gly Gly Thr Ala Thr Ala Gly Ala Phe Ser Arg Pro
    50                  55                  60

Gly Leu Pro Val Glu Tyr Leu Gln Val Pro Ser Pro Ser Met Gly Arg
65                  70                  75                  80

Asp Ile Lys Val Gln Phe Gln Ser Gly Gly Ala Asn Ser Pro Ala Leu
                85                  90                  95

Tyr Leu Leu Asp Gly Leu Arg Ala Gln Asp Asp Phe Ser Gly Trp Asp
            100                 105                 110

Ile Asn Thr Pro Ala Phe Glu Trp Tyr Asp Gln Ser Gly Leu Ser Val
        115                 120                 125

Val Met Pro Val Gly Gly Gln Ser Ser Phe Tyr Ser Asp Trp Tyr Gln
    130                 135                 140

Pro Ala Cys Gly Lys Ala Gly Cys Gln Thr Tyr Lys Trp Glu Thr Phe
145                 150                 155                 160

Leu Thr Ser Glu Leu Pro Gly Trp Leu Gln Ala Asn Arg His Val Lys
                165                 170                 175

Pro Thr Gly Ser Ala Val Val Gly Leu Ser Met Ala Ala Ser Ser Ala
            180                 185                 190

Leu Thr Leu Ala Ile Tyr His Pro Gln Gln Phe Val Tyr Ala Gly Ala
        195                 200                 205

Met Ser Gly Leu Leu Asp Pro Ser Gln Ala Met Gly Pro Thr Leu Ile
    210                 215                 220

Gly Leu Ala Met Gly Asp Ala Gly Gly Tyr Lys Ala Ser Asp Met Trp
225                 230                 235                 240

Gly Pro Lys Glu Asp Pro Ala Trp Gln Arg Asn Asp Pro Leu Leu Asn
                245                 250                 255

Val Gly Lys Leu Ile Ala Asn Asn Ala Arg Val Trp Val Tyr Cys Gly
            260                 265                 270

Asn Gly Lys Pro Ser Asp Leu Gly Gly Asn Asn Leu Pro Ala Lys Phe
        275                 280                 285

Leu Glu Gly Phe Val Arg Thr Ser Asn Ile Lys Phe Gln Asp Ala Tyr
    290                 295                 300

Asn Ala Gly Gly Gly His Asn Gly Val Phe Asp Phe Pro Asp Ser Gly
305                 310                 315                 320

Thr His Ser Ala Glu Tyr Trp Gly Ala Gln Leu Asn Ala Met Lys Pro
                325                 330                 335

Asp Leu Gln Arg Ala Leu Gly Ala Thr Pro Asn Thr Gly Pro Ala Pro
            340                 345                 350
```

```
Gln Gly Ala Arg Gly Arg Lys Arg Arg Ser Thr Glu Gln Gln Trp Asn
            355                 360                 365
Phe Ala Gly Ile Glu Ala Ala Ala Ser Ala Ile Gln Gly Asn Val Ala
        370                 375                 380
Ser Ile His Ser Leu Leu Asp Glu Gly Lys Gln Ser Leu Thr Lys Leu
385                 390                 395                 400
Ala Ala Ala Trp Gly Ser Gly Ser Glu Ala Tyr Gln Gly Val Gln
                405                 410                 415
Gln Lys Trp Asp Ala Thr Ala Thr Glu Leu Asn Asn Ala Leu Gln Asn
            420                 425                 430
Leu Ala Arg Thr Ile Ser Glu Ala Gly Gln Ala Met Ala Ser Thr Glu
        435                 440                 445
Gly Asn Val Ala Gly Met Phe Ala
    450                 455

<210> SEQ ID NO 15
<211> LENGTH: 942
<212> TYPE: DNA
<213> ORGANISM: Artificial Sequence
<220> FEATURE:
<223> OTHER INFORMATION: TE6 nucleic acid sequence

<400> SEQUENCE: 15
atggattgga cttggattct ctttctcgtc gcagcagcaa cccgcgtgca tagcacagag       60
cagcagtgga acttcgccgg tattgaagcc gctgcatctg ccatccaggg gaacgtggct      120
tccattcact ctctgctcga cgagggcaag cagagtctga ccaaactcgc agctgcatgg      180
ggaggaagcg gctccgaggc ataccaggga gtccagcaga agtgggatgc caccgctaca      240
gaactgaaca atgccctgca gaacctcgct cgcaccatct ctgaggctgg ccaggcaatg      300
gccagtacag aagggaatgt ggccggcatg ttcgccaggg gcaggaaaag gagaagtacc      360
gagcagcagt ggaactttgc cgggatcgaa gccgctgcat cagcaattca gggtaatgtg      420
gctagtatcc attcactcct ggacgagggc aagcagagcc tgacaaaact cgccgctgca      480
tggggggggtt ctgggagtga ggcctatcag ggtgtgcagc agaaatggga tgctactgca      540
accgaactga acaatgcact gcagaacctc gcccgaacta tttcagaggc tgggcaggcc      600
atggctagca ccgaaggcaa tgtcgcagga atgttcgcca gaggccggaa acggcgcagc      660
actgaacagc agtggaattt tgccggcatt gaagccgctg catccgccat ccagggaaat      720
gtggctagca ttcactcccct gctcgacgag ggaaagcagt ccctgacaaa gctggccgcc      780
gcatggggag gatcaggcag cgaagcctat cagggcgtgc agcagaaatg gacgcaaca      840
gccactgaac tgaacaatgc tctgcagaac ctggcacgaa caatctccga ggcaggacag      900
gctatggcat ctactgaagg gaatgtggct ggcatgttcg ca                         942

<210> SEQ ID NO 16
<211> LENGTH: 314
<212> TYPE: PRT
<213> ORGANISM: Artificial Sequence
<220> FEATURE:
<223> OTHER INFORMATION: TE6 amino acid sequence

<400> SEQUENCE: 16

Met Asp Trp Thr Trp Ile Leu Phe Leu Val Ala Ala Ala Thr Arg Val
1               5                   10                  15
His Ser Thr Glu Gln Gln Trp Asn Phe Ala Gly Ile Glu Ala Ala Ala
            20                  25                  30
```

Ser Ala Ile Gln Gly Asn Val Ala Ser Ile His Ser Leu Leu Asp Glu
                35                  40                  45

Gly Lys Gln Ser Leu Thr Lys Leu Ala Ala Ala Trp Gly Gly Ser Gly
    50                  55                  60

Ser Glu Ala Tyr Gln Gly Val Gln Gln Lys Trp Asp Ala Thr Ala Thr
65                  70                  75                  80

Glu Leu Asn Asn Ala Leu Gln Asn Leu Ala Arg Thr Ile Ser Glu Ala
                85                  90                  95

Gly Gln Ala Met Ala Ser Thr Glu Gly Asn Val Ala Gly Met Phe Ala
            100                 105                 110

Arg Gly Arg Lys Arg Arg Ser Thr Glu Gln Gln Trp Asn Phe Ala Gly
        115                 120                 125

Ile Glu Ala Ala Ala Ser Ala Ile Gln Gly Asn Val Ala Ser Ile His
    130                 135                 140

Ser Leu Leu Asp Glu Gly Lys Gln Ser Leu Thr Lys Leu Ala Ala Ala
145                 150                 155                 160

Trp Gly Gly Ser Gly Ser Glu Ala Tyr Gln Gly Val Gln Gln Lys Trp
                165                 170                 175

Asp Ala Thr Ala Thr Glu Leu Asn Asn Ala Leu Gln Asn Leu Ala Arg
            180                 185                 190

Thr Ile Ser Glu Ala Gly Gln Ala Met Ala Ser Thr Glu Gly Asn Val
        195                 200                 205

Ala Gly Met Phe Ala Arg Gly Arg Lys Arg Arg Ser Thr Glu Gln Gln
    210                 215                 220

Trp Asn Phe Ala Gly Ile Glu Ala Ala Ala Ser Ala Ile Gln Gly Asn
225                 230                 235                 240

Val Ala Ser Ile His Ser Leu Leu Asp Glu Gly Lys Gln Ser Leu Thr
                245                 250                 255

Lys Leu Ala Ala Ala Trp Gly Gly Ser Gly Ser Glu Ala Tyr Gln Gly
            260                 265                 270

Val Gln Gln Lys Trp Asp Ala Thr Ala Thr Glu Leu Asn Asn Ala Leu
        275                 280                 285

Gln Asn Leu Ala Arg Thr Ile Ser Glu Ala Gly Gln Ala Met Ala Ser
    290                 295                 300

Thr Glu Gly Asn Val Ala Gly Met Phe Ala
305                 310

<210> SEQ ID NO 17
<211> LENGTH: 2013
<212> TYPE: DNA
<213> ORGANISM: Artificial Sequence
<220> FEATURE:
<223> OTHER INFORMATION: pHDV nucleic acid sequence

<400> SEQUENCE: 17
atggactgga cctggattct cttcctggtg gccgccgcaa cacgggtgca ctcctcacag      60
attatgtaca actaccctgc tatgctggga cacgcaggag acatggcagg atacgctggt     120
accctgcagt ctctcggagc agagatcgca gtggaacagg ccgctctgca gagtgcctgg     180
cagggcgaca caggaattac ttaccaggct tggcaggcac agtggaatca ggccatggag     240
gatctggtcc gagcctatca cgctatgagc tccactcatg aggccaacac catggcaatg     300
atggcccggg ataccgctga agcagccaag tggggcggac gagtgaggag agccaaaagg     360
acagagcagc agtggaattt cgctggcatc gaagctgcag cctctgccat tcagggaaac     420
gtcgcttcca tccattctct gctcgacgaa ggcaagcaga gtctgactaa actcgctgca     480

```
gcatggggag gttcaggcag cgaggcatat cagggagtgc agcagaagtg ggatgcaacc    540
gccacagaac tgaacaatgc tctgcagaat ctcgcaagaa caatctccga ggccggacag    600
gctatggcat ctactgaagg gaacgtggct ggcatgttcg cacgggtgcg gcgagcaaaa    660
agggtcgagc caggaagaat tggcggaaac caggctcgcc tggctgcagt gctgctcgac    720
gtgagcaccc ccaacacact gaatgccgac tttgatctca tgcgctccgt ggccggaatt    780
acagatgctc ggaacgagga aatccgcgcc atgctgcagg ctttcattgg caggatgagc    840
ggagtgccac cttccgtctg gggaggtctg gcagctgcac gatttcagga cgtggtcgat    900
cgctggaatg ccgagagcac ccgactgtac acgtgctcc atgccatcgc tgacacaatt    960
aggcacaacg aggccgctct gagagaagca ggccagatcc acgccaggca tattgcagcc   1020
gctggcggag acctgagagt gcgaagggcc aagcggagcc tgctcgatgc tcacatcccc   1080
cagctgattg catcccatac tgccttcgca gccaaagccg gtctcatgag acataccatc   1140
ggacaggctg agcagcaggc aatgagtgca caggccttc accagggaga atcagctgca   1200
gccttccagg gggctcatgc acggtttgtg gctgcagccg ctaaggtcaa taccctgctc   1260
gacatcgcac aggctaacct gggagaggca gcaggtacat acgtggctgc agatgccgct   1320
gcagcctcta gttatactgg cttccgcgtg agacgggcta agcagcagca cacaatccag   1380
gtcactcctc agatgctgag aagcaccgct aatgatatcc aggcaaacat ggagcaggcc   1440
atgggcattg ctaaaggata tctggccaac caggaaaatg tgatgaaccc agctacctgg   1500
tcagggaccg gtgtggtcgc cagccacatg actgctaccg agatcacaaa tgaactgaac   1560
aaggtgctca ctggaggtac ccgactggca gagggactcg tccaggctgc agccctgatg   1620
gagggccacg aagccgactc ccagacagcc ttccaggctc tctttggggc cagtcatggt   1680
tcaagggtgc gccgagctaa agaactatc aactaccagt cggcgacgt ggatgcacac    1740 ggtgccatga ttcgagcaca ggcaggctcc ctggaggcag aacatcaggc catcatttct   1800
gacgtgctca ctgccagtga ttttggggga ggagctggct ctgctgcatg ccagggattc   1860
atcacccagc tggggaggaa ttttcaggtc atctacgagc aggctaacgc acacggacag   1920
aaggtccagg cagctggcaa caatatggcc cagaccgatt ccgccgtggg tagttcttgg   1980
gcttatccat acgacgtgcc tgattacgct tga    2013
```

<210> SEQ ID NO 18
<211> LENGTH: 670
<212> TYPE: PRT
<213> ORGANISM: Artificial Sequence
<220> FEATURE:
<223> OTHER INFORMATION: pHDV amino acid sequence

<400> SEQUENCE: 18

```
Met Asp Trp Thr Trp Ile Leu Phe Leu Val Ala Ala Thr Arg Val
1               5                   10                  15

His Ser Ser Gln Ile Met Tyr Asn Tyr Pro Ala Met Leu Gly His Ala
            20                  25                  30

Gly Asp Met Ala Gly Tyr Ala Gly Thr Leu Gln Ser Leu Gly Ala Glu
        35                  40                  45

Ile Ala Val Glu Gln Ala Ala Leu Gln Ser Ala Trp Gln Gly Asp Thr
    50                  55                  60

Gly Ile Thr Tyr Gln Ala Trp Gln Ala Gln Trp Asn Gln Ala Met Glu
65                  70                  75                  80

Asp Leu Val Arg Ala Tyr His Ala Met Ser Ser Thr His Glu Ala Asn
                85                  90                  95
```

```
Thr Met Ala Met Met Ala Arg Asp Thr Ala Glu Ala Ala Lys Trp Gly
            100                 105                 110

Gly Arg Val Arg Arg Ala Lys Arg Thr Glu Gln Gln Trp Asn Phe Ala
        115                 120                 125

Gly Ile Glu Ala Ala Ala Ser Ala Ile Gln Gly Asn Val Ala Ser Ile
    130                 135                 140

His Ser Leu Leu Asp Glu Gly Lys Gln Ser Leu Thr Lys Leu Ala Ala
145                 150                 155                 160

Ala Trp Gly Gly Ser Gly Ser Glu Ala Tyr Gln Gly Val Gln Gln Lys
                165                 170                 175

Trp Asp Ala Thr Ala Thr Glu Leu Asn Asn Ala Leu Gln Asn Leu Ala
            180                 185                 190

Arg Thr Ile Ser Glu Ala Gly Gln Ala Met Ala Ser Thr Glu Gly Asn
        195                 200                 205

Val Ala Gly Met Phe Ala Arg Val Arg Arg Ala Lys Arg Val Glu Pro
    210                 215                 220

Gly Arg Ile Gly Gly Asn Gln Ala Arg Leu Ala Ala Val Leu Leu Asp
225                 230                 235                 240

Val Ser Thr Pro Asn Thr Leu Asn Ala Asp Phe Asp Leu Met Arg Ser
                245                 250                 255

Val Ala Gly Ile Thr Asp Ala Arg Asn Glu Glu Ile Arg Ala Met Leu
            260                 265                 270

Gln Ala Phe Ile Gly Arg Met Ser Gly Val Pro Pro Ser Val Trp Gly
        275                 280                 285

Gly Leu Ala Ala Ala Arg Phe Gln Asp Val Val Asp Arg Trp Asn Ala
    290                 295                 300

Glu Ser Thr Arg Leu Tyr His Val Leu His Ala Ile Ala Asp Thr Ile
305                 310                 315                 320

Arg His Asn Glu Ala Ala Leu Arg Glu Ala Gly Gln Ile His Ala Arg
                325                 330                 335

His Ile Ala Ala Ala Gly Gly Asp Leu Arg Val Arg Arg Ala Lys Arg
            340                 345                 350

Ser Leu Leu Asp Ala His Ile Pro Gln Leu Ile Ala Ser His Thr Ala
        355                 360                 365

Phe Ala Ala Lys Ala Gly Leu Met Arg His Thr Ile Gly Gln Ala Glu
    370                 375                 380

Gln Gln Ala Met Ser Ala Gln Ala Phe His Gln Gly Glu Ser Ala Ala
385                 390                 395                 400

Ala Phe Gln Gly Ala His Ala Arg Phe Val Ala Ala Ala Lys Val
                405                 410                 415

Asn Thr Leu Leu Asp Ile Ala Gln Ala Asn Leu Gly Glu Ala Ala Gly
            420                 425                 430

Thr Tyr Val Ala Ala Asp Ala Ala Ala Ser Ser Tyr Thr Gly Phe
        435                 440                 445

Arg Val Arg Arg Ala Lys Arg Ala Asp Thr Ile Gln Val Thr Pro Gln
    450                 455                 460

Met Leu Arg Ser Thr Ala Asn Asp Ile Gln Ala Asn Met Glu Gln Ala
465                 470                 475                 480

Met Gly Ile Ala Lys Gly Tyr Leu Ala Asn Gln Glu Asn Val Met Asn
                485                 490                 495

Pro Ala Thr Trp Ser Gly Thr Gly Val Val Ala Ser His Met Thr Ala
            500                 505                 510
```

```
Thr Glu Ile Thr Asn Glu Leu Asn Lys Val Leu Thr Gly Gly Thr Arg
            515                 520                 525

Leu Ala Glu Gly Leu Val Gln Ala Ala Ala Leu Met Glu Gly His Glu
        530                 535                 540

Ala Asp Ser Gln Thr Ala Phe Gln Ala Leu Phe Gly Ala Ser His Gly
545                 550                 555                 560

Ser Arg Val Arg Arg Ala Lys Arg Thr Ile Asn Tyr Gln Phe Gly Asp
            565                 570                 575

Val Asp Ala His Gly Ala Met Ile Arg Ala Gln Ala Gly Ser Leu Glu
        580                 585                 590

Ala Glu His Gln Ala Ile Ile Ser Asp Val Leu Thr Ala Ser Asp Phe
    595                 600                 605

Trp Gly Gly Ala Gly Ser Ala Ala Cys Gln Gly Phe Ile Thr Gln Leu
        610                 615                 620

Gly Arg Asn Phe Gln Val Ile Tyr Glu Gln Ala Asn Ala His Gly Gln
625                 630                 635                 640

Lys Val Gln Ala Ala Gly Asn Asn Met Ala Gln Thr Asp Ser Ala Val
            645                 650                 655

Gly Ser Ser Trp Ala Tyr Pro Tyr Asp Val Pro Asp Tyr Ala
        660                 665                 670
```

<210> SEQ ID NO 19
<211> LENGTH: 987
<212> TYPE: DNA
<213> ORGANISM: Artificial Sequence
<220> FEATURE:
<223> OTHER INFORMATION: pVSW nucleic acid 2

<400> SEQUENCE: 19

```
atggactgga catgattctg tttctggtcg ccgctgctaa caagagtgca tagtacaatc    60
aattatcagt tcggggacgt ggacgctcac ggagcaatga tccgagcaca ggctggatca   120
ctggaggctg aacatcaggc aatcattagt gacgtgctga ctgcttcaga tttctggggc   180
ggggccggga gtgccgcttg ccagggattc atcacccagc tgggcagaaa ctttcaggtc   240
atctacgagc aggcaaatgc acacggacag aaggtccagg cagcaggaaa caatatggct   300
cagaccgact ccgcagtcgg gagctcctgg gccagaggaa ggaagcggag atctagtctg   360
ctggatgccc acatccccca gctgattgcc tctcatacag ctttcgctgc aaaagccgga   420
ctgatgcgac atactatcgg ccaggcagag cagcaggcca tgtctgctca ggcatttcac   480
cagggcgaaa gtgccgctgc attccaggga gcacatgctc gatttgtggc agctgcagcc   540
aaggtcaaca cactgctgga cattgcacag gccaatctgg agaggctgca ggaacctac   600
gtggcagctg atgcagccgc tgcatcaagc tatacagggt ccgcggacga aaaaggcgc   660
tccacttcta ggtttatgac cgaccctcac gctatgcggg atatggccgg cagattcgag   720
gtgcatgccc agacagtcga ggacgaagcc cgacggatgt gggctagcgc acagaacatc   780
gcaggagctg atggagcgg aatggcagaa gccacttccc tggataccat gacacagatg   840
aatcaggcct ttcgcaacat tgtgaatatg ctgcacggag tgagggacgg actggtccgc   900
gatgccaaca ttatgaaca gcaggaacag gcaagccagc agattctgag cagctaccca   960
tacgatgtcc ccgactacgc ataatga                                       987
```

<210> SEQ ID NO 20
<211> LENGTH: 327
<212> TYPE: PRT
<213> ORGANISM: Artificial Sequence
<220> FEATURE:
<223> OTHER INFORMATION: pVSW amino acid sequence 2

<400> SEQUENCE: 20

Met Asp Trp Thr Trp Ile Leu Phe Leu Val Ala Ala Thr Arg Val
1               5                   10                  15

His Ser Thr Ile Asn Tyr Gln Phe Gly Asp Val Asp Ala His Gly Ala
            20                  25                  30

Met Ile Arg Ala Gln Ala Gly Ser Leu Glu Ala Glu His Gln Ala Ile
        35                  40                  45

Ile Ser Asp Val Leu Thr Ala Ser Asp Phe Trp Gly Gly Ala Gly Ser
    50                  55                  60

Ala Ala Cys Gln Gly Phe Ile Thr Gln Leu Gly Arg Asn Phe Gln Val
65              70                  75                  80

Ile Tyr Glu Gln Ala Asn Ala His Gly Gln Lys Val Gln Ala Ala Gly
            85                  90                  95

Asn Asn Met Ala Gln Thr Asp Ser Ala Val Gly Ser Ser Trp Ala Arg
            100                 105                 110

Gly Arg Lys Arg Arg Ser Ser Leu Leu Asp Ala His Ile Pro Gln Leu
        115                 120                 125

Ile Ala Ser His Thr Ala Phe Ala Ala Lys Ala Gly Leu Met Arg His
    130                 135                 140

Thr Ile Gly Gln Ala Glu Gln Gln Ala Met Ser Ala Gln Ala Phe His
145                 150                 155                 160

Gln Gly Glu Ser Ala Ala Phe Gln Gly Ala His Ala Arg Phe Val
            165                 170                 175

Ala Ala Ala Ala Lys Val Asn Thr Leu Leu Asp Ile Ala Gln Ala Asn
            180                 185                 190

Leu Gly Glu Ala Ala Gly Thr Tyr Val Ala Ala Asp Ala Ala Ala
        195                 200                 205

Ser Ser Tyr Thr Gly Phe Arg Gly Arg Lys Arg Arg Ser Thr Ser Arg
    210                 215                 220

Phe Met Thr Asp Pro His Ala Met Arg Asp Met Ala Gly Arg Phe Glu
225                 230                 235                 240

Val His Ala Gln Thr Val Glu Asp Glu Ala Arg Arg Met Trp Ala Ser
            245                 250                 255

Ala Gln Asn Ile Ala Gly Ala Gly Trp Ser Gly Met Ala Glu Ala Thr
        260                 265                 270

Ser Leu Asp Thr Met Thr Gln Met Asn Gln Ala Phe Arg Asn Ile Val
    275                 280                 285

Asn Met Leu His Gly Val Arg Asp Gly Leu Val Arg Asp Ala Asn Asn
290                 295                 300

Tyr Glu Gln Gln Glu Gln Ala Ser Gln Gln Ile Leu Ser Ser Tyr Pro
305                 310                 315                 320

Tyr Asp Val Pro Asp Tyr Ala
            325

<210> SEQ ID NO 21
<211> LENGTH: 1071
<212> TYPE: DNA
<213> ORGANISM: Artificial Sequence
<220> FEATURE:
<223> OTHER INFORMATION: pDQE nucleic acid sequence

<400> SEQUENCE: 21

```
atggactgga cttggattct gttcctggtc gccgccgcaa ctcgcgtgca ctcagccgat    60
actattcagg tcactcctca gatgctgcgg tctaccgcca atgacatcca ggctaacatg   120
gagcaggcaa tgggaattgc caagggctac ctggccaacc aggaaaatgt gatgaacccc   180
gctacttgga gcggaaccgg cgtggtcgca tcccacatga ctgccaccga gatcactaat   240
gaactgaaca agtgctgac cggcgggaca agactggcag agggactggt ccaggcagct   300
gcactgatgg agggccacga agccgatagc cagaccgcct tccaggctct gtttggagca   360
tcacatggca gccgcgggcg aaagcggaga agctcccagt ccatgtactc ttatccagca   420
atgacagcca atgtggggga catggccgga tacactggcc ccacacagtc tctgggagct   480
gatattgcaa gtgagcgaac cgctccctca cgggcatgcc aggggacct gggaatgagt   540
caccaggatt ggcaggctca gtggaaccag gcaatggagg ccctggctag gcatatagg   600
cgctgccgac gggccctgcg acagatcggc gtgctggaac gacctgtcgg cgactctagt   660
gattgtggga caattagggt ggggtcattc cggggaagat ggctggaccc ccgacatgca   720
ggacctgcta ccgcagctga cgccggcgat agggggcgca aaagaaggag cgacccaaca   780
gtgctggccg atgctgtcgc aagaatggcc gagtttggca ggcacgtgga ggaactggtc   840
gctgagatcg aatccctggt gacacgcctg catgtcacat ggactggaga gggagcagca   900
gctcacgcag aagctcagcg acattgggca gcaggagaag caatgatgag acaggcactg   960
gcccagctga ctgctgcagg gcagagtgct catgcaaatt atgccggagc aatggctact  1020
aacctgggaa tgtggtccta cccttacgat gtgcctgact acgcataatg a           1071
```

<210> SEQ ID NO 22
<211> LENGTH: 355
<212> TYPE: PRT
<213> ORGANISM: Artificial Sequence
<220> FEATURE:
<223> OTHER INFORMATION: pDQE amino acid sequence 2

<400> SEQUENCE: 22

```
Met Asp Trp Thr Trp Ile Leu Phe Leu Val Ala Ala Thr Arg Val
1               5                   10                  15

His Ser Ala Asp Thr Ile Gln Val Thr Pro Gln Met Leu Arg Ser Thr
            20                  25                  30

Ala Asn Asp Ile Gln Ala Asn Met Glu Gln Ala Met Gly Ile Ala Lys
        35                  40                  45

Gly Tyr Leu Ala Asn Gln Glu Asn Val Met Asn Pro Ala Thr Trp Ser
    50                  55                  60

Gly Thr Gly Val Val Ala Ser His Met Thr Ala Thr Glu Ile Thr Asn
65                  70                  75                  80

Glu Leu Asn Lys Val Leu Thr Gly Gly Thr Arg Leu Ala Glu Gly Leu
                85                  90                  95

Val Gln Ala Ala Ala Leu Met Glu Gly His Glu Ala Asp Ser Gln Thr
            100                 105                 110

Ala Phe Gln Ala Leu Phe Gly Ala Ser His Gly Ser Arg Gly Arg Lys
        115                 120                 125

Arg Arg Ser Ser Gln Ser Met Tyr Ser Tyr Pro Ala Met Thr Ala Asn
    130                 135                 140

Val Gly Asp Met Ala Gly Tyr Thr Gly Thr Thr Gln Ser Leu Gly Ala
145                 150                 155                 160
```

-continued

```
Asp Ile Ala Ser Glu Arg Thr Ala Pro Ser Arg Ala Cys Gln Gly Asp
            165                 170                 175
Leu Gly Met Ser His Gln Asp Trp Gln Ala Gln Trp Asn Gln Ala Met
        180                 185                 190
Glu Ala Leu Ala Arg Ala Tyr Arg Arg Cys Arg Arg Ala Leu Arg Gln
    195                 200                 205
Ile Gly Val Leu Glu Arg Pro Val Gly Asp Ser Ser Asp Cys Gly Thr
210                 215                 220
Ile Arg Val Gly Ser Phe Arg Gly Arg Trp Leu Asp Pro Arg His Ala
225                 230                 235                 240
Gly Pro Ala Thr Ala Ala Asp Ala Gly Asp Arg Gly Arg Lys Arg Arg
                245                 250                 255
Ser Asp Pro Thr Val Leu Ala Asp Ala Val Ala Arg Met Ala Glu Phe
            260                 265                 270
Gly Arg His Val Glu Glu Leu Val Ala Glu Ile Glu Ser Leu Val Thr
        275                 280                 285
Arg Leu His Val Thr Trp Thr Gly Glu Gly Ala Ala His Ala Glu
    290                 295                 300
Ala Gln Arg His Trp Ala Ala Gly Glu Ala Met Met Arg Gln Ala Leu
305                 310                 315                 320
Ala Gln Leu Thr Ala Ala Gly Gln Ser Ala His Ala Asn Tyr Ala Gly
                325                 330                 335
Ala Met Ala Thr Asn Leu Gly Met Trp Ser Tyr Pro Tyr Asp Val Pro
            340                 345                 350
Asp Tyr Ala
        355

<210> SEQ ID NO 23
<211> LENGTH: 993
<212> TYPE: DNA
<213> ORGANISM: Artificial Sequence
<220> FEATURE:
<223> OTHER INFORMATION: pHAT nucleic acid sequence 2

<400> SEQUENCE: 23
atggactgga cttggattct gttcctggtc gctgccgcta ctagagtgca ttcatcacag    60
attatgtata actaccctgc tatgctggga cacgcaggag acatggcagg atacgctggg   120
accctgcaga gcctgggagc agagattgca gtggaacagg ccgctctgca gtccgcctgg   180
cagggagaca caggcatcac ttaccaggct tggcaggcac agtggaacca ggccatggag   240
gatctggtcc gcgcctatca cgctatgagc tccacccatg aggcaaatac aatggcaatg   300
atggcccggg atacagctga agcagcaaag tggggcgggc gaggacgaaa acggagatct   360
actgagcagc agtggaactt tgccgggatc gaagctgcag ccagtgctat tcagggaaat   420
gtggcatcaa tccacagcct gctggacgag ggcaagcagt ccctgaccaa actggctgca   480
gcatggggag gctctggcag tgaggcatac caggggtcc agcagaagtg ggatgcaact   540
gccaccgaac tgaacaatgc actgcagaac ctggcccgga ctattagtga ggccggccag   600
gctatggcat caaccgaagg gaatgtggct ggaatgttcg caagagggag gaaaaggcgc   660
tccaacgccg acccgtgct gtcttacaac ttcgatgcta tcgagtactc tgtccgccag   720
gaaatccata ccacagctgc acgattcaac gccgctctgc aggagctgag gagccagatc   780
gcccctctgc agcagctgtg gacaagagag gcagccgctg catatcacgc cgaacagctg   840
aagtggcatc aggccgctag cgccctgaac gaaatcctga ttgacctggg aaatgccgtg   900
```

```
aggcacggag cagacgatgt cgctcatgcc gaccgaagag cagcaggcgc ttgggccaga      960
tacccctacg atgtccccga ttacgcataa tga                                   993
```

<210> SEQ ID NO 24
<211> LENGTH: 329
<212> TYPE: PRT
<213> ORGANISM: Artificial Sequence
<220> FEATURE:
<223> OTHER INFORMATION: pHAT amino acid sequence 2

<400> SEQUENCE: 24

```
Met Asp Trp Thr Trp Ile Leu Phe Leu Val Ala Ala Thr Arg Val
1               5                   10                  15

His Ser Ser Gln Ile Met Tyr Asn Tyr Pro Ala Met Leu Gly His Ala
            20                  25                  30

Gly Asp Met Ala Gly Tyr Ala Gly Thr Leu Gln Ser Leu Gly Ala Glu
        35                  40                  45

Ile Ala Val Glu Gln Ala Ala Leu Gln Ser Ala Trp Gln Gly Asp Thr
    50                  55                  60

Gly Ile Thr Tyr Gln Ala Trp Gln Ala Gln Trp Asn Gln Ala Met Glu
65                  70                  75                  80

Asp Leu Val Arg Ala Tyr His Ala Met Ser Ser Thr His Glu Ala Asn
                85                  90                  95

Thr Met Ala Met Met Ala Arg Asp Thr Ala Glu Ala Ala Lys Trp Gly
            100                 105                 110

Gly Arg Gly Arg Lys Arg Arg Ser Thr Glu Gln Gln Trp Asn Phe Ala
        115                 120                 125

Gly Ile Glu Ala Ala Ala Ser Ala Ile Gln Gly Asn Val Ala Ser Ile
    130                 135                 140

His Ser Leu Leu Asp Glu Gly Lys Gln Ser Leu Thr Lys Leu Ala Ala
145                 150                 155                 160

Ala Trp Gly Gly Ser Gly Ser Glu Ala Tyr Gln Gly Val Gln Gln Lys
                165                 170                 175

Trp Asp Ala Thr Ala Thr Glu Leu Asn Asn Ala Leu Gln Asn Leu Ala
            180                 185                 190

Arg Thr Ile Ser Glu Ala Gly Gln Ala Met Ala Ser Thr Glu Gly Asn
        195                 200                 205

Val Ala Gly Met Phe Ala Arg Gly Arg Lys Arg Arg Ser Asn Ala Asp
    210                 215                 220

Pro Val Leu Ser Tyr Asn Phe Asp Ala Ile Glu Tyr Ser Val Arg Gln
225                 230                 235                 240

Glu Ile His Thr Thr Ala Ala Arg Phe Asn Ala Ala Leu Gln Glu Leu
                245                 250                 255

Arg Ser Gln Ile Ala Pro Leu Gln Gln Leu Trp Thr Arg Glu Ala Ala
            260                 265                 270

Ala Ala Tyr His Ala Glu Gln Leu Lys Trp His Gln Ala Ala Ser Ala
        275                 280                 285

Leu Asn Glu Ile Leu Ile Asp Leu Gly Asn Ala Val Arg His Gly Ala
    290                 295                 300

Asp Asp Val Ala His Ala Asp Arg Arg Ala Ala Gly Ala Trp Ala Arg
305                 310                 315                 320

Tyr Pro Tyr Asp Val Pro Asp Tyr Ala
                325
```

<210> SEQ ID NO 25
<211> LENGTH: 1074
<212> TYPE: DNA
<213> ORGANISM: Artificial Sequence
<220> FEATURE:
<223> OTHER INFORMATION: pBCU nucleic acid sequence 2

<400> SEQUENCE: 25

```
atggactgga catggattct gttcctggtc gcagccgcta caagagtgca ttccgccgag     60
atgaaaactg acgccgctac cctggcacag gaggccggga acttcgaacg catcagtgga    120
gacctgaaga cacagattga tcaggtggag tcaactgccg gaagcctgca gggacagtgg    180
cgaggcgccg ctggaacagc agcacaggct gcagtggtcc ggtttcagga agccgctaac    240
aagcagaaac aggagctgga cgaaatctcc actaatatta ggcaggctgg ggtgcagtac    300
tctcgcgcag atgaggaaca gcagcaggct ctgagctccc agatgggatt ccgaggccgg    360
aagcggagat ctagtgacca gattacatac aaccccggcg ccgtgagcga ctttgcatct    420
gatgtcggga gtcgggccgg acagctgcac atgatctatg aggacactgc cagcaaaacc    480
aatgctctgc aggaattctt tgccgggcat ggagctcagg gcttctttga tgcccaggct    540
cagatgctgt ccgggctgca gggactgatt gagactgtgg ccagcacgg gaccacaact     600
ggccatgtcc tggacaacgc catcgggacc gatcaggcaa ttgccggcct gttcagaggg    660
aggaaaaggc gctctgtgga accaggacgg atcggcggaa atcaggccag actggcagcc    720
gtgctgctgg acgtgagcac ccccaacaca ctgaatgctg actttgatct gatgagatca    780
gtggcaggca tcaccgatgc ccgcaatgag gaaattcgag caatgctgca ggccttcatc    840
ggaaggatgt caggagtgcc ccctagcgtc tggggaggcc tggctgcagc aaggtttcag    900
gacgtggtcg atcgctggaa cgccgagagc acccgactgt atcacgtgct gcatgctatc    960
gcagatacaa ttcggcacaa tgaggctgca ctgagagaag ccggcagat ccatgctaga    1020
catattgccg ctgctggagg cgacctgtac ccctacgacg tgcccgatta cgca         1074
```

<210> SEQ ID NO 26
<211> LENGTH: 358
<212> TYPE: PRT
<213> ORGANISM: Artificial Sequence
<220> FEATURE:
<223> OTHER INFORMATION: pBCU amino acid sequence 2

<400> SEQUENCE: 26

```
Met Asp Trp Thr Trp Ile Leu Phe Leu Val Ala Ala Thr Arg Val
1               5                   10                  15

His Ser Ala Glu Met Lys Thr Asp Ala Ala Thr Leu Ala Gln Glu Ala
            20                  25                  30

Gly Asn Phe Glu Arg Ile Ser Gly Asp Leu Lys Thr Gln Ile Asp Gln
        35                  40                  45

Val Glu Ser Thr Ala Gly Ser Leu Gln Gly Gln Trp Arg Gly Ala Ala
    50                  55                  60

Gly Thr Ala Ala Gln Ala Ala Val Val Arg Phe Gln Glu Ala Ala Asn
65                  70                  75                  80

Lys Gln Lys Gln Glu Leu Asp Glu Ile Ser Thr Asn Ile Arg Gln Ala
                85                  90                  95

Gly Val Gln Tyr Ser Arg Ala Asp Glu Glu Gln Gln Ala Leu Ser
            100                 105                 110

Ser Gln Met Gly Phe Arg Gly Arg Lys Arg Arg Ser Ser Asp Gln Ile
        115                 120                 125
```

Thr Tyr Asn Pro Gly Ala Val Ser Asp Phe Ala Ser Asp Val Gly Ser
130                 135                 140

Arg Ala Gly Gln Leu His Met Ile Tyr Glu Asp Thr Ala Ser Lys Thr
145                 150                 155                 160

Asn Ala Leu Gln Glu Phe Phe Ala Gly His Gly Ala Gln Gly Phe Phe
                165                 170                 175

Asp Ala Gln Ala Gln Met Leu Ser Gly Leu Gln Gly Leu Ile Glu Thr
                180                 185                 190

Val Gly Gln His Gly Thr Thr Thr Gly His Val Leu Asp Asn Ala Ile
                195                 200                 205

Gly Thr Asp Gln Ala Ile Ala Gly Leu Phe Arg Gly Arg Lys Arg Arg
210                 215                 220

Ser Val Glu Pro Gly Arg Ile Gly Gly Asn Gln Ala Arg Leu Ala Ala
225                 230                 235                 240

Val Leu Leu Asp Val Ser Thr Pro Asn Thr Leu Asn Ala Asp Phe Asp
                245                 250                 255

Leu Met Arg Ser Val Ala Gly Ile Thr Asp Ala Arg Asn Glu Glu Ile
                260                 265                 270

Arg Ala Met Leu Gln Ala Phe Ile Gly Arg Met Ser Gly Val Pro Pro
                275                 280                 285

Ser Val Trp Gly Gly Leu Ala Ala Ala Arg Phe Gln Asp Val Val Asp
                290                 295                 300

Arg Trp Asn Ala Glu Ser Thr Arg Leu Tyr His Val Leu His Ala Ile
305                 310                 315                 320

Ala Asp Thr Ile Arg His Asn Glu Ala Leu Arg Glu Ala Gly Gln
                325                 330                 335

Ile His Ala Arg His Ile Ala Ala Gly Gly Asp Leu Tyr Pro Tyr
                340                 345                 350

Asp Val Pro Asp Tyr Ala
                355

<210> SEQ ID NO 27
<211> LENGTH: 999
<212> TYPE: DNA
<213> ORGANISM: Artificial Sequence
<220> FEATURE:
<223> OTHER INFORMATION: pORF nucleic acid sequence 2

<400> SEQUENCE: 27
atggactgga catggattct gtttctggtc gctgccgcta caagagtgca ttcaactatc        60
aattatcagt tcggggacgt ggacgctcac ggagcaatga tccgagcaca ggctggactg       120
ctggaggcag aacatcaggc tattgtgcga gacgtgctgg cagctggaga tttctggggc       180
ggggcaggct ccgtggcatg ccaggagttc atcacacagc tgggcaggaa ctttcaggtc       240
atctacgaac aggcaaatgc acacggacag aaggtccagg cagcaggaaa caatatggcc       300
cagactgact ctgctgtggg gagctcctgg gcccgaggac gaaaacggag atctagtcag       360
atcatgtaca actatcccgc catgatggct catgcagggg acatggccgg gtatgctgga       420
accctgcaga gctgggagc agatatcgca tccgagcagg ccgtgctgag cagcgcctgg       480
cagggcgaca ccgggattac ataccagggc tggcagacac agtggaacca ggccctggaa       540
gatctggtcc gggcctatca gtccatgtct ggcactcacg agagcaatac catggctatg       600
ctggcaagag atgggccga agctgcaaag tggggaggca gaggcaggaa aaggcgctca       660
ggagcagacg ataccctgcg agtggagcct gccgtcatgc agggctttgc agctagtctg       720

```
gacggagcag cagagcacct ggctgtgcag ctggcagaac tggatgcaca ggtcggacag    780
atgctgggcg gctggagggg agctagtggc tcagcatacg gctctgcctg ggagctggct    840
catcgcggcg caggagaagt gcagctggga ctgagtatgc tggctgcagc cattgcccac    900
gctggagcag gctatcagca taatgaggct gcatctgccc aggtgctgag agaggtcggc    960
ggcggatacc cttacgatgt ccctgactat gcctaatga                           999
```

<210> SEQ ID NO 28
<211> LENGTH: 331
<212> TYPE: PRT
<213> ORGANISM: Artificial Sequence
<220> FEATURE:
<223> OTHER INFORMATION: pORF amino acid sequence 2

<400> SEQUENCE: 28

```
Met Asp Trp Thr Trp Ile Leu Phe Leu Val Ala Ala Thr Arg Val
1               5                   10                  15

His Ser Thr Ile Asn Tyr Gln Phe Gly Asp Val Asp Ala His Gly Ala
            20                  25                  30

Met Ile Arg Ala Gln Ala Gly Leu Leu Glu Ala Glu His Gln Ala Ile
        35                  40                  45

Val Arg Asp Val Leu Ala Gly Asp Phe Trp Gly Ala Gly Ser
    50                  55                  60

Val Ala Cys Gln Glu Phe Ile Thr Gln Leu Gly Arg Asn Phe Gln Val
65                  70                  75                  80

Ile Tyr Glu Gln Ala Asn Ala His Gly Gln Lys Val Gln Ala Ala Gly
                85                  90                  95

Asn Asn Met Ala Gln Thr Asp Ser Ala Val Gly Ser Ser Trp Ala Arg
            100                 105                 110

Gly Arg Lys Arg Arg Ser Ser Gln Ile Met Tyr Asn Tyr Pro Ala Met
        115                 120                 125

Met Ala His Ala Gly Asp Met Ala Gly Tyr Ala Gly Thr Leu Gln Ser
    130                 135                 140

Leu Gly Ala Asp Ile Ala Ser Glu Gln Ala Val Leu Ser Ser Ala Trp
145                 150                 155                 160

Gln Gly Asp Thr Gly Ile Thr Tyr Gln Gly Trp Gln Thr Gln Trp Asn
                165                 170                 175

Gln Ala Leu Glu Asp Leu Val Arg Ala Tyr Gln Ser Met Ser Gly Thr
            180                 185                 190

His Glu Ser Asn Thr Met Ala Met Leu Ala Arg Asp Gly Ala Glu Ala
        195                 200                 205

Ala Lys Trp Gly Gly Arg Gly Arg Lys Arg Arg Ser Gly Ala Asp Asp
    210                 215                 220

Thr Leu Arg Val Glu Pro Ala Val Met Gln Gly Phe Ala Ala Ser Leu
225                 230                 235                 240

Asp Gly Ala Ala Glu His Leu Ala Val Gln Leu Ala Glu Leu Asp Ala
                245                 250                 255

Gln Val Gly Gln Met Leu Gly Gly Trp Arg Gly Ala Ser Gly Ser Ala
            260                 265                 270

Tyr Gly Ser Ala Trp Glu Leu Ala His Arg Gly Ala Gly Glu Val Gln
        275                 280                 285

Leu Gly Leu Ser Met Leu Ala Ala Ile Ala His Ala Gly Ala Gly
    290                 295                 300
```

```
Tyr Gln His Asn Glu Ala Ala Ser Ala Gln Val Leu Arg Glu Val Gly
305                 310                 315                 320

Gly Gly Tyr Pro Tyr Asp Val Pro Asp Tyr Ala
                325                 330

<210> SEQ ID NO 29
<211> LENGTH: 4
<212> TYPE: PRT
<213> ORGANISM: Artificial Sequence
<220> FEATURE:
<223> OTHER INFORMATION: C-mannosylation site 1
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid

<400> SEQUENCE: 29

Trp Xaa Xaa Trp
1

<210> SEQ ID NO 30
<211> LENGTH: 4
<212> TYPE: PRT
<213> ORGANISM: Artificial Sequence
<220> FEATURE:
<223> OTHER INFORMATION: C-mannosylation site 2
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = any amino acid

<400> SEQUENCE: 30

Trp Xaa Xaa Ala
1

<210> SEQ ID NO 31
<211> LENGTH: 4
<212> TYPE: PRT
<213> ORGANISM: Artificial Sequence
<220> FEATURE:
<223> OTHER INFORMATION: C-mannosylation site 3
<220> FEATURE:
<221> NAME/KEY: MISC_FEATURE
<222> LOCATION: (2)..(2)
<223> OTHER INFORMATION: Xaa= any amino acid
<220> FEATURE:
<221> NAME/KEY: MISC_FEATURE
<222> LOCATION: (3)..(3)
<223> OTHER INFORMATION: Xaa= any amino acid

<400> SEQUENCE: 31

Ala Xaa Xaa Trp
1
```

SYNTHETIC IMMUNOGENS FOR PROPHYLAXIS OR TREATMENT OF TUBERCULOSIS

CROSS-REFERENCE TO RELATED APPLICATIONS

This application is a divisional of U.S. patent application Ser. No. 14/774,399, filed on Sep. 10, 2015, which is a U.S. national phase application filed under 35 U.S.C. § 371 claiming priority to International Patent Application No. PCT/US14/030776, filed Mar. 17, 2014, which is entitled to priority under 35 U.S.C. § 119(e) to U.S. Provisional Patent Application No. 61/800,375, filed Mar. 15, 2013, the contents of each of which are incorporated by reference herein in their entireties.

FIELD OF THE INVENTION

The present invention relates to multivalent constructs encoding tuberculosis (TB) immunogens encoding immunogenic TB antigens. Each construct encodes multiple immunogenic TB antigens and has coding sequences designed for high levels of expression. Prophylactic and therapeutic vaccines, and methods of making and using the same to induce immune responses, preventing TB infection and treat individuals infected with TB virus are provided.

BACKGROUND OF THE INVENTION

Tuberculosis (TB) is a major infectious disease with significant morbidity and mortality worldwide. The only currently licensed vaccine against TB is the *Bacillus* Calmette-Guerin (BCG) vaccine. Unfortunately, this vaccine confers poor protection against adult pulmonary TB and has been associated with adverse events. Therefore, the development of a novel, effective vaccine that induces long-term protection against TB is urgently needed. However, due to a variety of factors only a few antigens which have been determined to induce T cell immunity against TB have been studied so far. These include Ag85A, Ag85B, ESAT6, TB10.4, and Mtb39a. One issue is that there are many TB antigens from which to choose and current technologies for delivering TB antigens are limited and expensive.

There remains a need for economical and effective TB vaccines and methods that can induce immune responses against immunogenic TB antigens, protect against TB infection and provide effective treatment to individual who are infected with TB. There is also a need for a cost-effective delivery system to enable mass prophylactic vaccination against TB.

BRIEF DESCRIPTION OF THE DRAWINGS

FIG. 2A and FIG. 2B show the modified amino acid insert sequences for the multivalent TB vaccine constructs.

FIG. 6A described experimental design. FIG. 6B shows experimental results of immune responses against esxD, esxQ and esxE in mice vaccinated with the new version of plasmid pDQE. FIG. 6C shows experimental results of immune responses against esxV, esxS and esxW in mice vaccinated with the new version of plasmid pVSW. FIG. 6D shows experimental results of immune responses against esxB, esxC and esxU in mice vaccinated with the new version of plasmid pBCU. FIG. 6E shows experimental results of immune responses against esxO, esxR and esxF in mice vaccinated with the new version of plasmid pORF.

FIG. 7A shows the gating strategy used to analyze the frequency of CD4 and CD8 T cells positive for both IFN-□ and TNF-□ cytokines. FIG. 7B shows esx-specific CD4 T cells immune responses. FIG. 7C shows esx-specific CD4 T cells immune responses.

SUMMARY OF THE INVENTION

Figure 1A:
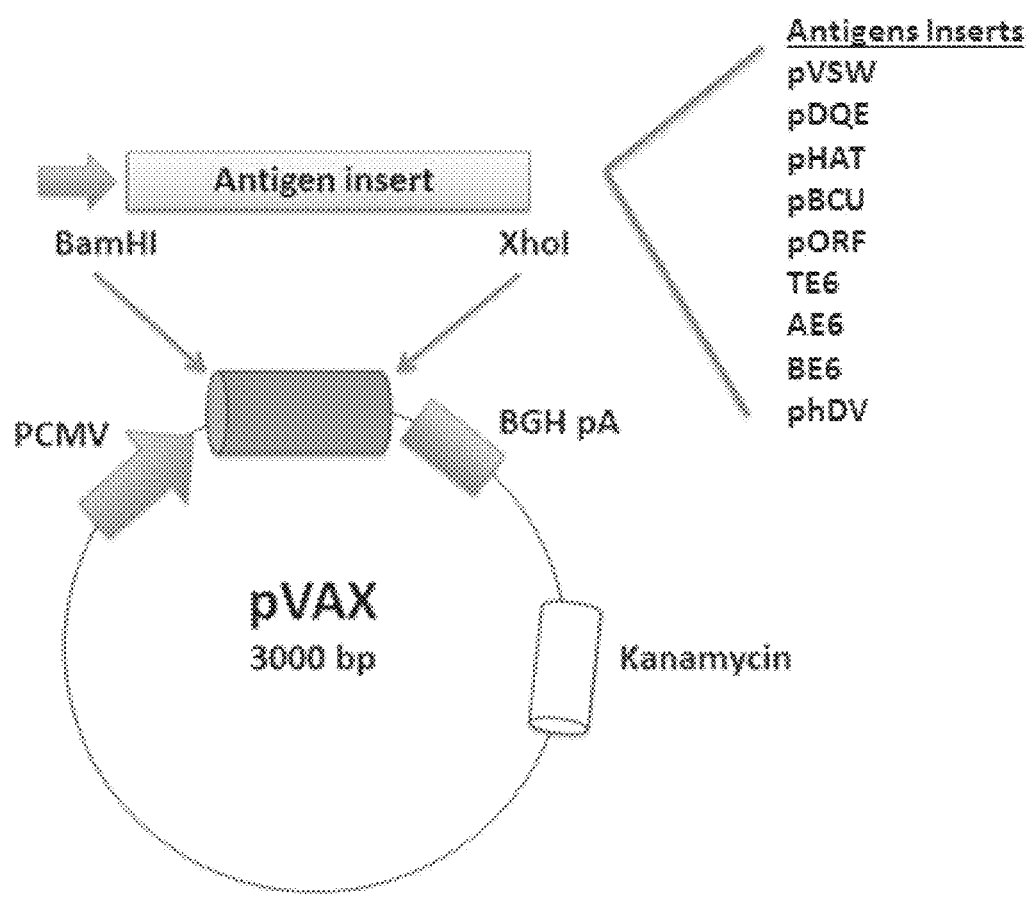
FIG. 1A depicts the construction of multivalent esx vaccine plasmids and in vitro expression of the trivalent expression vectors.

Composition comprising a nucleic acid molecule that encodes an amino acid sequences selected for the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, fragments thereof having at least 90% of full length, homologous sequences having at least 95% homology, and fragments of homologous sequences having at least 95% homology, said fragment of homologous sequences having at least 95% homology having at least 90% of full length are provided.

Composition comprising a nucleic acid molecule is selected for the group consisting of: SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, and SEQ ID NO:27 are provided.

SEQ ID NO:19, SEQ ID NO:21, SEQ ID NO:23, SEQ ID NO:25, and SEQ ID NO:27 SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, and SEQ ID NO:27 are provided.

Compositions comprising a plasmid that comprises SEQ ID NO:19, a plasmid that comprises SEQ ID NO:21, a plasmid that comprises SEQ ID NO:23, a plasmid that comprises SEQ ID NO:25, and a plasmid that comprises SEQ ID NO:27 are provided.

Compositions comprising a plasmid that comprises a V-S-W construct, a plasmid that comprises a D-Q-E construct, a plasmid that comprises an H-A-T construct, a plasmid that comprises a B-C-U construct, and a plasmid that comprises an O-R-F construct are provided.

Methods of inducing an immune response against TB in an individual are provided.

Methods of treating an individual who has been diagnosed with TB are provided.

Methods of preventing TB infection an individual are provided.

DETAILED DESCRIPTION

Safe, effective and economical TB vaccines are provided including embodiments employing DNA vaccine technology. The TB vaccines may be used in methods that can induce immune responses against immunogenic TB antigens, protect against TB infection and provide effective treatment to individual who are infected with TB. DNA vaccine technology can be used to provide cost-effective delivery of TB vaccine to large populations of individuals, enabling mass prophylactic vaccination against TB.

Inexpensive production, storage, transportation and administration of the vaccines make them ideal for use in vaccinated large populations in a cost-effective manner. Table 1 shows TB antigens currently being studied for use as vaccines.

TABLE 1

Current TB Vaccine Antigens in Clinical Trials

| Ag85A (Rv3804c) | Ag85B (Rv1886c) | ESAT6 (Rv3785) |
|---|---|---|
| TB10.4 (Rv0288) | Mtb39a (Rv1196) | Mtb32a (Rv0125) |
| Rv2660 | Rv1813c | Rv2608 |

A multivalent vaccine approach is attractive as broad immune responses could be generated by simultaneously targeting multiple antigens. It would be a distinct advantage to target entire families of genes at one time as this would limit the ability of the bacteria to escape host immunity. In this regard, the first multivalent expansive vaccine targeting an entire family of genes from TB is provided herein. The multivalent vaccine focuses on Early Secreted Antigenic Target 6-kDa (esat-6) protein family, which consist of 23 proteins. These proteins are attractive targets because they are important pathogenicity factors, potentially expressed under different physiological conditions; thus if all of these members could be targeted they would likely provide protection against multiple steps in the bacterial life cycle. In prior studies, there have only been limited analyses of just a few members of this family as vaccine immunogens. No current vaccine targets more than a few genes in this gene family. Here a novel approach has been developed using an optimized DNA vaccine candidate, delivered by intramuscular injection and in vivo electroporation, to increase the antigenic repertoire and produce broad immunity against TB. A synthetic TB DNA vaccine has been developed incorporating the totality of esx family genes that represent all of esx family members in a multivalent TB vaccine. Such a vaccine represents an exponential enhancement of immune targeting and breath for TB vaccine development. Multiple enhancements in plasmid technology contributed to this development and are outlined below.

The Early Secreted Antigenic Target 6-kDa (esat-6) protein family provide immunogenic targets for effective TB vaccines. Multivalent vaccines provide a broad range of targets. Of the 23 different esat-6 protein family members, some esat-6 proteins have sufficient homology that a single protein target can induce immune responses which recognize multiple TB esat-6 proteins. Using DNA vaccines, coding sequences for multiple immunogenic proteins can be included in a single, multivalent protein. Multiple different constructs can be used in combination to induce immune responses against members of the esat-6 family of proteins.

The esat-6 family consists of 23 low-mass proteins (esxA to esxW) and at least 10 can be divided further into subfamilies due to high sequence-related homology. One subfamily is the Mtb9.9 family, which consist of five open reading frames (ORF) with protein homology ranging from 92-98% (Table 2). The other subfamily is the QILSS subfamily, which consists of five neighboring ORFs that share individual identity on the protein level of over 98%.

In the vaccines disclosed herein, two antigens from the Mtb9.9 subfamily, esxO and esxV, were chosen as representative antigens useful to induce broad immune responses. TB antigens esxI, esxL and esxN are not used but their close structural relationship with esxO and esxV allow esxO and esxV to be a target for antigens of the MTb9.9 family.

Similarly, esxW was chosen from the QLISS subfamily to represent the subfamily which includes it five antigens, esxJ, esxK, esxM, esxP and esxW.

In addition, two other esat-6 proteins, esxS and esxG, share 96% homology; therefore, esxS will represent both antigens.

Choosing these antigens as representatives for other with which they have a high level of homology, should induce cross-reactive immune responses for all members that are relevant to control of TB. The remaining 11 esat-6 genes have little homology to each other and all have been incorporated as single antigen cassettes. Overall, a total of 15 esat-6 antigens are used and these 15 provide targets for all 23 members of the esat-6 family.

TABLE 2

Antigen Selection of Esx Members Based on Homology

| Subfamily | Antigens | Homology |
|---|---|---|
| MTb9.9 | esxI, esxL, esxN, esxO, esxV | 93-98% |
| QILSS | esxJ, esxK, esxM, esxP, esxW | >98% |
| N/A | esxS and esxG | ~96% |

Table 3 shows the 9 constructs that can be used in vaccines which can prevent TB infection and treat individuals infected with TB. As noted above esxO, esxV, esxW and esxS were chosen to represent themselves and closely related antigens in the presentation of antigens to induce a broad immune response.

TABLE 3

Vector Design of the 14 DNA TB Plasmids

| Vector | Design |
| --- | --- |
| pVSW | esxV-esxS-esxW |
| pDQE | esxD-esxQ-esxE |
| pHAT | esxH-esxA-esxT |
| pBCU | esxB-esxC-esxU |
| pORF | esxO-esxR-esxF |
| TE6 | esxA-esxA-esxA |
| AE6 | Ag85A-esxA |
| BE6 | Ag85B-esxA |
| phDV | esxH-esxA-esxU-esxS-esxD-esxV |
| new version of pVSW (pVSW.2) | esxV-esxS-esxW |
| new version of pDQE (pDOE.2) | esxD-esxQ-esxE |
| new version of pHAT (pHAT.2) | esxH-esxA-esxT |
| new version of pBCU (pBCU.2) | esxB-esxC-esxU |
| new version of pORF (pORF.2) | esxO-esxR-esxF |

The construct of each of these 14 vectors has an IgE signal peptide at the N terminus of each. The IgE signal peptide is optionally and it is intended that this disclosure be understood to be expressly disclosing sequences that include the IgE signal peptide at the N terminal and also expressing disclosing sequences excluding the IgE signal peptide with either no residue or a N terminal Methionine or a site for accepting addition of a signal peptides from another protein.

Similarly, the sequences comprise HA Tags at the C terminus of each. This structure is not required and in some embodiments, unwanted. It is intended that this disclosure be understood to be expressly disclosing sequences that include the HA Tag at the C terminal and also expressing disclosing sequences excluding the HA Tag.

The constructs provide for furin cleavage sites. Other protease cleavage sites which are processed by a protease commonly present in the cells of the vaccinated individual may be used in place of the furin sites.

As noted in the Example, the protein sequence has been modified to alter the pattern of their post translational addition of carbohydrates. Preservation of these modifications is highly desirable in some embodiments.

The constructs may be rearranged of otherwise changed whether by changing the order of antigen on a given plasmid or rearranging the groupings.

Vaccines are provided which comprise nucleic acid sequences on a plurality of plasmids encoding TB antigens, esxV, esxS, esxW, esxD, esxQ, esxE, esxH, esxA, esxT, esxB, esxC, esxU, esxO, esxR, esxF, wherein the protein sequences are modified with respect to C-manosylation mutation and N-linked glycosylation mutation. The antigens (esxA, esxE, esxF, esxU, esxW) have amino acids of N-linked glycosylation canonical sequence sites mutated (N-X-S/T to N-X-A). Amino acids with C-mannosylation canonical sequence sites also mutated (W-X-X-W (SEQ ID NO:29) to W-X-X-A (SEQ ID NO:30) or W-X-X-W (SEQ ID NO:29) to A-X-X-W (SEQ ID NO:31)).

In some embodiments, vaccines are provided that comprise 5 plasmids, each of which having coding sequences for the esx-antigens. In some embodiments, vaccines are compositions that comprise: a plasmid that comprises a V-S-W construct, a plasmid that comprises a D-Q-E construct, a plasmid that comprises an H-A-T construct, a plasmid that comprises a B-C-U construct, and a plasmid that comprises an O-R-F construct. In some such embodiments, the plasmid that comprises a V-S-W construct may comprise SEQ ID NO:19 or SEQ ID NO:1. In some such embodiments, the plasmid that comprises a D-Q-E construct may comprise SEQ ID NO:21 or SEQ ID NO:3. In some such embodiments, the plasmid that comprises an H-A-T construct may comprise SEQ ID NO:23 or SEQ ID NO:5. In some such embodiments, the plasmid that comprises a B-C-U construct may comprise SEQ ID NO:25 or SEQ ID NO:7. In some such embodiments, the plasmid that comprises an O-R-F construct may comprise SEQ ID NO:27 or SEQ ID NO:9. In some embodiments, vaccines are compositions comprising: a) a plasmid that comprises SEQ ID NO:19 or SEQ ID NO:1; b) a plasmid that comprises SEQ ID NO:21 or SEQ ID NO:3; c), a plasmid that comprises SEQ ID NO:23 or SEQ ID NO:5; d), a plasmid that comprises SEQ ID NO:25 or SEQ ID NO:7; and e) a plasmid that comprises SEQ ID NO:27 or SEQ ID NO:9. In some embodiments, vaccines are compositions comprising: a) a plasmid that comprises SEQ ID NO:19; b) a plasmid that comprises SEQ ID NO:21; c), a plasmid that comprises SEQ ID NO:23; d), a plasmid that comprises SEQ ID NO:25; and e) a plasmid that comprises SEQ ID NO:27.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein may mean any molecule added to the DNA plasmid vaccines described herein to enhance antigenicity of the one or more TB antigens encoded by the DNA plasmids and encoding nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered.

d. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein may mean a synthetic nucleic acid sequence, or corresponding polypeptide sequence, constructed based on analysis of an alignment of multiple subtypes of a particular TB antigen, that can be used to induce broad immunity against multiple subtypes or serotypes of a particular TB antigen. Consensus TB antigens may include consensus amino acid sequences of proteins of the esat-6 family as set forth herein. Nucleotide sequences that encode the consensus amino acid sequences are also provided. Also, synthetic antigens such as fusion proteins may be manipulated to include consensus sequences (or consensus antigens).

f. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

h. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

j. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

k. Fragment

"Fragment" may mean a polypeptide fragment of a TB antigen or polyprotein that is capable of eliciting an immune response in a mammal against TB by recognizing the particular TB antigen. A TB antigen may be one of the 23 members of the esat-6 protein family: esxA to esxW as well as TB antigens Ag85A and Ag85B, in each case with or without the IgE signal peptides, proteins 98% or more homologous to the consensus sequences set forth herein, proteins 99% or more homologous to the consensus sequences set forth herein, and proteins 100% identical to the consensus sequences set forth herein, in each case with or without signal peptides and/or a methionine at position 1. Fragments refer to less than full length of these proteins. A fragment may or may not for example comprise fragments of a TB Immunogen linked to a signal peptide such as an immunoglobulin signal peptide for example IgE signal peptide or IgG signal peptide.

"Fragment" may also mean a nucleic acid fragment of that encodes a TB antigen fragment set forth above l. Genetic Construct "Genetic construct" s used herein refers to the DNA or RNA molecules that comprise a nucleotide sequence which encodes a protein. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

m. Homology

"Homology," as used herein, refers to a degree of complementarity. There can be partial homology or complete homology (i.e., identity). A partially complementary sequence that at least partially inhibits a completely complementary sequence from hybridizing to a target nucleic acid is referred to using the functional term "substantially homologous." When used in reference to a double-stranded nucleic acid sequence such as a cDNA or genomic clone, the term "substantially homologous," as used herein, refers to a probe that can hybridize to a strand of the double-stranded nucleic acid sequence under conditions of low stringency. When used in reference to a single-stranded nucleic acid sequence, the term "substantially homologous," as used herein, refers to a probe that can hybridize to (i.e., is the complement of) the single-stranded nucleic acid template sequence under conditions of low stringency.

n. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

o. Impedance

"Impedance" as used herein may be used when discussing the feedback mechanism and can be converted to a current value according to Ohm's law, thus enabling comparisons with the preset current.

p. Immune Response

"Immune response" as used herein may mean the activation of a host's immune system, e.g., that of a mammal, in response to the introduction of one or more TB antigens via the provided DNA plasmid vaccines. The immune response can be in the form of a cellular or humoral response, or both.

q. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

r. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

s. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

t. Signal Peptide

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein preferably facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

u. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

v. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

w. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

x. Subtype

"Subtype" or "serotype": as used herein, interchangeably, and in reference to HBV, means genetic variants of an HBV such that one subtype is recognized by an immune system apart from a different subtype.

y. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

z. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. TB Antigens and Coding Sequences of TB Antigens

Fourteen multivalent constructs are provided, each encoding a fusion protein of two or more TB antigens. Coding sequences may encode TB antigens included in the amino acid sequences set out in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28.

SEQ ID NO:2 includes a single polyprotein having the amino acid sequences of three TB antigens: esxV, esxS and esxW. SEQ ID NO:2 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:1 provides a specific coding sequences encoding SEQ ID NO:2 designed for high expression levels. The construct may be referred to as pVSW. SEQ ID NO:1 is a V-S-W coding sequence.

SEQ ID NO:4 includes a single polyprotein having the amino acid sequences of three TB antigens: esxD, esxQ and esxE. SEQ ID NO:4 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:3 provides a specific coding sequences encoding SEQ ID NO:4 designed for high expression levels. The construct may be referred to as pDQE. SEQ ID NO:3 is a D-Q-E coding sequence.

SEQ ID NO:6 includes a single polyprotein having the amino acid sequences of three TB antigens: esxH, esxA and esxT. SEQ ID NO:6 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:5 provides a specific coding sequences encoding SEQ ID NO:6 designed for high expression levels. The construct may be referred to as pHAT. SEQ ID NO:5 is an H-A-T coding sequence.

SEQ ID NO:8 includes a single polyprotein having the amino acid sequences of three TB antigens: esxB, esxC and esxU. SEQ ID NO:8 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:7 provides a specific coding sequences encoding SEQ ID NO:8 designed for high expression levels. The construct may be referred to as pBCU. The construct may be referred to as pHAT. SEQ ID NO:7 is a B-C-U coding sequence.

SEQ ID NO:10 includes a single polyprotein having the amino acid sequences of three TB antigens: esxO, esxR and esxF. SEQ ID NO:10 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:9 provides a specific coding sequences encoding SEQ ID NO:10 designed for high expression levels. The construct may be referred to as pORF. SEQ ID NO:9 is an O-R-F coding sequence.

SEQ ID NO:12 includes a single polyprotein having three copies of TB antigen esx-A. SEQ ID NO:12 encoding: esxA, esxA and esxA and includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:12 provides a specific coding sequences encoding SEQ ID NO:11 designed for high expression levels. The construct may be referred to as TE6.

SEQ ID NO:14 includes a single polyprotein having the amino acid sequences of two TB antigens: Ag85A and esxA. SEQ ID NO:14 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:13 provides a specific coding sequences encoding SEQ ID NO:14 designed for high expression levels. The construct may be referred to as AE6.

SEQ ID NO:16 includes a single polyprotein having the amino acid sequences of two TB antigens: Ag85B and esxA. SEQ ID NO:16 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:15 provides a specific coding sequences encoding SEQ ID NO:16 designed for high expression levels. The construct may be referred to as BE6.

SEQ ID NO:18 includes a single polyprotein having the amino acid sequences of six TB antigens: esxH, esxA, esxU, esxS, esxD and esxV. SEQ ID NO:18 includes the optional IgE leader sequence at the N terminal. It is intended that this construct be considered as two alternatives: one as shown with the IgE leader and one without it. In the latter case, a start codon may be provided in place of the sequence encoding IgE leader. SEQ ID NO:17 provides a specific coding sequences encoding SEQ ID NO:18 designed for high expression levels. The construct may be referred to as phDV.

SEQ ID NO:20 includes a single polyprotein having the amino acid sequences of three TB antigens: esxV, esxS and esxW. SEQ ID NO:20 includes the optional IgE leader sequence at the N terminal. SEQ ID NO:20 also includes the optional HA-Tag sequence at the C terminal. It is intended that this construct be considered as alternatives: a construct may or may not have an IgE leader and independently a construct may or may not have an HA-Tag. In the case of those embodiments without the IgE leader, a start codon may be provided in place of the sequence encoding IgE leader. SEQ ID NO:19 provides a specific coding sequences encoding SEQ ID NO:20 designed for high expression levels. SEQ ID NO:19 is a nucleic acid sequence of the new version of pVSW (1005 bp) Optimized sequence that comprises coding sequences that encode the esx antigens esxV, esxS and esxW. The construct may be referred to as the new version of pORF (pORF.2). SEQ ID NO:19 is a V-S-W coding sequence.

SEQ ID NO:22 includes a single polyprotein having the amino acid sequences of three TB antigens: esxD, esxQ and esxE. SEQ ID NO:22 includes the optional IgE leader sequence at the N terminal. SEQ ID NO:22 also includes the optional HA-Tag sequence at the C terminal. It is intended that this construct be considered as alternatives: a construct may or may not have an Ige leader and independently a construct may or may not have an HA-Tag. In the case of those embodiments without the IgE leader, a start codon may be provided in place of the sequence encoding IgE leader. SEQ ID NO:21 provides a specific coding sequences encoding SEQ ID NO:22 designed for high expression levels. SEQ ID NO:21 is a nucleic acid sequence of the new version of pDQE (1089 bp) Optimized sequence that comprises coding sequences that encode the esx antigens esxD, esxQ and esxE. The construct may be referred to as the new version of pDQE (pDQE.2). SEQ ID NO:21 is a D-Q-E coding sequence.

SEQ ID NO:24 includes a single polyprotein having the amino acid sequences of three TB antigens: esxH, esxA and esxT. SEQ ID NO:24 includes the optional IgE leader sequence at the N terminal. SEQ ID NO:24 also includes the optional HA-Tag sequence at the C terminal. It is intended that this construct be considered as alternatives: a construct may or may not have an Ige leader and independently a construct may or may not have an HA-Tag. In the case of those embodiments without the IgE leader, a start codon may be provided in place of the sequence encoding IgE leader. SEQ ID NO:23 provides a specific coding sequences encoding SEQ ID NO:24 designed for high expression levels. SEQ ID NO:23 is a nucleic acid sequence of the new version of pHAT (1011 bp) Optimized sequence that comprises coding sequences that encode the esx antigens esxH, esxA and esxT. The construct may be referred to as the new version of pHAT (pHAT.2). SEQ ID NO:23 is an H-A-T coding sequence.

SEQ ID NO:26 includes a single polyprotein having the amino acid sequences of three TB antigens: esxB, esxC and esxU. SEQ ID NO:26 includes the optional IgE leader sequence at the N terminal. SEQ ID NO:26 also includes the optional HA-Tag sequence at the C terminal. It is intended that this construct be considered as alternatives: a construct may or may not have an Ige leader and independently a construct may or may not have an HA-Tag. In the case of those embodiments without the IgE leader, a start codon may be provided in place of the sequence encoding IgE leader. SEQ ID NO:25 provides a specific coding sequences encoding SEQ ID NO:26 designed for high expression levels. SEQ ID NO:25 is a nucleic acid sequence of the new version of pBCU (1098 bp) Optimized sequence that comprises coding sequences that encode the esx antigens esxB, esxC and esxU. The construct may be referred to as the new version of pBCU (pBCU.2). SEQ ID NO:25 is a B-C-U coding sequence.

SEQ ID NO:28 includes a single polyprotein having the amino acid sequences of three TB antigens: esxO, esxR and esxF. SEQ ID NO:28 includes the optional IgE leader sequence at the N terminal. SEQ ID NO:28 also includes the optional HA-Tag sequence at the C terminal. It is intended that this construct be considered as alternatives: a construct may or may not have an Ige leader and independently a construct may or may not have an HA-Tag. In the case of those embodiments without the IgE leader, a start codon may be provided in place of the sequence encoding IgE leader. SEQ ID NO:27 provides a specific coding sequences encoding SEQ ID NO:28 designed for high expression levels. SEQ ID NO:27 is a nucleic acid sequence of the new version of pORF (1017 bp) Optimized sequence that comprises coding sequences that encode the esx antigens esxO, esxR and esxF. The construct may be referred to as the new version of pORF (pORF.2). SEQ ID NO:27 is an O-R-F coding sequence.

A TB antigen may be one of the 23 members of the esat-6 protein family: esxA to esxW as well as TB antigens Ag85A and Ag85B, in each case with or without the IgE signal peptides, proteins 98% or more homologous to the consensus sequences set forth herein, proteins 99% or more homologous to the consensus sequences set forth herein, and proteins 100% identical to the consensus sequences set forth herein, in each case with or without signal peptides and/or a methionine at position 1. A fragment may or may not for example comprise a fragment of a TB Immunogen linked to a signal peptide such as an immunoglobulin signal peptide for example IgE signal peptide or IgG signal peptide.

A TB antigen may comprise SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 or SEQ ID NO:28, or any one of individual antigens esxV, esxS and esxW in SEQ ID NO:2, or any one of individual antigens esxD, esxQ and esxE in SEQ ID NO:4, or any one of individual antigens esxH, esxA and esxT in SEQ ID NO:6, or any one of individual antigens esxB, esxC and esxU in SEQ ID NO:8, or any one of individual antigens esxO, esxR and esxF in SEQ ID NO:10, or antigen esxA in SEQ ID NO:12, or any one of individual antigens Ag85A and esxA in SEQ ID NO:14, or any one of individual antigens Ag85B and esxA in SEQ ID NO:16, or any one of individual antigens esxH, esxA, esxU, esxS, esxD and esx-V in SEQ ID NO:18, or any one of individual antigens esxV, esxS and esxW in SEQ ID NO:20, or any one of individual antigens esxD, esxQ and esxE in SEQ ID NO:22, or any one of individual antigens esxH, esxA and esxT in SEQ ID NO:24, or any one of individual antigens esxB, esxC and esxU in SEQ ID NO:26, or any one of individual antigens esxO, esxR and esxF in SEQ ID NO:28, excluding in each case, any IgE signal peptide.

A homologous protein of a TB protein may be 95% or more, 96% or more, 97% or more, 98% or more of 99% or more homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 excluding the IgE signal peptide as well as to proteins 95% or more, 96% or more, 97% or more, 98% or more of 99% or more homologous to any one of individual antigens esxV, esxS and esxW in SEQ ID NO:2, to any one of individual antigens esxD, esxQ and esxE in SEQ ID NO:4, to any one of individual antigens esxH, esxA and esxT in SEQ ID NO:6, to any one of individual antigens esxB, esxC and esxU in SEQ ID NO:8, to any one of individual antigens esxO, esxR and esxF in SEQ ID NO:10, to antigen esxA in SEQ ID NO:12, to any one of individual antigens Ag85A and esxA in SEQ ID NO:14, to any one of individual antigens Ag85B and esxA in SEQ ID NO:16, to any one of individual antigens esxH, esxA, esxU, esxS, esxD and esx-V in SEQ ID NO:18, to any one of individual antigens esxV, esxS and esxW in SEQ ID NO:20, to any one of individual antigens esxD, esxQ and esxE in SEQ ID NO:22, to any one of individual antigens esxH, esxA and esxT in SEQ ID NO:24, to any one of individual antigens esxB, esxC and esxU in SEQ ID NO:26, to any one of individual antigens esxO, esxR and esxF in SEQ ID NO:28, excluding in each case, any IgE signal peptide.

A fragment of a TB protein may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 excluding the IgE signal peptide. A fragment may also comprised 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of any one of individual antigens esxV, esxS and esxW in SEQ ID NO:2, of any one of individual antigens esxD, esxQ and esxE in SEQ ID NO:4, of any one of individual antigens esxH, esxA and esxT in SEQ ID NO:6, of any one of individual antigens esxB, esxC and esxU in SEQ ID NO:8, of any one of individual antigens esxO, esxR and esxF in SEQ ID NO:10, to antigen esxA in SEQ ID NO:12, of any one of individual antigens Ag85A and esxA in SEQ ID NO:14, of any one of individual antigens Ag85B and esxA in SEQ ID NO:16, of any one of individual antigens esxH, esxA, esxU, esxS, esxD and esx-V in SEQ ID NO:18, of any one of individual antigens esxV, esxS and esxW in SEQ ID NO:20, of any one of individual antigens esxD, esxQ and esxE in SEQ ID NO:22, of any one of individual antigens esxH, esxA and esxT in SEQ ID NO:24, of any one of individual antigens esxB, esxC and esxU in SEQ ID NO:26, of any one of individual antigens esxO, esxR and esxF in SEQ ID NO:28, excluding in each case, any IgE signal peptide.

A fragment of a TB protein may be a fragment of a homologous protein. Such fragments comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of a protein that is 95% or more, 96% or more, 97% or more, 98% or more of 99% or more homologous to any one of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 excluding the IgE signal peptide. A fragment of a TB protein may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of a protein that is 95% or more, 96% or more, 97% or more, 98% or more of 99% or more homologous to any one of the individual antigens esxV, esxS and esxW in SEQ ID NO:2, to any one of individual antigens esxD, esxQ and esxE in SEQ ID NO:4, to any one of individual antigens esxH, esxA and esxT in SEQ ID NO:6, to any one of individual antigens esxB, esxC and esxU in SEQ ID NO:8, to any one of individual antigens esxO, esxR and esxF in SEQ ID NO:10, to antigen esxA in SEQ ID NO:12, to any one of individual antigens Ag85A and esxA in SEQ ID NO:14, to any one of individual antigens Ag85B and esxA in SEQ ID NO:16, to any one of individual antigens esxH, esxA, esxU, esxS, esxD and esx-V in SEQ ID NO:18, to any one of the individual antigens esxV, esxS and esxW in SEQ ID NO:20, to any one of individual antigens esxD, esxQ and esxE in SEQ ID NO:22, to any one of individual antigens esxH, esxA and esxT in SEQ ID NO:24, to any one of individual antigens esxB, esxC and esxU in SEQ ID NO:26, to any one of individual antigens esxO, esxR and esxF in SEQ ID NO:28, excluding in each case, any IgE signal peptide.

A TB antigen coding sequence may comprise SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25 or SEQ ID NO:27 excluding coding sequence of the IgE signal peptide. A TB antigen coding sequence may also comprise nucleic acid sequences that encode any one of individual antigens esxV, esxS and esxW in SEQ ID NO:2, to any one of individual antigens esxD, esxQ and esxE in SEQ ID NO:4, or any one of individual antigens esxH, esxA and esxT in SEQ ID NO:6, or any one of individual antigens esxB, esxC and esxU in SEQ ID NO:8, or any one of individual antigens esxO, esxR and esxF in SEQ ID NO:10, to antigen esxA in SEQ ID NO:12, or any one of individual antigens Ag85A and esxA in SEQ ID NO:14, or any one of individual antigens Ag85B and esxA in SEQ ID NO:16, or any one of individual antigens esxH, esxA, esxU, esxS, esxD and esx-V in SEQ ID NO:18, any one of individual antigens esxV, esxS and esxW in SEQ ID NO:20, to any one of individual antigens esxD, esxQ and esxE in SEQ ID NO:22, or any one of individual antigens esxH, esxA and esxT in SEQ ID NO:24, or any one of individual antigens esxB, esxC and esxU in SEQ ID NO:26, or any one of individual antigens esxO, esxR and esxF in SEQ ID NO:28 excluding in each case, any IgE signal peptide.

A coding sequence that is homologous to a coding sequence that encodes a TB antigen may be 95% or more, 96% or more, 97% or more, 98% or more of 99% or more homologous to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25 and SEQ ID NO:27 excluding coding sequence of the IgE signal peptide. Coding sequences that are homologous to a coding sequence that encodes a TB antigen may also be coding sequences that are 95% or more, 96% or more, 97% or more, 98% or more of 99% or more homologous to coding sequences of any one of individual antigens esxV, esxS and esxW in SEQ ID NO:1, to coding sequences of any one of individual antigens esxD, esxQ and esxE in SEQ ID NO:3, to coding sequences of any one of individual antigens esxH, esxA and esxT in SEQ ID NO:5, to coding sequences of any one of individual antigens esxB, esxC and esxU in SEQ ID NO:7, to coding sequences of any one of individual antigens esxO, esxR and esxF in SEQ ID NO:9, to antigen esx-A in SEQ ID NO:11, to coding sequences of any one of individual antigens Ag85A and esxA in SEQ ID NO:13, to coding sequences of any one of individual antigens Ag85B and esxA in SEQ ID NO:15, to coding sequences of any one of individual antigens esxH, esxA, esxU, esxS, esxD and esx-V in SEQ ID NO:17, to coding sequences of any one of individual antigens esxV, esxS and esxW in SEQ ID NO:19, to coding sequences of any one of individual antigens esxD, esxQ and esxE in SEQ ID NO:21, to coding sequences of any one of individual antigens esxH, esxA and esxT in SEQ ID NO:23, to coding sequences of any one of individual antigens esxB, esxC and esxU in SEQ ID NO:25, and to coding sequences of any one of individual antigens esxO, esxR and esxF in SEQ ID NO:27, excluding in each case, coding sequences encoding any IgE signal peptide A fragment of a TB antigen coding sequence may comprise a fragment of the full length coding sequence which is 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of coding sequence of the particular full length TB antigen coding sequence. A fragment of a TB antigen coding sequence may comprise nucleic acid sequences that encode is 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of any one of individual antigens esxV, esxS and esxW in SEQ ID NO:2, of any one of individual antigens esxD, esxQ and esxE in SEQ ID NO:4, of any one of individual antigens esxH, esxA and esxT in SEQ ID NO:6, of any one of individual antigens esxB, esxC and esxU in SEQ ID NO:8, of any one of individual antigens esxO, esxR and esxF in SEQ ID NO:10, of antigen esxA in SEQ ID NO:12, of any one of individual antigens Ag85A and esxA in SEQ ID NO:14, to any one of individual antigens Ag85B and esxA in SEQ ID NO:16, of any one of individual antigens esxH, esxA, esxU, esxS, esxD and esx-V in SEQ ID NO:18, of any one of individual antigens esxV, esxS and esxW in SEQ ID NO:20, of any one of individual antigens esxD, esxQ and esxE in SEQ ID NO:22, of any one of individual antigens esxH, esxA and esxT in SEQ ID NO:24, of any one of individual antigens esxB, esxC and esxU in SEQ ID NO:26, of any one of individual antigens esxO, esxR and esxF in SEQ ID NO:28, excluding in each case, any IgE signal peptide.

A fragment of a coding sequence that is homologous to a TB antigen coding sequence may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of coding sequence that may be 95% or more, 96% or more, 97% or more, 98% or more of 99% or more homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 excluding the IgE signal peptide.

A fragment of a coding sequence that is homologous to a TB antigen coding sequence may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence that may be 95% or more, 96% or more, 97% or more, 98% or more of 99% or more homologous to any one of the individual antigens esxV, esxS and esxW in SEQ ID NO:2, to any one of individual antigens esxD, esxQ and esxE in SEQ ID NO:4, to any one of individual antigens esxH, esxA and esxT in SEQ ID NO:6, to any one of individual antigens esxB, esxC and esxU in SEQ ID NO:8, to any one of individual antigens esxO, esxR and esxF in SEQ ID NO:10, to antigen esxA in SEQ ID NO:12, to any one of individual antigens Ag85A and esxA in SEQ ID NO:14, to any one of individual antigens Ag85B and esxA in SEQ ID NO:16, to any one of individual antigens esxH, esxA, esxU, esxS, esxD and esx-V in SEQ ID NO:18, to any one of the individual antigens esxV, esxS and esxW in SEQ ID NO:20, to any one of individual antigens esxD, esxQ and esxE in SEQ ID NO:22, to any one of individual antigens esxH, esxA and esxT in SEQ ID NO:24, to any one of individual antigens esxB, esxC and esxU in SEQ ID NO:26, to any one of individual antigens esxO, esxR and esxF in SEQ ID NO:28, excluding in each case, any IgE signal peptide.

The genetic constructs can comprise regulatory elements for gene expression of the coding sequences of the nucleic acid. The regulatory elements can be a promoter, an enhancer an initiation codon, a stop codon, or a polyadenylation signal.

The nucleic acid sequences can make up a genetic construct that can be a vector. The vector can be capable of expressing an antigen in the cell of a mammal in a quantity effective to elicit an immune response in the mammal. The vector can be recombinant. The vector can comprise heterologous nucleic acid encoding the antigen. The vector can be a plasmid. The vector can be useful for transfecting cells with nucleic acid encoding an antigen, which the transformed host cell is cultured and maintained under conditions wherein expression of the antigen takes place.

Coding sequences can be optimized for stability and high levels of expression. In some instances, codons are selected to reduce secondary structure formation of the RNA such as that formed due to intermolecular bonding.

3. Plasmid

Provided herein is a vector that is capable of expressing multivalent TB constructs in the cell of a mammal in a quantity effective to elicit an immune response in the mammal. The vector may comprise heterologous nucleic acid encoding the one or more TB antigens. The vector may be a plasmid. The plasmid may be useful for transfecting cells with nucleic acid encoding a TB antigen, which the transformed host cell is cultured and maintained under conditions wherein expression of the TB antigen takes place.

Plasmids may comprising coding sequences encoding SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 with or without the IgE leader. Plasmids may comprising coding sequences encoding any one of individual antigens esxV, esxS and esxW in SEQ ID NO:2, or any one of individual antigens esxD, esxQ and esxE in SEQ ID NO:4, or any one of individual antigens esxH, esxA and esxT in SEQ ID NO:6, or any one of individual antigens esxB, esxC and esxU in SEQ ID NO:8, to any one of individual antigens esxO, esxR and esxF in SEQ ID NO:10, to antigen esxA in SEQ ID NO:12, or any one of individual antigens Ag85A and esxA in SEQ ID NO:14, or any one of individual antigens Ag85B and esxA in SEQ ID NO:16, or any one of individual antigens esxH, esxA, esxU, esxS, esxD and esx-V in SEQ ID NO:18, or any one of individual antigens esxV, esxS and esxW in SEQ ID NO:20, or any one of individual antigens esxD, esxQ and esxE in SEQ ID NO:22, or any one of individual antigens esxH, esxA and esxT in SEQ ID NO:24, or any one of individual antigens esxB, esxC and esxU in SEQ ID NO:26, to any one of individual antigens esxO, esxR and esxF in SEQ ID NO:28, excluding in each case, any IgE signal peptide.

Plasmids may comprising coding sequences encoding proteins that may be 95% or more, 96% or more, 97% or more, 98% or more of 99% or more homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 with or without the IgE leader. Plasmids may comprising coding sequences encoding proteins that may be 95% or more, 96% or more, 97% or more, 98% or more of 99% or more homologous to any one of individual antigens esxV, esxS and esxW in SEQ ID NO:2, to any one of individual antigens esxD, esxQ and esxE in SEQ ID NO:4, to any one of individual antigens esxH, esxA and esxT in SEQ ID NO:6, to any one of individual antigens esxB, esxC and esxU in SEQ ID NO:8, to any one of individual antigens esxO, esxR and esxF in SEQ ID NO:10, to antigen esxA in SEQ ID NO:12, to any one of individual antigens Ag85A and esxA in SEQ ID NO:14, to any one of individual antigens Ag85B and esxA in SEQ ID NO:16, to any one of individual antigens esxH, esxA, esxU, esxS, esxD and esx-V in SEQ ID NO:18, homologous to any one of individual antigens esxV, esxS and esxW in SEQ ID NO:20, to any one of individual antigens esxD, esxQ and esxE in SEQ ID NO:22, to any one of individual antigens esxH, esxA and esxT in SEQ ID NO:24, to any one of individual antigens esxB, esxC and esxU in SEQ ID NO:26, to any one of individual antigens esxO, esxR and esxF in SEQ ID NO:28, excluding in each case, any IgE signal peptide.

Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 with or without the IgE leader. Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence encoding any one of individual antigens esxV, esxS and esxW in SEQ ID NO:2, or any one of individual antigens esxD, esxQ and esxE in SEQ ID NO:4, or any one of individual antigens esxH, esxA and esxT in SEQ ID NO:6, or any one of individual antigens esxB, esxC and esxU in SEQ ID NO:8, or any one of individual antigens esxO, esxR and esxF in SEQ ID NO:10, or antigen esxA in SEQ ID NO:12, or any one of individual antigens Ag85A and esxA in SEQ ID NO:14, or any one of individual antigens Ag85B and esxA in SEQ ID NO:16, or any one of individual antigens esxH, esxA, esxU, esxS, esxD and esx-V in SEQ ID NO:18, any one of individual antigens esxV, esxS and esxW in SEQ ID NO:20, or any one of individual antigens esxD, esxQ and esxE in SEQ ID NO:22, or any one of individual antigens esxH, esxA and esxT in SEQ ID NO:24, or any one of individual antigens esxB, esxC and esxU in SEQ ID NO:26, or any one of individual antigens esxO, esxR and esxF in SEQ ID NO:28 excluding in each case, any IgE signal peptide.

Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence that may be 95% or more, 96% or more, 97% or more, 98% or more of 99% or more homologous to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26 and SEQ ID NO:28 with or without the IgE leader. Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence encoding a protein that may be may be 95% or more, 96% or more, 97% or more, 98% or more of 99% or more homologous to any one of individual antigens esxV, esxS and esxW in SEQ ID NO:2, to any one of individual antigens esxD, esxQ and esxE in SEQ ID NO:4, to any one of individual antigens esxH, esxA and esxT in SEQ ID NO:6, to any one of individual antigens esxB, esxC and esxU in SEQ ID NO:8, to any one of individual antigens esxO, esxR and esxF in SEQ ID NO:10, to antigen esxA in SEQ ID NO:12, to any one of individual antigens Ag85A and esxA in SEQ ID NO:14, to any one of individual antigens Ag85B and esxA in SEQ ID NO:16, to any one of individual antigens esxH, esxA, esxU, esxS, esxD and esx-V in SEQ ID NO:18, to any one of individual antigens esxV, esxS and esxW in SEQ ID NO:20, to any one of individual antigens esxD, esxQ and esxE in SEQ ID NO:22, to any one of individual antigens esxH, esxA and esxT in SEQ ID NO:24, to any one of individual antigens esxB, esxC and esxU in SEQ ID NO:26, to any one of individual antigens esxO, esxR and esxF in SEQ ID NO:28 excluding in each case, any IgE signal peptide.

Plasmids may comprise SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25 or SEQ ID NO:27 with or without the IgE leader. Plasmids may comprising coding sequences encoding any one of individual antigens esxV, esxS and esxW in SEQ ID NO:1, or any one of individual antigens esxD, esxQ and esxE in SEQ ID NO:3, or any one of individual antigens esxH, esxA and esxT in SEQ ID NO:5, or any one of individual antigens esxB, esxC and esxU in SEQ ID NO:7, or any one of individual antigens esxO, esxR and esxF in SEQ ID NO:9, or antigen esxA in SEQ ID NO:11, or any one of individual antigens Ag85A and esxA in SEQ ID NO:13, or any one of individual antigens Ag85B and esxA in SEQ ID NO:15, or any one of individual antigens esxH, esxA, esxU, esxS, esxD and esx-V in SEQ ID NO:17, or any one of individual antigens esxV, esxS and esxW in SEQ ID NO:19, or any one of individual antigens esxD, esxQ and esxE in SEQ ID NO:21, or any one of individual antigens esxH, esxA and esxT in SEQ ID NO:23, or any one of individual antigens esxB, esxC and esxU in SEQ ID NO:25, or any one of individual antigens esxO, esxR and esxF in SEQ ID NO:25, excluding in each case, any IgE signal peptide.

Plasmids may comprising coding sequences encoding proteins that may be 95% or more, 96% or more, 97% or more, 98% or more of 99% or more homologous to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25 and SEQ ID NO:27 with or without the IgE leader. Plasmids may comprising coding sequences encoding proteins that may be 95% or more, 96% or more, 97% or more, 98% or more of 99% or more homologous to any one of individual antigens esxV, esxS and esxW in SEQ ID NO:1, to any one of individual antigens esxD, esxQ and esxE in SEQ ID NO:3, to any one of individual antigens esxH, esxA and esxT in SEQ ID NO:5, to any one of individual antigens esxB, esxC and esxU in SEQ ID NO:7, to any one of individual antigens esxO, esxR and esxF in SEQ ID NO:9, to antigen esxA in SEQ ID NO:11, to any one of individual antigens Ag85A and esxA in SEQ ID NO:13, to any one of individual antigens Ag85B and esxA in SEQ ID NO:15 and to any one of individual antigens esxH, esxA, esxU, esxS, esxD and esx-V in SEQ ID NO:17, excluding in each case, any IgE signal peptide.

Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25 and SEQ ID NO:27 with or without the IgE leader. Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence encoding any one of individual antigens esxV, esxS and esxW in SEQ ID NO:1, or any one of individual antigens esxD, esxQ and esxE in SEQ ID NO:3, of any one of individual antigens esxH, esxA and esxT in SEQ ID NO:5, or any one of individual antigens esxB, esxC and esxU in SEQ ID NO:7, or any one of individual antigens esxO, esxR and esxF in SEQ ID NO:9, to antigen esxA in SEQ ID NO:11, or any one of individual antigens Ag85A and esxA in SEQ ID NO:13, or any one of individual antigens Ag85B and esxA in SEQ ID NO:15, or any one of individual antigens esxH, esxA, esxU, esxS, esxD and esx-V in SEQ ID NO:17, or any one of individual antigens esxV, esxS and esxW in SEQ ID NO:19, or any one of individual antigens esxD, esxQ and esxE in SEQ ID NO:21, of any one of individual antigens esxH, esxA and esxT in SEQ ID NO:23, or any one of individual antigens esxB, esxC and esxU in SEQ ID NO:25, or any one of individual antigens esxO, esxR and esxF in SEQ ID NO:27, excluding in each case, any IgE signal peptide.

Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence that may be 95% or more, 96% or more, 97% or more, 98% or more of 99% or more homologous to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25 and SEQ ID NO:27 with or without the IgE leader. Plasmids may comprising coding sequences encoding 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more of a coding sequence encoding a protein that may be may be 95% or more, 96% or more, 97% or more, 98% or more of 99% or more homologous to any one of individual antigens esxV, esxS and esxW in SEQ ID NO:1, to any one of individual antigens esxD, esxQ and esxE in SEQ ID NO:3, to any one of individual antigens esxH, esxA and esxT in SEQ ID NO:5, to any one of individual antigens esxB, esxC and esxU in SEQ ID NO:7, to any one of individual antigens esxO, esxR and esxF in SEQ ID NO:9, to antigen esxA in SEQ ID NO:11, to any one of individual antigens Ag85A and esxA in SEQ ID NO:13, to any one of individual antigens Ag85B and esxA in SEQ ID NO:15, to any one of individual antigens esxH, esxA, esxU, esxS, esxD and esx-V in SEQ ID NO:17, to any one of individual antigens esxV, esxS and esxW in SEQ ID NO:19, to any one of individual antigens esxD, esxQ and esxE in SEQ ID NO:21, to any one of individual antigens esxH, esxA and esxT in SEQ ID NO:23, to any one of individual antigens esxB, esxC and esxU in SEQ ID NO:25, to any one of individual antigens esxO, esxR and esxF in SEQ ID NO:27, excluding in each case, any IgE signal peptide.

An embodiments disclosed herein is made up of 9 plasmid comprising coding sequence for thirty proteins. There is some duplication but there are still thirty proteins encoded by the 9 plasmids. In some embodiments there are 6, 7, 8, 9 10, 11, 12, 13, 14, 15, 16, 17, 18 plasmids. The coding sequences may in different orders. The coding sequences may be on different plasmids included on plasmids with coding sequences indicated to be on other plasmids in the embodiment disclosed herein.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration.

The vector can be pVAX1 or a pVax1 variant with changes such as the variant plasmid described herein. The variant pVax1 plasmid is a 2998 basepair variant of the backbone vector plasmid pVAX1 (Invitrogen, Carlsbad Calif.). The CMV promoter is located at bases 137-724. The T7 promoter/priming site is at bases 664-683. Multiple cloning sites are at bases 696-811. Bovine GH polyadenylation signal is at bases 829-1053. The Kanamycin resistance gene is at bases 1226-2020. The pUC origin is at bases 2320-2993.

Based upon the sequence of pVAX1 available from Invitrogen, the following mutations were found in the sequence of pVAX1 that was used as the backbone for plasmids 1-6 set forth herein:

C>G241 in CMV promoter

C>T 1942 backbone, downstream of the bovine growth hormone polyadenylation signal (bGHpolyA)

A>—2876 backbone, downstream of the Kanamycin gene

C>T 3277 in pUC origin of replication (Ori) high copy number mutation (see Nucleic Acid Research 1985)

G>C 3753 in very end of pUC Ori upstream of RNASeH site

Base pairs 2, 3 and 4 are changed from ACT to CTG in backbone, upstream of CMV promoter.

The backbone of the vector can be pAV0242. The vector can be a replication defective adenovirus type 5 (Ad5) vector.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA I or pcDNA3

(Invitrogen, San Diego, Calif.), which may be used for protein production in mammalian cells such as Chinese hamster ovary (CHO) cells.

4. Pharmaceutical Compositions and Vaccines

Compositions are provided which comprise nucleic acid molecules. For example, compositions may comprise plurality of six, seven, eight, nine, ten or more different plasmids.

Compositions may comprise vectors pVSW, pDQE, pHAT, pBCU, pORF, TE6. AE6, BE6, phDV, pVSW.2, pDQE.2, pHAT.2, pBCU.2, pORF.2. Other combinations with various numbers of plasmids may be used.

In some embodiments, vaccines are provided that comprise 5 plasmids, each of which having coding sequences for the esx-antigens. In some embodiments, vaccines are compositions that comprise: a plasmid that comprises a V-S-W construct, a plasmid that comprises a D-Q-E construct, a plasmid that comprises an H-A-T construct, a plasmid that comprises a B-C-U construct, and a plasmid that comprises an O-R-F construct. In some such embodiments, the plasmid that comprises a V-S-W construct may comprise SEQ ID NO:19 or SEQ ID NO:1. In some such embodiments, the plasmid that comprises a D-Q-E construct may comprise SEQ ID NO:21 or SEQ ID NO:3. In some such embodiments, the plasmid that comprises an H-A-T construct may comprise SEQ ID NO:23 or SEQ ID NO:5. In some such embodiments, the plasmid that comprises a B-C-U construct may comprise SEQ ID NO:25 or SEQ ID NO:7. In some such embodiments, the plasmid that comprises an O-R-F construct may comprise SEQ ID NO:27 or SEQ ID NO:9. In some embodiments, vaccines are compositions comprising: a) a plasmid that comprises SEQ ID NO:19 or SEQ ID NO:1; b) a plasmid that comprises SEQ ID NO:21 or SEQ ID NO:3; c), a plasmid that comprises SEQ ID NO:23 or SEQ ID NO:5; d), a plasmid that comprises SEQ ID NO:25 or SEQ ID NO:7; and e) a plasmid that comprises SEQ ID NO:27 or SEQ ID NO:9. In some embodiments, vaccines are compositions comprising: a) a plasmid that comprises SEQ ID NO:19; b) a plasmid that comprises SEQ ID NO:21; c), a plasmid that comprises SEQ ID NO:23; d), a plasmid that comprises SEQ ID NO:25; and e) a plasmid that comprises SEQ ID NO:27.

In some embodiments, a composition further comprises coding sequence for chemokine CCL20, IL-12, IL-15 and/or IL-28. Coding sequence for chemokine CCL20, IL-12, IL-15 and/or IL-28 may be included on one or more nucleic acid molecules that comprise coding sequence for one or more TB antigens. Coding sequence for chemokine CCL20, IL-12, IL-15 and/or IL-28 may be included on a separate nucleic acid molecules such as a separate plasmid.

Provided herein is a vaccine capable of generating in a mammal an immune response against TB. The vaccine may comprise each plasmid as discussed above. The vaccine may comprise a plurality of the plasmids, or combinations thereof. The vaccine may be provided to induce a therapeutic or prophylactic immune response.

The vaccine can be in the form of a pharmaceutical composition. The pharmaceutical composition can comprise the vaccine.

The vaccine may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof. The pharmaceutical compositions can comprise about 5 nanograms to about 10 mg of the vaccine DNA. In some embodiments, pharmaceutical compositions according to the present invention comprise about 25 nanogram to about 5 mg of vaccine DNA. In some embodiments, the pharmaceutical compositions contain about 50 nanograms to about 1 mg of DNA. In some embodiments, the pharmaceutical compositions contain about 0.1 to about 500 micrograms of DNA. In some embodiments, the pharmaceutical compositions contain about 1 to about 350 micrograms of DNA. In some embodiments, the pharmaceutical compositions contain about 5 to about 250 micrograms of DNA. In some embodiments, the pharmaceutical compositions contain about 10 to about 200 micrograms of DNA. In some embodiments, the pharmaceutical compositions contain about 15 to about 150 micrograms of DNA. In some embodiments, the pharmaceutical compositions contain about 20 to about 100 micrograms of DNA. In some embodiments, the pharmaceutical compositions contain about 25 to about 75 micrograms of DNA. In some embodiments, the pharmaceutical compositions contain about 30 to about 50 micrograms of DNA. In some embodiments, the pharmaceutical compositions contain about 35 to about 40 micrograms of DNA. In some embodiments, the pharmaceutical compositions contain about 100 to about 200 microgram DNA. In some embodiments, the pharmaceutical compositions comprise about 10 microgram to about 100 micrograms of DNA. In some embodiments, the pharmaceutical compositions comprise about 20 micrograms to about 80 micrograms of DNA. In some embodiments, the pharmaceutical compositions comprise about 25 micrograms to about 60 micrograms of DNA. In some embodiments, the pharmaceutical compositions comprise about 30 nanograms to about 50 micrograms of DNA. In some embodiments, the pharmaceutical compositions comprise about 35 nanograms to about 45 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms of DNA. In some preferred embodiments, the pharmaceutical compositions contain about 100 to about 200 microgram DNA.

In some embodiments, pharmaceutical compositions according to the present invention comprise at least 10, 15, 20, 25, 30, 35, 40, 45, 50, 55, 60, 65, 70, 75, 80, 85, 90, 95 or 100 nanograms of DNA of the vaccine. In some embodiments, the pharmaceutical compositions can comprise at least 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 or 1000 micrograms of DNA of the vaccine. In some embodiments, the pharmaceutical composition can comprise at least 1.5, 2, 2.5, 3, 3.5, 4, 4.5, 5, 5.5, 6, 6.5, 7, 7.5, 8, 8.5, 9, 9.5 or 10 mg or more of DNA of the vaccine.

In other embodiments, the pharmaceutical composition can comprise up to and including 15, 20, 25, 30, 35, 40, 45, 50, 55, 60, 65, 70, 75, 80, 85, 90, 95 or 100 nanograms of DNA of the vaccine. In some embodiments, the pharmaceutical composition can comprise up to and including 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995, or 1000 micrograms of DNA of the vaccine. In some embodiments, the pharmaceutical composition can comprise up to and including 1.5, 2, 2.5, 3, 3.5, 4, 4.5, 5, 5.5, 6, 6.5, 7, 7.5, 8, 8.5, 9, 9.5 or 10 mg of DNA of the vaccine.

The pharmaceutical composition can further comprise other agents for formulation purposes according to the mode of administration to be used. In cases where pharmaceutical compositions are injectable pharmaceutical compositions, they are sterile, pyrogen free and particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation.

The vaccine can further comprise a pharmaceutically acceptable excipient. The pharmaceutically acceptable excipient can be functional molecules as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent can also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid can also be used administered in conjunction with the genetic construct. In some embodiments, the DNA vector vaccines can also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant. The adjuvant can be other genes that are expressed in alternative plasmid or are deneurological systemed as proteins in combination with the plasmid above in the vaccine. The adjuvant can be selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, WIC, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, IL-6, IL-10, IL-12, IL-18, or a combination thereof. In an exemplary embodiment, the adjuvant is IL-12.

Other genes which can be useful adjuvants include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof.

In some embodiments adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. Application Serial No. and Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The vaccine may further comprise a genetic vaccine facilitator agent as described in U.S. Pat. No. 021,579 filed Apr. 1, 1994, which is fully incorporated by reference.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

The vaccine can be a DNA vaccine. DNA vaccines are disclosed in U.S. Pat. Nos. 5,593,972, 5,739,118, 5,817,637, 5,830,876, 5,962,428, 5,981,505, 5,580,859, 5,703,055, and 5,676,594, which are incorporated herein fully by reference. The DNA vaccine can further comprise elements or reagents that inhibit it from integrating into the chromosome.

Examples of attenuated live vaccines, those using recombinant vectors to foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference. The genetic construct can also be part of a genome of a recombinant viral vector, including recombinant adenovirus, recombinant adenovirus associated virus and recombinant vaccinia. The genetic construct can be part of the genetic material in attenuated live microorganisms or recombinant microbial vectors which live in cells.

5. Methods of Delivery the Vaccine

Provided herein is a method for delivering the vaccine for providing genetic constructs and proteins of the consensus antigen which comprise epitopes that make them particular effective against immunogens of TB against which an immune response can be induced. The method of delivering the vaccine or vaccination may be provided to induce a therapeutic and prophylactic immune response. The vaccination process may generate in the mammal an immune response against TB. The vaccine may be delivered to an individual to modulate the activity of the mammal's immune system and enhance the immune response. The delivery of the vaccine may be the transfection of the consensus antigen as a nucleic acid molecule that is expressed in the cell and delivered to the surface of the cell upon which the immune system recognized and induces a cellular, humoral, or cellular and humoral response. The delivery of the vaccine may be used to induce or elicit and immune response in mammals against TB by administering to the mammals the vaccine as discussed above.

Upon delivery of the vaccine and plasmid into the cells of the mammal, the transfected cells will express and secrete consensus antigens for each of the plasmids injected from the vaccine. These proteins will be recognized as foreign by the immune system and antibodies will be made against them. These antibodies will be maintained by the immune system and allow for an effective response to subsequent TB infections.

Methods of delivering DNA vaccines are described in U.S. Pat. Nos. 4,945,050 and 5,036,006, both of which are incorporated herein in their entirety by reference.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

The vaccine can be used to generate an immune response in a mammal, including therapeutic or prophylactic immune response. The immune response can generate antibodies and/or killer T cells which are directed to the one or more TB antigens. Such antibodies and T cells can be isolated.

Some embodiments provide methods of generating immune responses against one or more TB antigens, which comprise administering to an individual the vaccine. Some embodiments provide methods of prophylactically vaccinating an individual against TB infection, which comprise administering the vaccine. Some embodiments provide methods of therapeutically vaccinating an individual that has been infected with TB which comprise administering the vaccine. Diagnosis of TB infection prior to administration of the vaccine can be done routinely.

The vaccine induces humoral immunogenicity and provides protection against lethal challenge with TB providing 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% protection against lethal challenge after vaccination with multivalent TB vaccine constructs as described herein.

a. Combination Treatments

The vaccine may be administered in combination with other proteins and/or genes encoding CCL20, α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAIL-recDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof. In some embodiments, the vaccine is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well-known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

b. Electroporation

The vaccine or pharmaceutical composition can be administered by electroporation. Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation can be accomplished using an in vivo electroporation device, for example CELLECTRA® EP system (Inovio Pharmaceuticals, Inc., Blue Bell, Pa.) or Elgen electroporator (Inovio Pharmaceuticals, Inc.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 μs, 20 μs, 10 μs or 1 μs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing DNA Plasmids

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims Example 1

A total of 9 multivalent TB constructs were initially made. They consist of the following: 6 trivalent pVax vectors containing 15 esat-6 family (esx) proteins; two bivalent vectors that fused esat6 (esxA) in combination with two other immunogenic TB antigens: Ag85A and Ag85B; and a multivalent vector expressing six selected esx proteins. The distribution of the esx family members in the constructs is set out in Table 3.

Figure 1B:
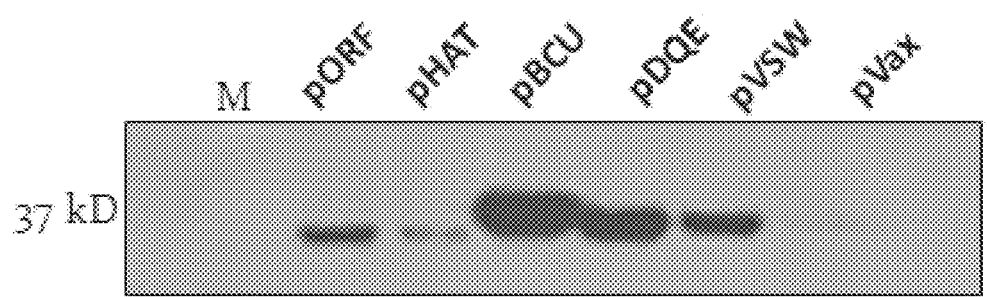
FIG. 1B provides data showing antigen expression for five esx constructs.

All multivalent vectors were separated by endoproteolytic (furin) cleavage sites, which will allow for the secretion of each individual protein. Furthermore, the constructs were synthetically designed and codon and RNA optimized to improve expression. In addition, all putative antigens that had either C-mannosyiation (W-X-X-W (SEQ ID NO:29)) or N-linked glycosylation (N-X-S/T) canonical sequences were modified by point mutation as shown in FIG. 2. Preventing mammalian glycosylation of a bacterially delivered sequence produced in a mammalian host was a goal of the construction. All sequences were synthesized into a pUC57 vector that contained a kozak consensus sequence and IgE leader sequence at the 5' end, to help enhance both protein efficiency and synthesis, and a poly A tail to end translation. Inserts were cloned into the pVAX expression promoter between the BamHI and XhoI sites. Construct design of the multivalent plasmids is illustrated in FIG. 1A. Prior to immunogenicity studies in mice, western blotting confirmed expression of all constructs. FIG. 1B illustrates some examples. The amino acid sequences of all constructs are given in FIG. 2.

Figure 3:
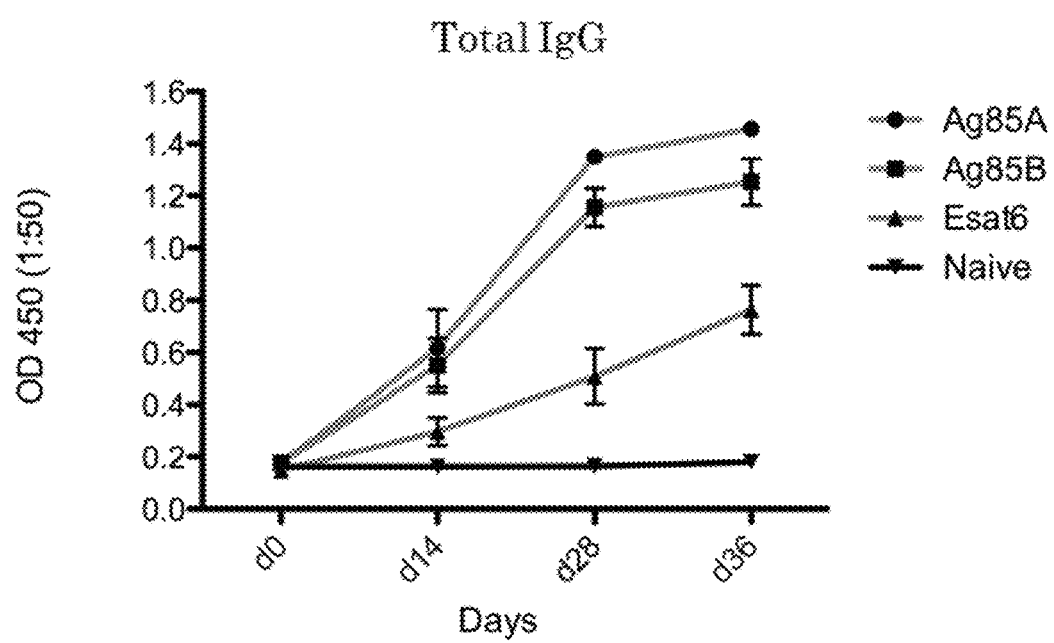
FIG. 3 shows humoral immune responses in response to multivalent vaccine administration.
Figure 4A:
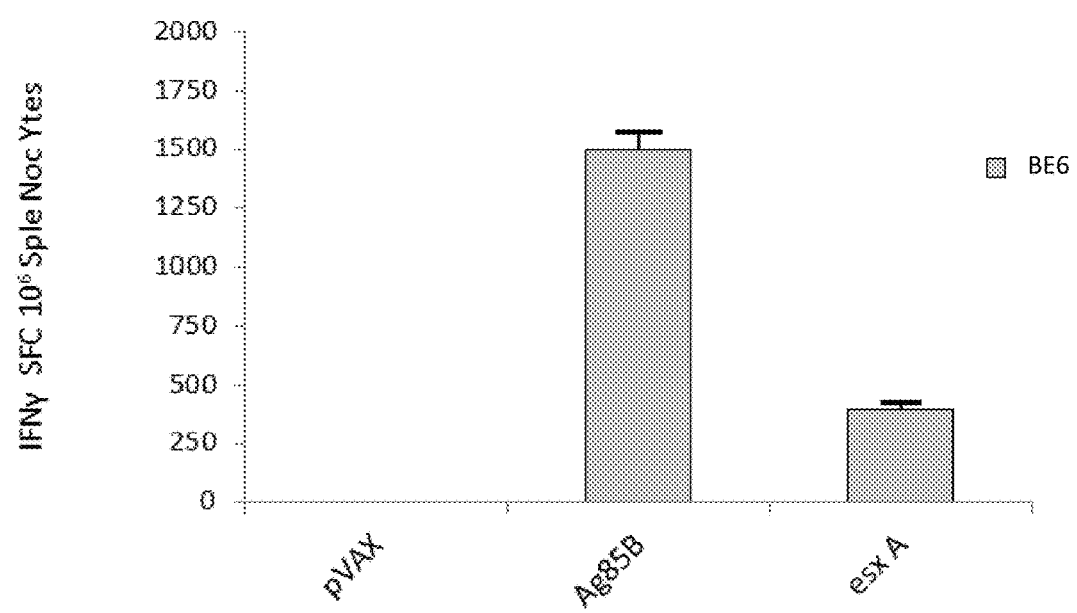
FIGS. 4A-4C provide bar graphs showing cellular immune responses to multivalent vaccines.
Figure 4B:
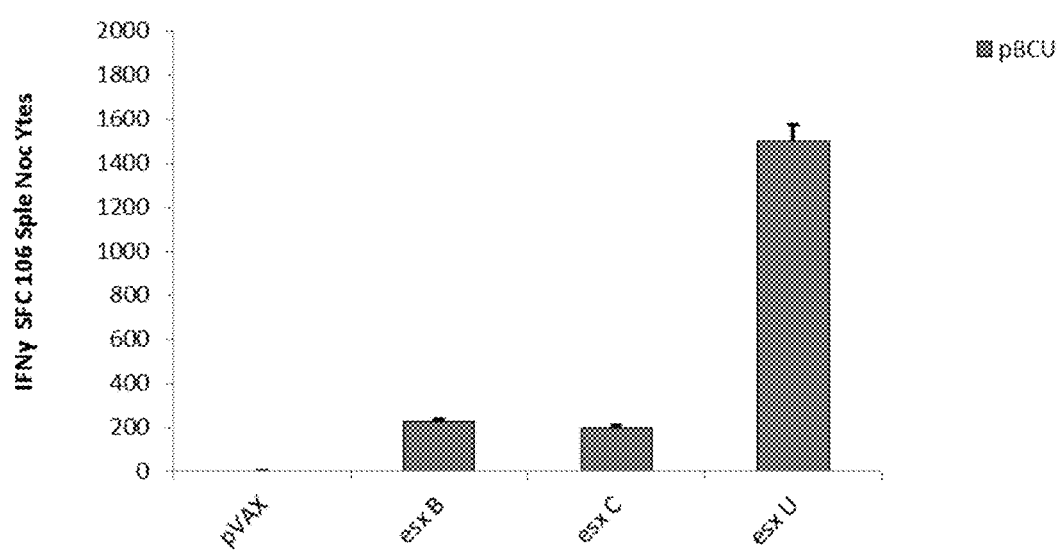
Figure 4C:
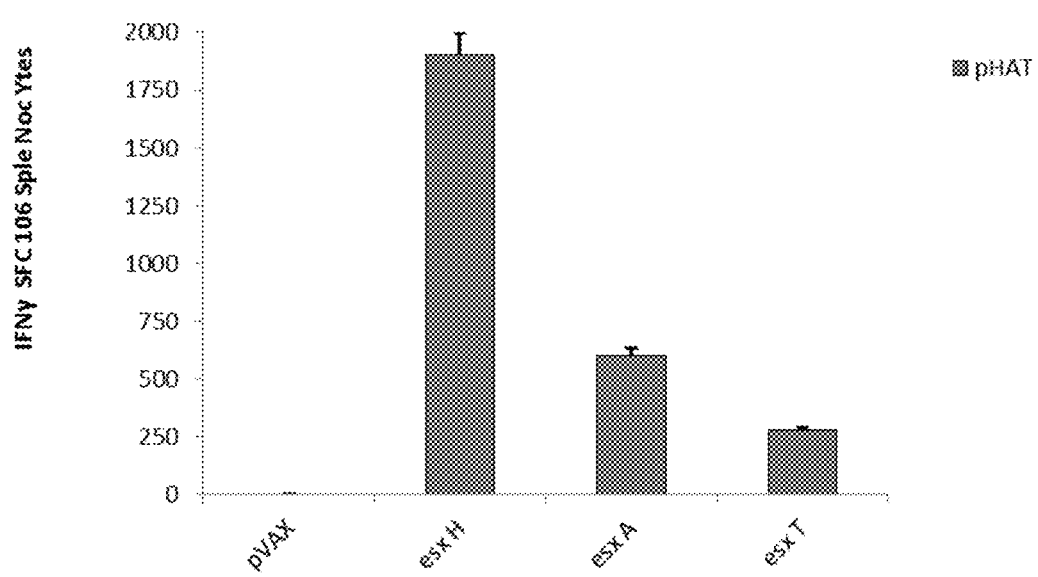

The magnitude of the humoral and cellular immune response induced by the novel esx vaccine in B6 mice was evaluated. The cellular immune responses were determined by Interferon-gamma ELISpots. Some examples of the production of specific binding antibodies against our multivalent vectors were observed. Antigen-specific antibodies were detected using enzyme linked immunosorbent assay (ELISA). Examples of both humoral and cellular immogenicity to our constructs are reported in FIGS. 3 and 4.

FIG. 1A depicts the construction of multivalent esx vaccine plasmids and in vitro expression of the trivalent expression vectors. Multivalent TB esx vaccine plasmids were constructed. FIG. 1a shows the site and manner in which ESX sequences are cloned into the pVax1 vector.

FIG. 1B provides data showing antigen expression for five esx constructs. The data was generated by Western blotting. Expression was confirmed using transfected RD cells with Turbofectin. After 24 hours, cells were harvested and total cell lysate was obtained and the protein was quantified. The synthesized proteins were detected using an anti-HA antibody (the HA tag is located in the C-terminus region of the transgene). pVAX1 was used as a negative control.

FIG. 2A and FIG. 2B show the modified amino acid insert sequences for the multivalent TB vaccine constructs. Protein sequences show all constructs with novel IgE leader sequences underlined in blue/italics as first 18 amino acids at each N terminus; furin cleavage sequence sites are lower case/broken underscore/highlighted in yellow; C-manosylation mutation underlined in red and N-linked glycosylation mutation underlined in bold. The antigens (esxA, esxE, esxF, esxU, esxW) that have amino acids underlined in bold had N-linked glycosylation canonical sequence sites mutated (N-X-S/T to N-X-A). Amino acids double underlined in red had C-mannosylation canonical sequence sites mutated (W-X-X-W—SEQ ID NO: 29 to W-X-X-A—SEQ ID NO: 30 or W-X-X-W to A-X-X-W—SEQ ID NO: 31).

FIG. 3 shows humoral immune responses I n response to multivalent vaccine administration. Anti-antigen specific TB IgG responses in serum from (n=5 per group) naive mice and vector specific-immunized mice after immunization schedule as measured by ELISA at different time points are shown. The Ag85A-specific response of AE6 construct and Ag85B-specific and Esat-6-specific responses of the multivalent BE6 construct are shown.

FIGS. 4A-4C provides bar graphs showing cellular immune responses to multivalent vaccines. Cellular immunogenicity of the multivalent constructs determined by IFN gamma ELISpot. For cellular immunogenicity studies, 45 ug of each antigen was delivered to the tibialis anterior muscle of B6 mice by intramuscular injection followed by electroporation using CELLECTRA adaptie constant current device (Inovio). Mice (n=5 per group) received 3 immunizations at 2 week intervals (weeks 0, 2, and 4). Cellular responses were assessed 8 days after last immunization (week 5). ELISpots were carried out per manufactures instructions (R&D Systems) using 96 well plates (Millipore). 200,000 splenocytes from each immunized mouse were added to each well of the plates and stimulated overnight at 37 degrees Celsius, 5% CO2, in the presence of R10 (negative control), conanacalin A (positive control), or peptide pools specific to each antigen. Peptide pools are composed of 15-mer peptides spanning the entire protein, overlapping by 9 or 11 amino acids.

Synthetic Multivalent immunogen collection is shown here to drive diverse and relevant immunity against the broad spectrum of ESAT 6 gene family members. This immune approach can be useful in immune therapy of TB patients or in Prime boost modalities or as a stand alone approach for controlling TB infection.

References (incorporated herein by reference in their entirety):

1. Cayabyab, M. J. et al. Current and novel approaches to vaccine development against tuberculosis. *Front Ceil infect Microbiol.* 2: 154 (2012).
2. Skjot, R. L. et al. Comparative evaluation of low-molecular-mass proteins from Mtb identifies members of the ESAT-6 family as immunodominant T-cell antigens, *Infect Immun.* 68: 214-220 (2000).
3. Brodin P. et al. ESAT-6 proteins: protective antigens and virulence factors? *Trends Microbiol* 12: 500-8 (2004).
4. Sutcliffe I. C. New insights into the distribution of EXG100 protein secretion systems. *Antonie Van Leeuwenhoek* 99: 127-131 (2011)

Example 2

Using coding sequences designed for optimized expression, additional esx constructs were constructed and tested for expression. FIG. 5A shows a schematic representation of all five new trivalent esx constructs encompassing coding sequences of a total of 15 esx antigens. Similar to other constructs, all genes were cloned into the pVAX1 mammalian vector and were under the CMV promoter. Each insert comprises the coding sequence of N-terminal IgE leader peptide, coding sequences for a set of three esx antigens that have coding sequences for a protease cleavage site between two adjacent esx antigens coding sequences, coding sequence for C-terminal HA tag. These inserts are inserted into the pVAX1 vector between the CMV promoter sequence and sequences for BGH polyA signal. The pVAX1 vector also comprises a kanamycin resistance gene and pUC origin.

Each of the 5 inserts are shown in FIG. 5A and labeled I-V.

Insert I show in FIG. 5A comprises coding sequence of N-terminal IgE leader peptide, coding sequence the esx antigen esxO, coding sequence for a furan proteolytic cleavage site, coding sequence the esx antigen esxR, coding sequence for a furan proteolytic cleavage site, coding sequence the esx antigen esxF, and coding sequence for C-terminal HA tag. The coding sequence for this insert is SEQ ID NO:27 and referred to as the new version of the pORF (pORF.2) insert, which when cloned into pVAX1 was designated as the new version of pORF (pORF.2) plasmid.

Insert II show in FIG. 5A comprises coding sequence of N-terminal IgE leader peptide, coding sequence the esx antigen esxB, coding sequence for a furan proteolytic cleavage site, coding sequence the esx antigen esxC, coding sequence for a furan proteolytic cleavage site, coding sequence the esx antigen esxU, and coding sequence for C-terminal HA tag. The coding sequence for this insert is SEQ ID NO:25 and referred to as the new version of the pBCU (pBCU.2) insert, which when cloned into pVAX1 was designated as the new version of pBCU (pBCU.2) plasmid.

Figure 5A:
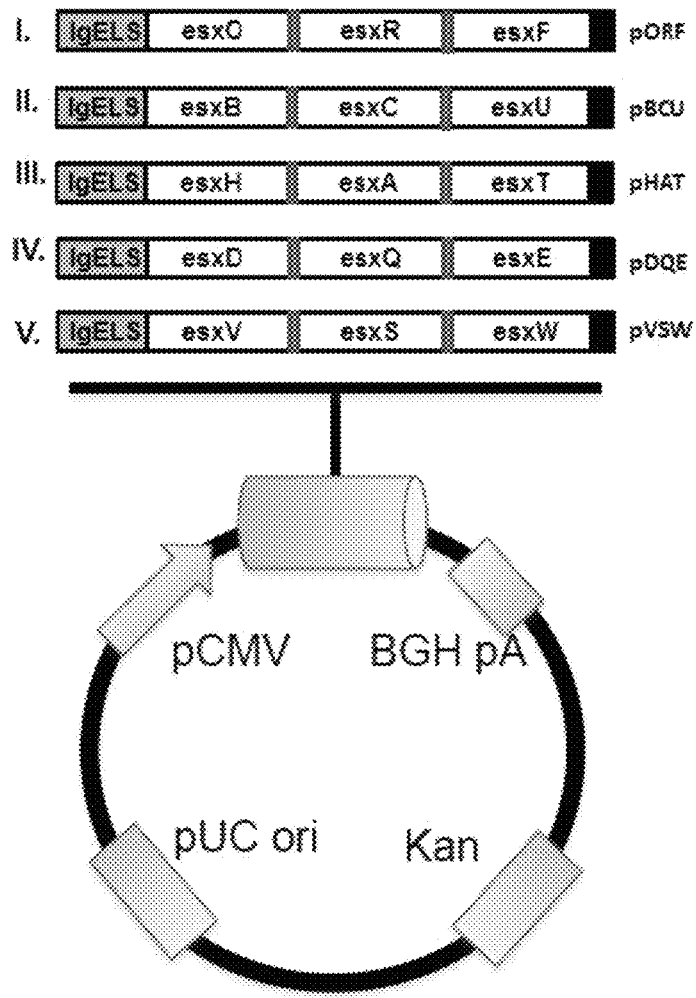
FIGS. 5A and 5B depict the construction of the new versions of pVSW, pBCU, pDQE, pHAT and pORF (pVSW.2, pBCU.2, pDQE.2, pHAT.2 and pORF.2) inserts and plasmids and include experimental results showing that the insert is expressed in mammalian cells transfected with the plasmid.

Insert III show in FIG. 5A comprises coding sequence of N-terminal IgE leader peptide, coding sequence the esx antigen esxH, coding sequence for a furan proteolytic cleavage site, coding sequence the esx antigen esxA, coding sequence for a furan proteolytic cleavage site, coding sequence the esx antigen esxT, and coding sequence for C-terminal HA tag. The coding sequence for this insert is SEQ ID NO:23 and referred to as the new version of the pHAT (pHAT.2) insert, which when cloned into pVAX1 was designated as the new version of pHAT (pHAT.2) plasmid.

Insert IV show in FIG. 5A comprises coding sequence of N-terminal IgE leader peptide, coding sequence the esx antigen esxD, coding sequence for a furan proteolytic cleavage site, coding sequence the esx antigen esxQ, coding sequence for a furan proteolytic cleavage site, coding sequence the esx antigen esxE, and coding sequence for C-terminal HA tag. The coding sequence for this insert is SEQ ID NO:21 and referred to as the new version of the pDQE (pDQE.2) insert, which when cloned into pVAX1 was designated as the new version of pDQE (pDQE.2) plasmid.

Insert V show in FIG. 5A comprises coding sequence of N-terminal IgE leader peptide, coding sequence the esx antigen esxV, coding sequence for a furan proteolytic cleavage site, coding sequence the esx antigen esxS, coding sequence for a furan proteolytic cleavage site, coding sequence the esx antigen esxW, and coding sequence for C-terminal HA tag. The coding sequence for this insert is SEQ ID NO:19 and referred to as the new version of the pVSW (pVSW.2) insert, which when cloned into pVAX1 was designated as the new version of pVSW (pVSW.2) plasmid.

Figure 5B:
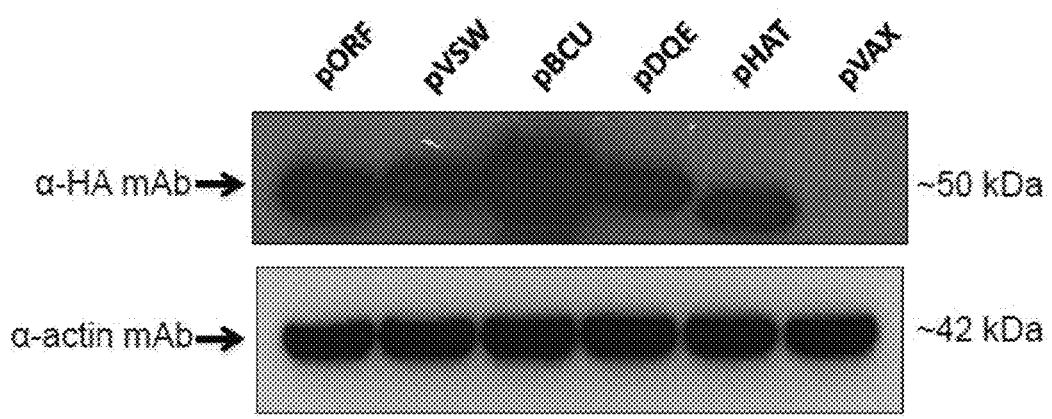
Figure 6A:
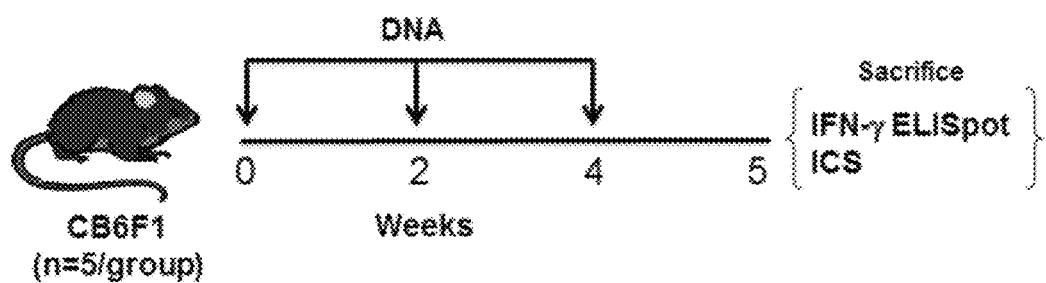
FIGS. 6A-6F show experimental design and results from experiments comparing the immune responses induced against each of three specific esx antigens included in each of the five new versions of plasmids (new versions of pVSW, pBCU, pDQE, pHAT and pORF, (pVSW.2, pBCU.2, pDQE.2, pHAT.2 and pORF.2)).
Figure 6B:
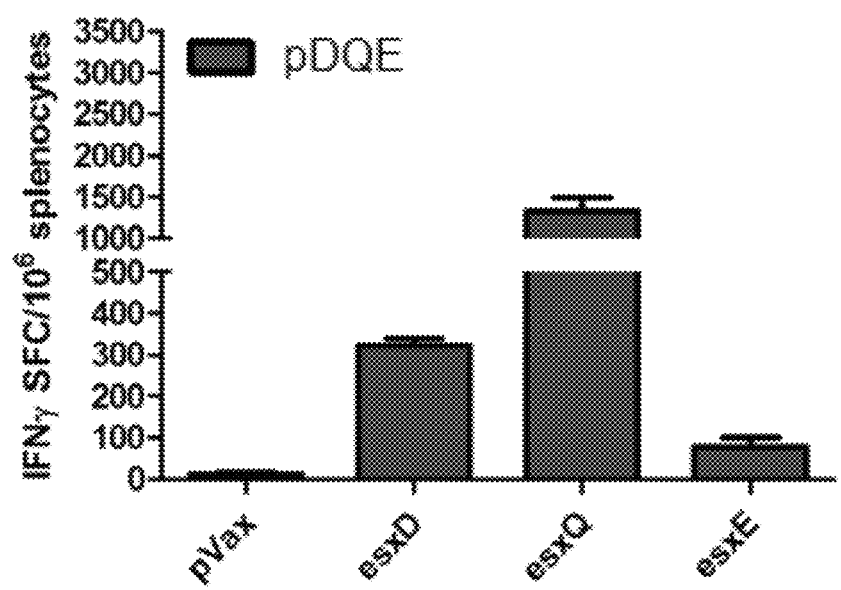
Figure 6C:
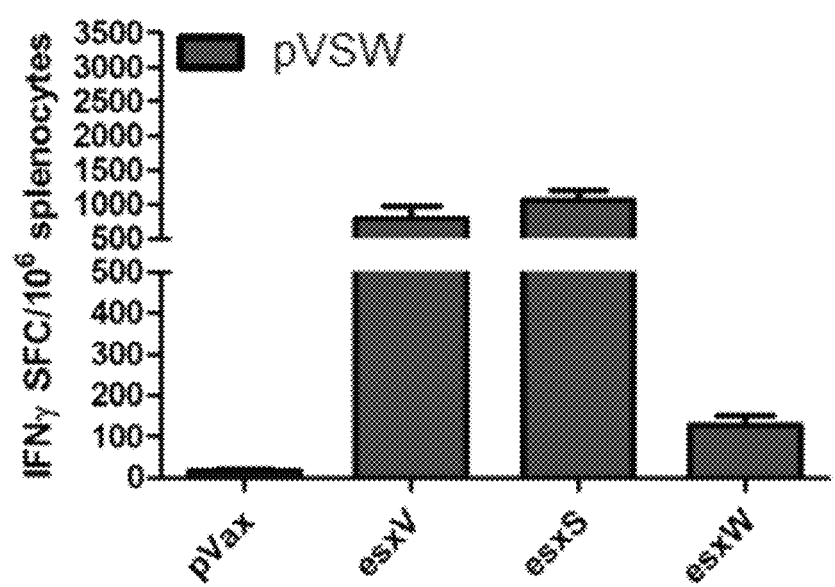
Figure 6D:
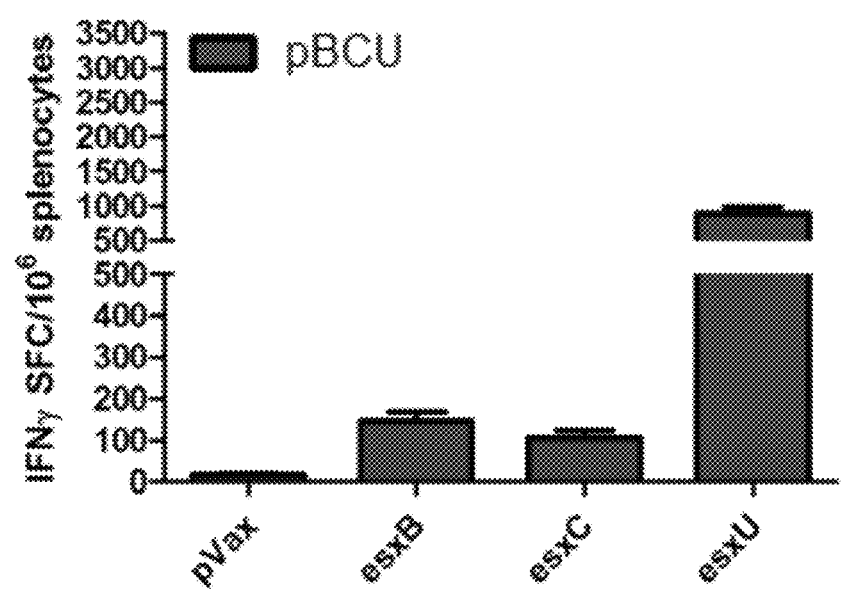
Figure 6E:
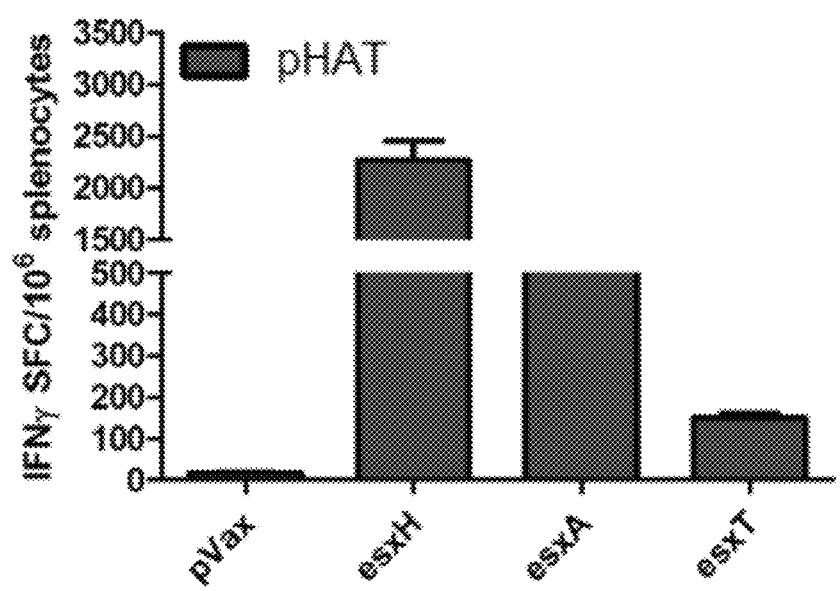
Figure 6F:
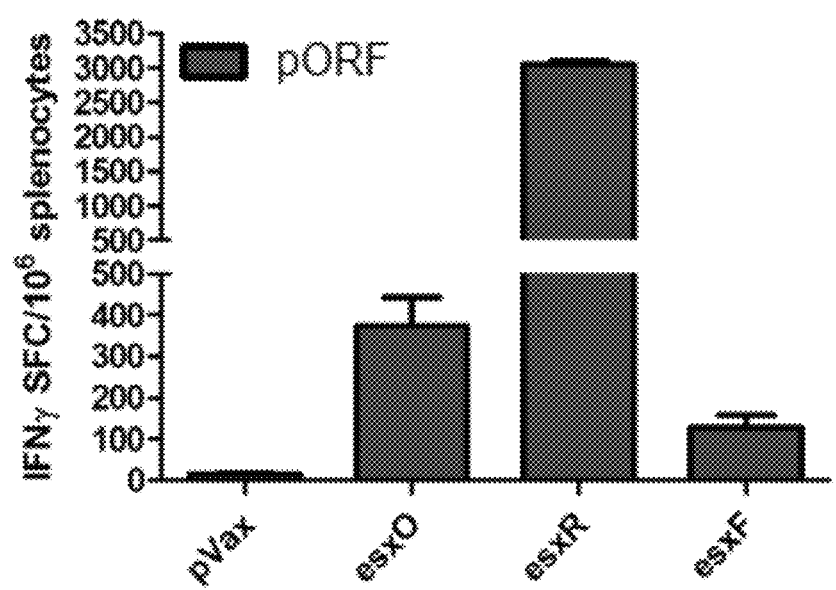
Figure 7A:
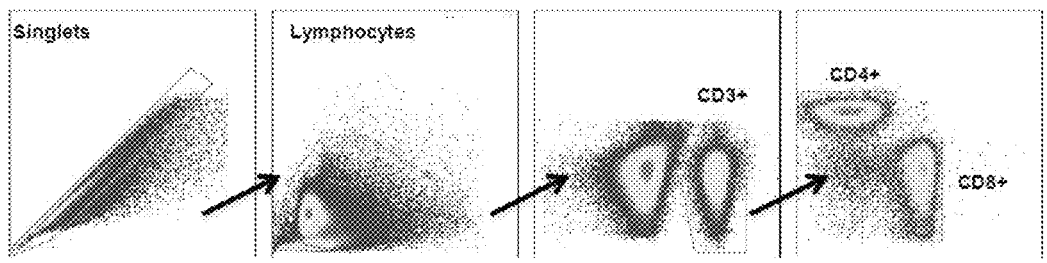
FIGS. 7A-7C show experiment results from experiments evaluating esx-specific CD4 and CD8 T cells responses following vaccination with a combination of the new versions of pVSW, pBCU, pDQE, pHAT and pORF, (pVSW.2, pBCU.2, pDQE.2, pHAT.2 and pORF.2).
Figure 7B:
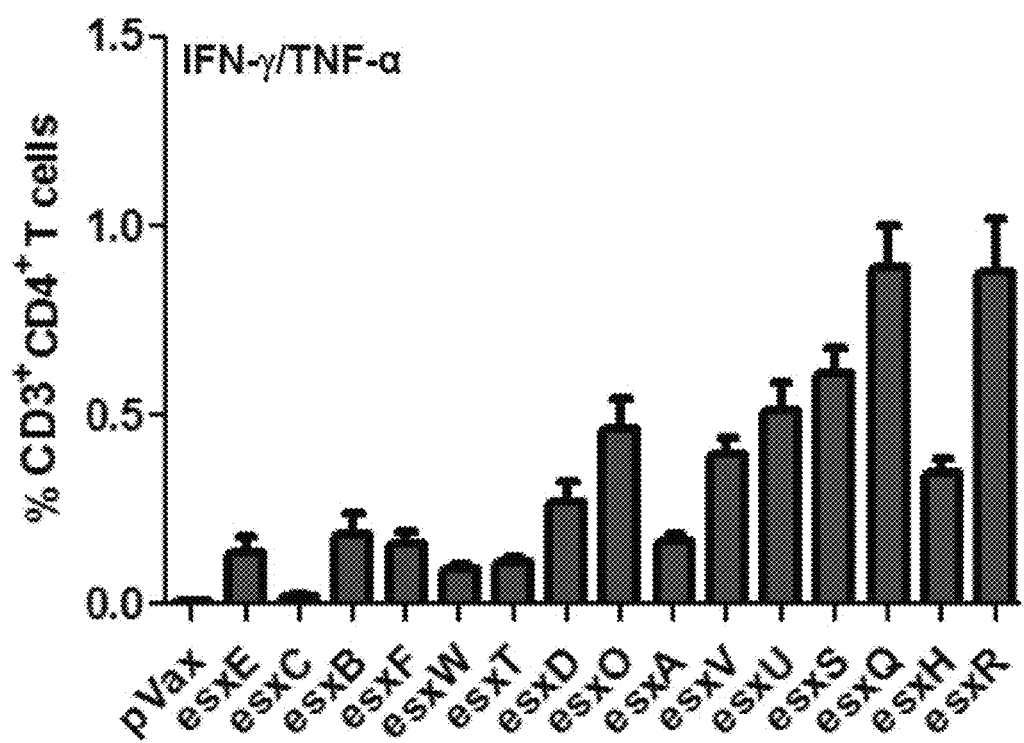
Figure 7C:
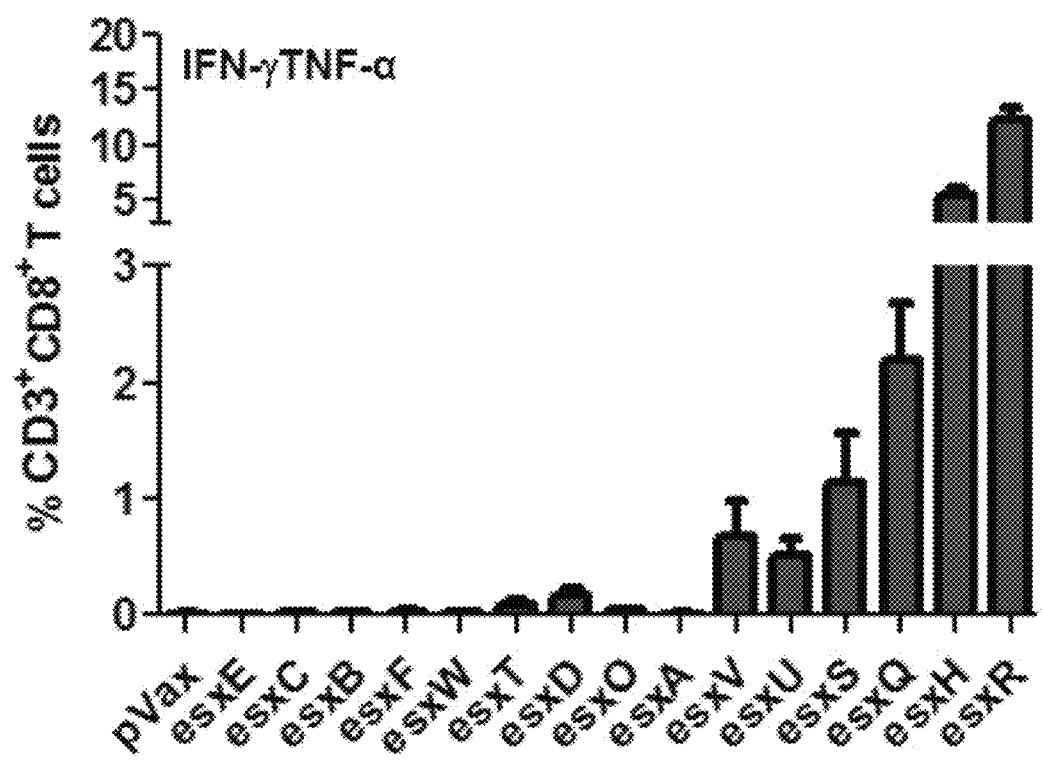

FIG. 5B shows results from experiments testing expression of the esx having Inserts I-V. RD cells were transfected one of the new versions of pVSW, pBCU, pDQE, pHAT and pORF, (pVSW.2, pBCU.2, pDQE.2, pHAT.2 and pORF.2) plasmid or the control plasmid pVAX. Expression was analyzed by Western blot analysis detected using an anti-HA mAb. Also shown is a loading control by staining for actin and relative sizes are indicated (KDa). The data shows that protein was detected with the anti-HA mAb in every test assay except the pVAX sample. The experiments demonstrate that the Inserts in the new versions of pVSW, pBCU, pDQE, pHAT and pORF plasmids (pVSW.2, pBCU.2, pDQE.2, pHAT.2 and pORF.2 plasmids) are expressed in mammalian cells.

Immunogenicity of esx antigens encoded and expressed by the new versions of pVSW, pBCU, pDQE, pHAT and pORF plasmids (pVSW.2, pBCU.2, pDQE.2, pHAT.2 and pORF.2 plasmids) were compared in experiments using mice. FIG. 6A shows an overview of the experimental protocol. CB6F1 mice (n=5 per group) were vaccinated plus electroporation (EP) with one of the new versions of pVSW, pBCU, pDQE, pHAT and pORF plasmids (pVSW.2, pBCU.2, pDQE.2, pHAT.2 and pORF.2 plasmids) three times at two week intervals (weeks 0, 2 and 4) and spleens were harvested 1 week after last immunization (week 5) to analysis the cellular immune responses by IFN-γ ELISpot assays.

FIGS. 6B-6F show data from the experiments measuring cellular immune responses to each of the three individual esx antigens encoded by one of the new versions of pVSW, pBCU, pDQE, pHAT and pORF plasmids (pVSW.2, pBCU.2, pDQE.2, pHAT.2 and pORF.2 plasmids) used in the vaccination of the Esx-specific T cell responses were measured against a pool of peptides to their respective antigens by IFN-γ ELISpot. Error bars indicate SEM and experiments were performed independently at least two times with similar results.

FIG. 6B shows results from experiments in which mice were vaccinated with the new version of plasmid pDQE (pDQE.2). Immune responses were detected against each of antigen esxD, esxQ and esxE with the greatest response against esxQ.

FIG. 6C shows results from experiments in which mice were vaccinated with the new version of plasmid pVSW (pVSW.2). Immune responses were detected against each of antigen esxV, esxS and esxW with the high responses against esxS and eszW.

FIG. 6D shows results from experiments in which mice were vaccinated with the new version of plasmid pBCU (pBCU.2). Immune responses were detected against each of antigen esxB, esxC and esxU with the greatest response against esxU.

FIG. 6E shows results from experiments in which mice were vaccinated with the new version of plasmid pHAT (pHAT.2). Immune responses were detected against each of antigen esxH, esxA and esxT with the highest response against esxH.

FIG. 6F shows results from experiments in which mice were vaccinated with the new version of plasmid pORF (pORF.2). Immune responses were detected against each of antigen esxO, esxR and esxF with the highest response against esxR.

The esx-specific CD4 and CD8 T cells responses following DNA vaccination with one of the new versions of pVSW, pBCU, pDQE, pHAT and pORF plasmids (pVSW.2, pBCU.2, pDQE.2, pHAT.2 and pORF.2 plasmids) was evaluated. CB6F1 mice (n=5) were immunized by i.m./EP with 3 injections at 3 week intervals with 20 μg of each individual new versions of pVSW, pBCU, pDQE, pHAT and pORF, (pVSW.2, pBCU.2, pDQE.2, pHAT.2 and pORF.2) Splenocytes were collected one week after final vaccination, stimulated with their respective peptide pools and analyzed by flow cytometry following intracellular staining using antibodies against IFN-γ and TNF-α. The results are shown in FIGS. 7A to 7C.

FIG. 7A shows the gating strategy used to analyze the frequency of CD4 and CD8 T cells positive for both IFN-γ and TNF-α cytokines.

FIG. 7B is a bar graph depicting esx-specific CD4 T cells releasing dual cytokines IFN-γ/TNF-α (and pVAX control) in response to esx-specific peptide antigens.

FIG. 7C is a bar graph depicting esx-specific CD8 T cells releasing dual cytokines IFN-γ/TNF-α (and pVAX control) in response to esx-specific peptide antigens. In measuring the results of these experiments in FIGS. 7B and 7C, background staining from cells stimulated with medium alone has been subtracted. Error bars represent SEM of 5 mice per group. Experiments were performed independently at least two times with similar results. Experiments were performed comparing immune responses induced by RSQ-15 vaccine, which is the combination of each individual new versions of pVSW, pBCU, pDQE, pHAT and pORF plasmids (pVSW.2, pBCU.2, pDQE.2, pHAT.2 and pORF.2 plasmids), with those induced by BCG vaccine SSI, BCG Statens Serum Institut (SSI) strain, also referred to as *Bacillus* Calmette-Guerin (BCG) strain Danish from the Statens Serum Institute (SSI BCG) or BCG as referred to in the figures. A broader and stronger esx-specific Th1 immune response was induced the RSQ-15 vaccine compared to BCG.

Figure 8A:
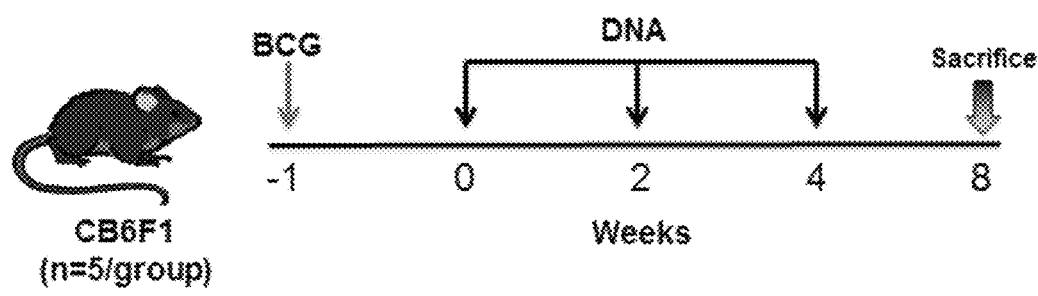
FIGS. 8A-8C show experiment design and results from experiments comparing immune responses in animals immunized with RSQ-15 (a cocktail of each of the new versions of pVSW, pBCU, pDQE, pHAT and pORF, (pVSW.2, pBCU.2, pDQE.2, pHAT.2 and pORF.2)) to immune responses induced by the TB vaccine BCG.

FIG. 8A shows an overview of the protocol involving immunization schedule for RSQ-15 and BCG vaccination. CB6F1 mice (n=5) were immunized three times at two week intervals (weeks 0, 2 and 4) with all esx constructs (each individual new versions of pVSW, pBCU, pDQE, pHAT and pORF plasmids (pVSW.2, pBCU.2, pDQE.2, pHAT.2 and pORF.2 plasmids)) co-delivered as a cocktail (RSQ-15 vaccine; 20 ug per esx construct). CB6F1 mice (n=5) were immunized by a single s.c. BCG vaccine injection (106 CFU) at week −1. At week 8, which was one month after the final immunization in the RSQ-15 group and 9 weeks after the BCG vaccination in the BCG group, T cell responses were analyzed using splenocytes from RSQ-15-primed or BCG-primed mice. The splenocytes were stimulated with all individual esx-specific peptide pools and IFN-γ production measured by ELISpot assay.

Figure 8B:
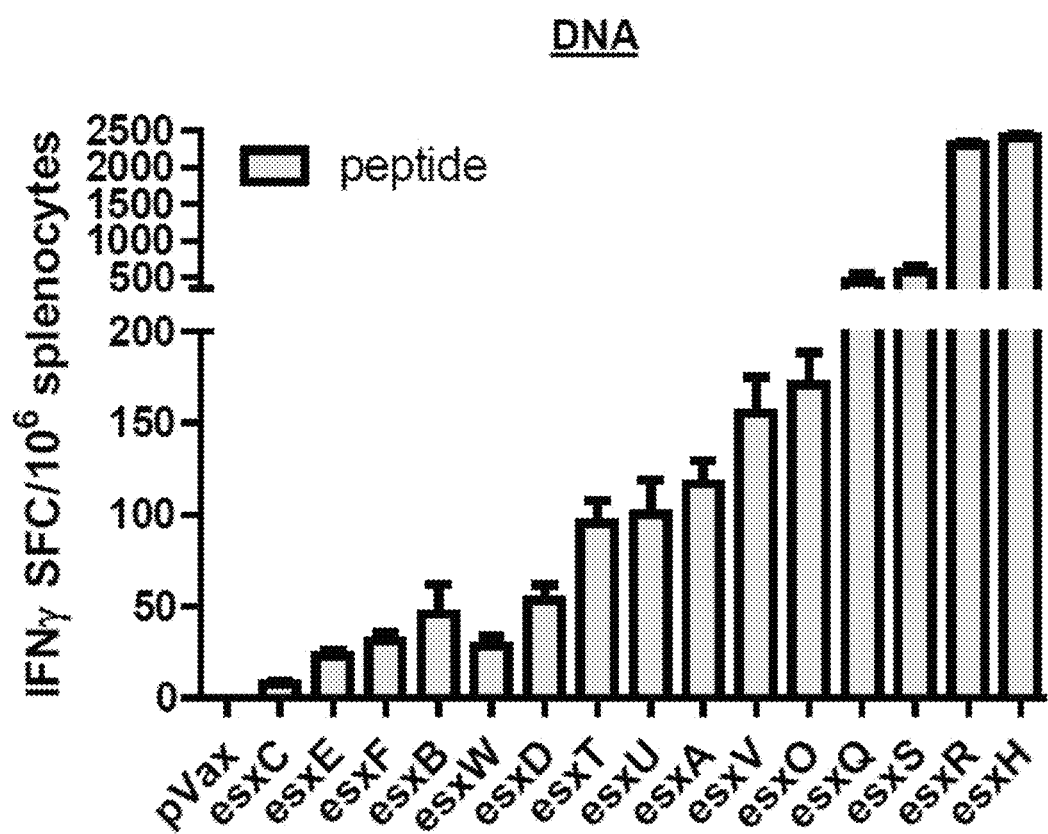
Figure 8C:
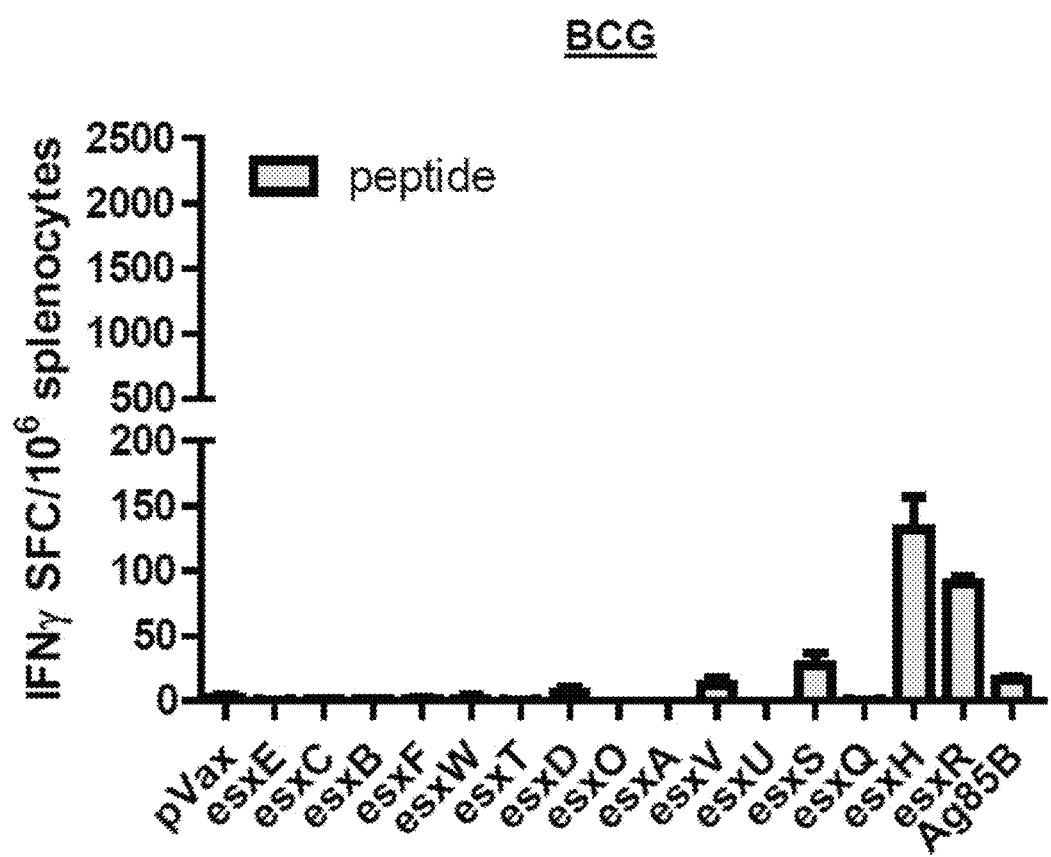

FIGS. 8B and 8C shows the results from the RSQ-15 group and the BCG group, respectively. Error bars indicate SEM and experiments were performed independently at least two times with similar results. Immunization with RSQ-15 induces broader and stronger esx-specific Th1 immune responses compared to BCG.

Experiments were performed to compare immune responses in animals primed with BCG vaccine and boosted with either a single boost of RSQ-15 vaccine or with two boosts. pVAX1 and BCG-only controls were included. Results showed that prime-boost BCG vaccination with RSQ-15 DNA vaccine increases the esx-specific BCG-induced responses.

Figure 9A:
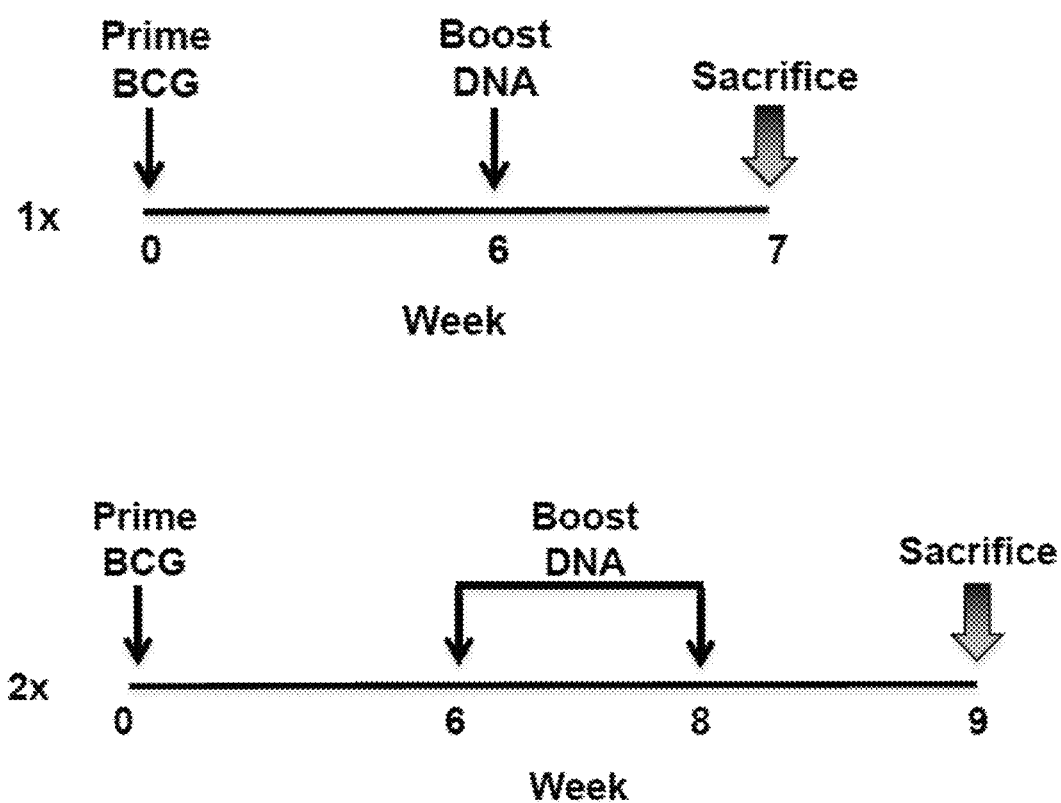
FIGS. 9A-9C show experiment design and results from Prim Boost experiments comparing esx-specific immune responses in animals immunized with BCG and boosted once or twice RSQ-15 or no boost.
Figure 9B:
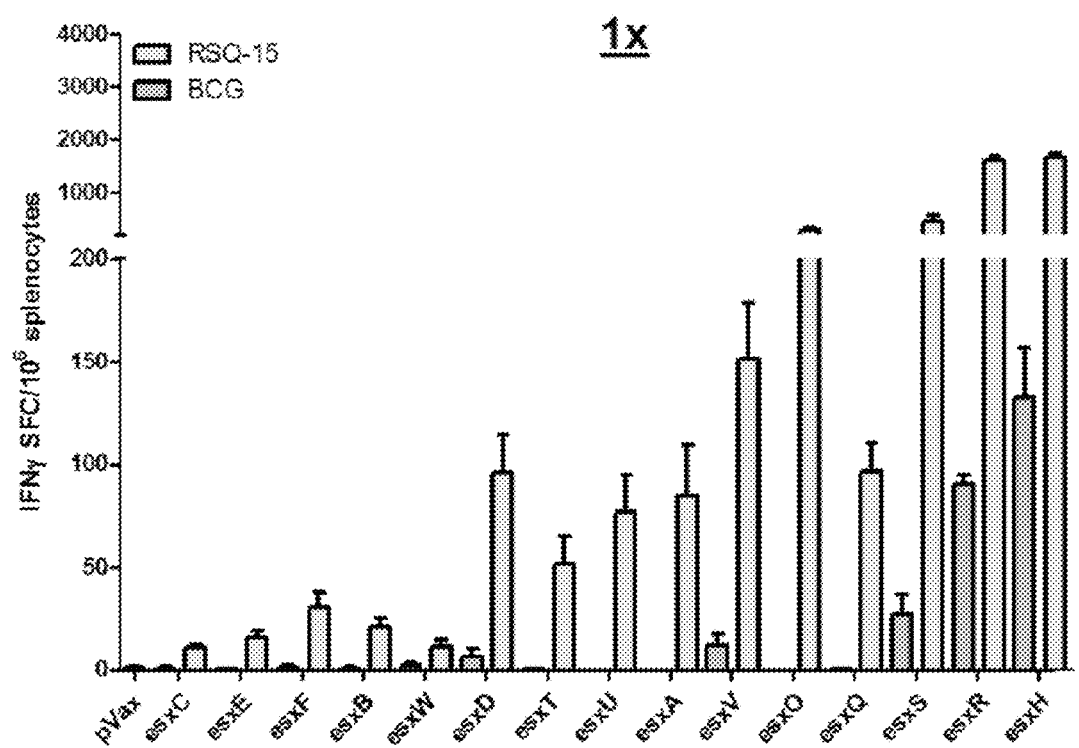
Figure 9C:
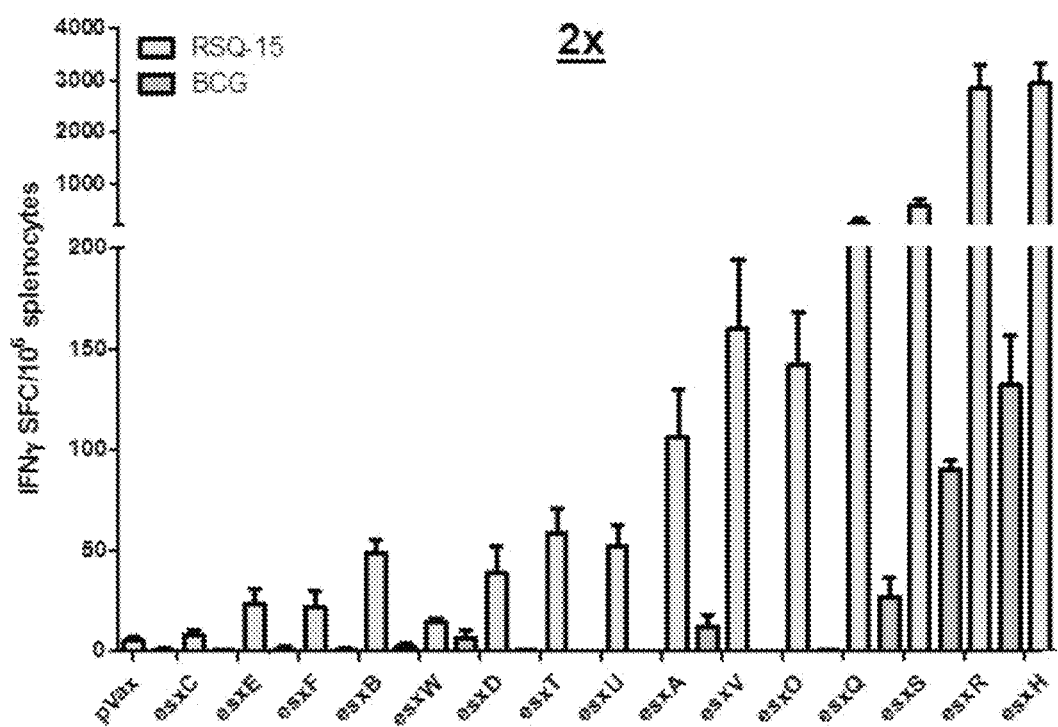

FIG. 9A shows an overview of the protocols involving immunization schedule for the two different prime-boost regimens: BCG prime, single RSQ-15 boost group versus the BCG prime, two RSQ-15 boost group. CB6F1 mice were immunized s.c. with 106 CFU of BCG SSI at week 0. Six weeks later (week 6), mice in the single boost group were boosted with 100 (20 µg per esx construct, i.e. new versions of pVSW, pBCU, pDQE, pHAT and pORF plasmids (pVSW.2, pBCU.2, pDQE.2, pHAT.2 and pORF.2 plasmids)) of the RSQ-15 vaccine by i.m. injection and sacrificed one week later at week 7. Mice in the two boost group were boosted with 100 µg the RSQ-15 vaccine by i.m. injection at week 6, boosted a second time with 100 µg of the RSQ-15 vaccine two weeks later at week 8 and sacrificed seven days after the second boost at week 9. Spleens from sacrificed mice were assayed by IFN-γ ELISpot. Results represent SEM of 5 mice per group. Experiments were performed independently at least two times with similar results. The dark bars are data from the BCG control and show that both groups of boosted animals had significantly higher immune response compared to those induced by the BCG control.

Experiments were done using new versions of pORF, pHAT and pVSW (pORF.2, pHAT.2 and pVSW.2) plasmids to measure immune responses in animals immunized with one of those new versions against other esx peptide pools selected as being from their subfamily ortholog members. The cross-reactivity of immune responses against these orthologs was assessed. Mice were either immunized with 20 µg of new version of pORF (pORF.2) three times at two week intervals, or mice were immunized with 20 µg of new version of pHAT (pHAT.2) three times at two week intervals, or mice were immunized with 20 µg of new version of pVSW (pVSW.2) three times at two week intervals. One week after the last immunization, spleens were harvested and then stimulated with their respective or ortholog esx-specific peptide pools to monitor the degree of cross-reactivity between esx antigens determined by IFN-γ ELISpot.

Figure 10A:
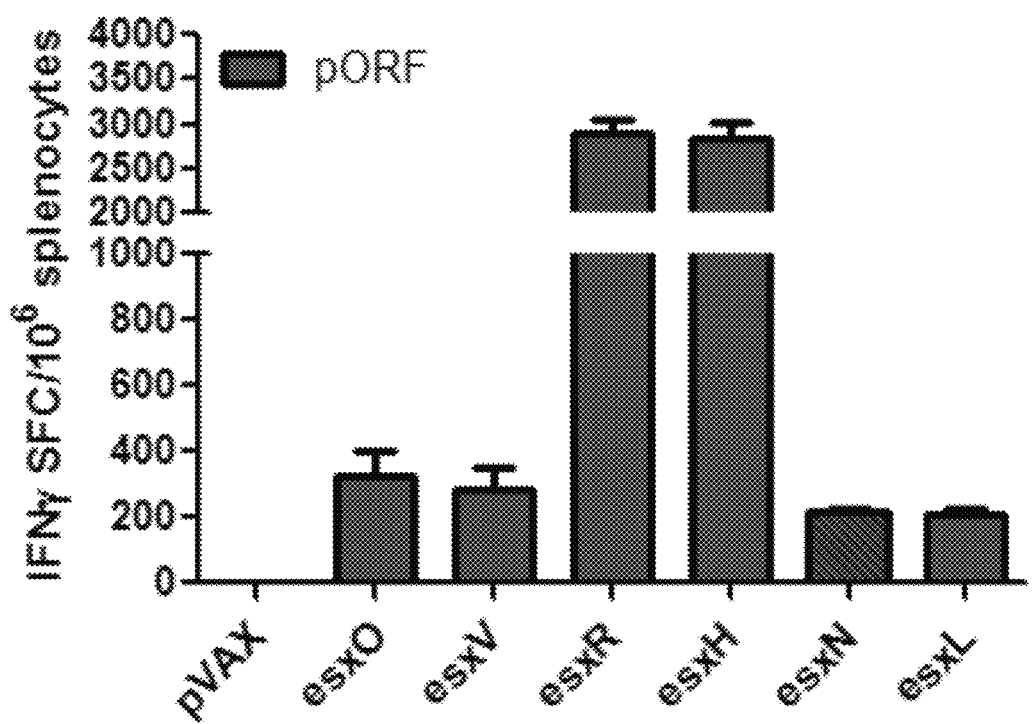
FIGS. 10A-10C show the cross reactivity of immune responses induced with one the new version pORF, pHAT or pVSW (pORF.2, pHAT.2 or pVSW.2) against subfamily ortholog members.

FIG. 10A shows results from spleens from sacrificed mice immunized with the new version of pORF (pORF.2) plasmid that were assayed by IFN-γ ELISpot mice. In addition to immune responses against esxO, immune responses recognizing esxV, esxR, esxH, esxN and esxL were observed. Error bars indicate SEM and data shown are representative of 5 mice per group in two independent experiments that generated similar results.

Figure 10B:
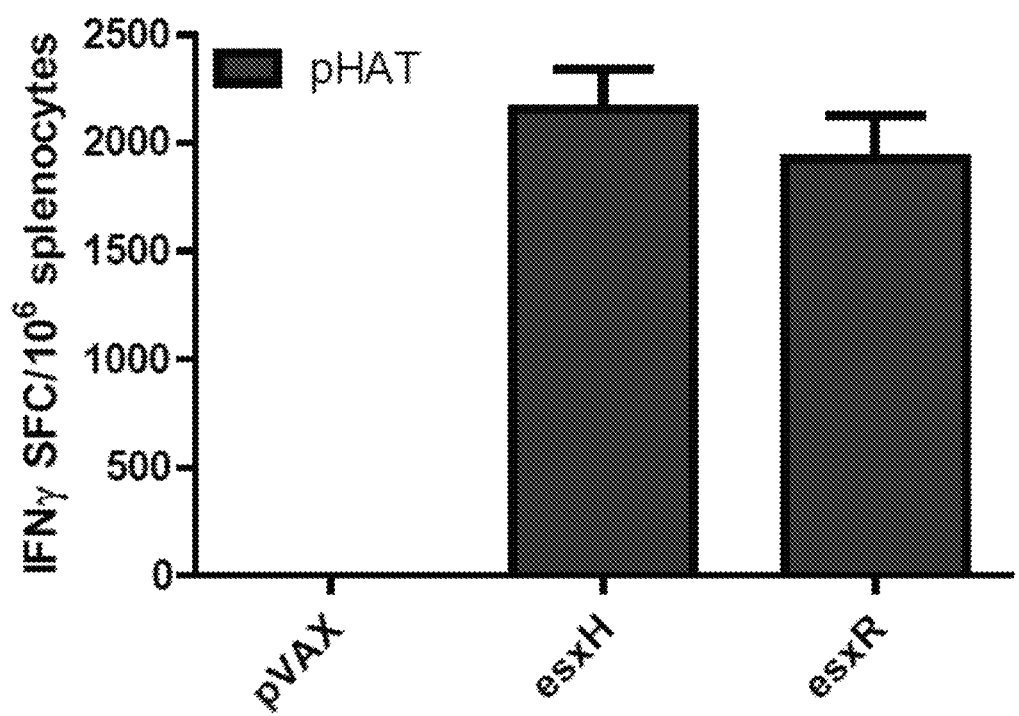

FIG. 10B shows results from spleens from sacrificed mice immunized with the new version of pHAT (pHAT.2) plasmid that were assayed by IFN-γ ELISpot mice. In addition to immune responses against esxH, immune responses recognizing esxR were observed. Error bars indicate SEM and data shown are representative of 5 mice per group in two independent experiments that generated similar results.

Figure 10C:
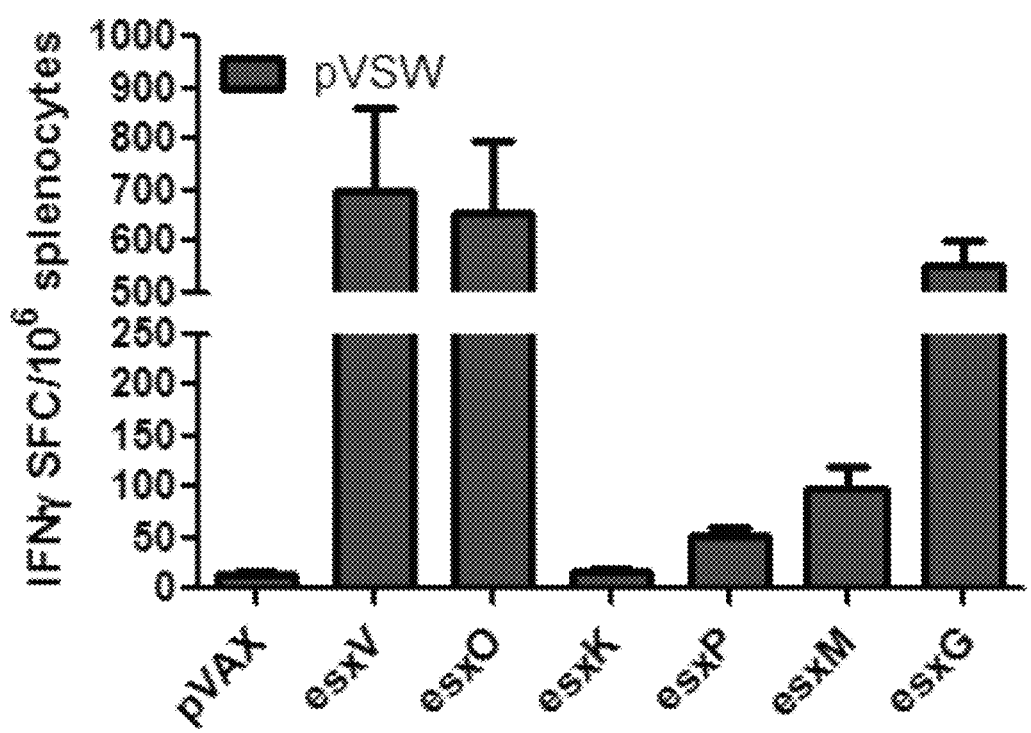

FIG. 10C shows results from spleens from sacrificed mice immunized with the new version of pVSW (pVSW.2) plasmid that were assayed by IFN-γ ELISpot mice. In addition to immune responses against esxV, immune responses recognizing esxO, esxK, esxP, esxM and esxG were observed. Error bars indicate SEM and data shown are representative of 5 mice per group in two independent experiments that generated similar results.

The invention claimed is:

1. A composition comprising one or more polypeptides selected from the group consisting of:

a) one or more polypeptide molecules selected from the group consisting of: a polypeptide comprising the combination of esxV, esxS and esxW, a polypeptide comprising the combination of esxD, esxQ and esxE, a polypeptide comprising the combination of esxH, esxA and esxT, a polypeptide comprising the combination of esxB, esxC and esxU, a polypeptide comprising the combination of esxO, esxR and esxF, a polypeptide comprising the combination of at least three esxA, a polypeptide comprising the combination of Ag85A and esxA, a polypeptide comprising the combination of Ag85B and esxA, and a polypeptide comprising the combination of esxH, esxA, esxU, esxS, esxD, and esxV; and b) a polypeptide comprising one or more sequences selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, fragments thereof having at least 90% of full length, homologous sequences having at least 95% homology, and fragments of homologous sequences having at least 95% homology, said fragment of homologous sequences having at least 95% homology having at least 90% of full length.

2. The composition of claim 1 comprising a combination of a polypeptide comprising SEQ ID NO:20, a polypeptide comprising SEQ ID NO:22, a polypeptide comprising SEQ ID NO:24, a polypeptide comprising SEQ ID NO:26, and a polypeptide comprising SEQ ID NO:28.

3. The composition of claim 1 comprising a combination of a polypeptide comprising esxV, esxS and esxW, a polypeptide comprising esxD, esxQ and esxE, a polypeptide comprising esxH, esxA and esxT, a polypeptide comprising esxB, esxC and esxU, and a polypeptide comprising esxO, esxR and esxF.

4. The composition of claim 3 comprising a combination of a polypeptide comprising SEQ ID NO:20 or SEQ ID NO:2, a polypeptide comprising SEQ ID NO:22 or SEQ ID NO:4, a polypeptide comprising SEQ ID NO:24 or SEQ ID NO:6, a polypeptide comprising SEQ ID NO:26 or SEQ ID NO:8, and a polypeptide comprising SEQ ID NO:28 or SEQ ID NO:10.

5. The composition of claim 1 comprising a polypeptide selected from the group consisting of: SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NO:28.

6. The composition of claim 1 comprising: a polypeptide comprising SEQ ID NO:2, a polypeptide comprising SEQ ID NO:4, a polypeptide comprising SEQ ID NO:6, a polypeptide comprising SEQ ID NO:8, and a polypeptide comprising SEQ ID NO:10.

7. The composition of claim 1 further comprising one or more proteins selected from the group consisting of: IL-12, IL-15 and IL-28.

8. The composition of claim 1 formulated for delivery to an individual using electroporation.

9. A method of inducing an immune response against TB comprising administering the composition of claim 1 to an individual in an amount effective to induce an immune response in said individual.

10. A method of treating an individual who has been diagnosed with TB comprising administering a therapeutically effective amount of the composition of claim 1 to an individual.

* * * * *